US012797483B2

(12) United States Patent
Oh et al.

(10) Patent No.: US 12,797,483 B2
(45) Date of Patent: Nov. 17, 2026

(54) PHARMACEUTICAL COMPOSITION FOR TREATING CANCER, CONTAINING LIPID-PHOTOTHERMAL NANOPARTICLE HAVING ANTIBODY BOUND TO SURFACE

(71) Applicant: SEOUL NATIONAL UNIVERSITY R &DB FOUNDATION, Seoul (KR)

(72) Inventors: Yu-Kyoung Oh, Seoul (KR); Young Kee Shin, Seoul (KR); Gayong Shim, Gwangmyeong-si (KR); Hobin Yang, Seoul (KR); Quoc Viet Le, Seoul (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 1084 days.

(21) Appl. No.: 17/995,273

(22) PCT Filed: Mar. 8, 2021

(86) PCT No.: PCT/KR2021/002825

§ 371 (c)(1), (2) Date: Apr. 4, 2023

(87) PCT Pub. No.: WO2021/201451

PCT Pub. Date: Oct. 7, 2021

(65) Prior Publication Data

US 2024/0293573 A1 Sep. 5, 2024

(30) Foreign Application Priority Data

Apr. 3, 2020 (KR) ........................ 10-2020-0041194
Feb. 26, 2021 (KR) ........................ 10-2021-0026866

(51) Int. Cl.

| | |
|---|---|
| ***A61P 35/00*** | (2006.01) |
| ***A61K 41/00*** | (2020.01) |
| ***A61K 47/68*** | (2017.01) |
| ***A61K 47/69*** | (2017.01) |
| ***C07K 16/30*** | (2006.01) |

(52) U.S. Cl.

CPC ...... *A61K 47/6929* (2017.08); *A61K 41/0052* (2013.01); *A61K 47/6851* (2017.08); *A61P 35/00* (2018.01); *C07K 16/30* (2013.01)

(58) Field of Classification Search

CPC ............ A61K 47/6929; A61K 41/0052; A61K 47/6851; A61K 39/395; A61K 47/6855; A61K 2039/505; A61P 35/00; C07K 16/30; C07K 16/28; C07K 16/3069; C07K 16/32; C07K 2317/24

USPC ........................................................ 424/174.1

See application file for complete search history.

(56) References Cited

U.S. PATENT DOCUMENTS

| | | | | |
|---|---|---|---|---|
| 2003/0143229 A1* | 7/2003 | Park | ....................... | C07K 16/40 530/388.25 |
| 2014/0377781 A1 | 12/2014 | Yoshida | | |
| 2022/0195045 A1* | 6/2022 | Shiraiwa | ............ | C07K 16/2809 |

FOREIGN PATENT DOCUMENTS

| | | | | |
|---|---|---|---|---|
| KR | 10-2016-0074883 A | 6/2016 | | |
| KR | 10-2019-0048819 A | 5/2019 | | |
| WO | WO-2012094727 A1 * | 7/2021 | ....... | G01N 33/54373 |

OTHER PUBLICATIONS

Vines et al. (Front Chem., Apr. 5, 2019, 7:167, pp. 1-16).*
Jose et al., "Polymeric Lipid Hybrid Nanoparticles: Properties and Therapeutic Applications", Critical Reviews in Therapeutic Drug Carrier Systems, 2018, vol. 35, No. 6, pp. 555-588.
Le et al., "In Situ Nanoadjuvant-Assembled Tumor Vaccine for Preventing Long-Term Recurrence", ACS Nano, 2019, vol. 13, pp. 7442-7462.
Yang et al., "Molecular engineering of antibodies for site-specific conjugation to lipid polydopamine hybrid hanoparticles", Acta Pharmaceutica Sinica B, 2020, vol. 10, No. 11, pp. 2212-2226.
Yang et al., "Development of Human Monoclonal Antibody for Claudin-3 Overexpressing Carcinoma Targeting", Biomolecules, 2020, vol. 10, 21 pages.

* cited by examiner

*Primary Examiner* — Yan Xiao

(74) *Attorney, Agent, or Firm* — Vorys, Sater, Seymour and Pease LLP; Mih Suhn Koh

(57) ABSTRACT

Provided are a phospholipid-photothermal nanoparticle having a cancer cell surface-specific antibody bound to the surface thereof, which can specifically bind to cancer cells, has a small particle size and excellent stability, and can effectively induce cancer cell apoptosis by exerting a photothermal effect when irradiated with near-infrared rays, and wherein the antibody or a fragment thereof is site-specifically conjugated to the phospholipid-photothermal nanoparticle, and thus the cancer cell binding ability and the photothermal cancer therapeutic effect of the phospholipid-photothermal nanoparticle are improved, and the phospholipid-photothermal nanoparticle having an antibody bound to the surface thereof are advantageously utilized for cancer therapy.

19 Claims, 52 Drawing Sheets

Specification includes a Sequence Listing.

137

PHARMACEUTICAL COMPOSITION FOR TREATING CANCER, CONTAINING LIPID-PHOTOTHERMAL NANOPARTICLE HAVING ANTIBODY BOUND TO SURFACE

The present invention relates to a pharmaceutical composition for treating cancer, containing a lipid-photothermal nanoparticle having an antibody bound to the surface thereof. Further, this application is a 371 of PCT/KR2021/002825, filed on Mar. 8, 2021, which claims the benefit of priority from Korean Patent Application Nos. 10-2020-0041194 and 10-2021-0026866 filed on Apr. 3, 2020 and Feb. 26, 2021, respectively, the contents of each of which are incorporated herein by reference in its entirety.

TECHNICAL FIELD

Sequence Listing

The Sequence Listing submitted in text format (.txt) filed on Apr. 4, 2023, named "SequenceListing.txt", created on Apr. 4, 2023 (57.6 KB), is incorporated herein by reference.

Background Art

Cancer is a major disease that accounts for the highest mortality rate in modern society, and representative cancer treatment methods include surgical operation therapy, biological therapy, radiation therapy, chemotherapy by administration of anticancer substances, and the like. Recently, immunotherapy, which tries to treat cancer using the immune system, has been attracting attention, unlike existing cancer treatment methods.

Unlike existing anticancer drugs that directly attack cancer itself, immune anticancer therapy is a method of inducing immune cells to selectively attack only cancer cells by injecting artificial immune proteins into the body to stimulate the immune system, and may be broadly divided into passive immunotherapy and active immunotherapy. Passive immunotherapy includes an immune checkpoint inhibitor, immune cell therapy, a therapeutic antibody, and the like, and among them, the immune checkpoint inhibitor is a drug that attacks cancer cells by blocking the activation of immune checkpoint proteins involved in T cell suppression to activate T cells, and includes CTLA-4, PD-1, PD-L1 inhibitors, and the like. Although an anti-PD-L1 antibody drug (Atezolizumab) was approved by the FDA for the purpose of anticancer treatment in 2016, it has the limitation of exhibiting a limited therapeutic effect as a monotherapy of immune checkpoint inhibitors. Further, active immunotherapy includes a cancer treatment vaccine, immune-modulating agents, and the like, and among them, the cancer treatment vaccine is a drug that is prepared from cancer cells or cancer cell-derived substances and activates the natural defense system of the human body by injecting the drug into the human body. However, since the cancer treatment vaccine has a complicated production process, is difficult to apply to various types of cancers, and is a personally customized therapy, there is a problem of imposing a financial burden on patients.

Meanwhile, photothermal therapy is a method of applying heat energy generated by irradiating a diseased area with a near-infrared laser after administering photosensitive materials such as gold, silver, melanin, or carbon nanoparticles such as graphene (Korean Patent Nos. 10-1773037 and 10-1374926). In particular, photothermal therapy is attracting attention as a non-invasive treatment method in the field of tumors. Anti-cancer therapy based on photothermal therapy involves injecting a photoreactive substance into tumor cells and then irradiating the tumor cells with near-infrared rays from the outside to induce the death of the tumor cells. Compared to surgical procedures, photothermal therapy is non-destructive and simple, has fewer side effects, does not require general anesthesia, causes little pain to a patient, has a short period for stability and recovery, and also has an advantage in that treatment can be repeated several times.

However, when a photosensitive material is administered alone, photothermal therapy has disadvantages in that hydrophilicity is low, photostability is low, photon yield is low, and sensitivity deteriorates. In addition, there is a disadvantage in that it is susceptible to non-specific aggregation and chemically degraded by external light, solvent and temperature changes, and there is a problem in that it is easily absorbed as a serum protein and quickly removed through the liver. Furthermore, when a photosensitive material is administered, it is not possible to distinguish between cancer cells and normal cells, so that photothermal therapy cannot be widely applied to actual clinical settings due to problems in that normal cells around cancer cells are also destroyed.

In order to overcome these disadvantages, research has been conducted to develop phototherapeutic agent particles capable of increasing stability in vivo or in vitro and specifically acting on cancer cells by entrapping photosensitive materials in nanoparticles. As the related prior art, there is Journal of Controlled Release 161 (2012) 505-522, which discloses targeted drug-delivery nanoparticles by conjugating antibodies to nanoparticles with drug entrapped inside and PEGylated surfaces.

Under such a technical background, the present inventors confirmed that lipid-photothermal nanoparticles, in which polydopamine nanoparticles, which are phototherapeutic agents, are entrapped in phospholipids, and antibodies capable of binding to antigens specifically expressed in cancer cells are bound to the phospholipid surface, could be used for cancer treatment, thereby completing the present invention.

Furthermore, the present inventors confirmed that when an antibody specific for a cancer cell surface protein was genetically modified so as to have a free thiol group and the modified antibody was site-specifically conjugated to the lipid-photothermal nanoparticles according to the present invention, the cancer cell-binding ability and cancer therapeutic effect of lipid-photothermal nanoparticles were further improved, thereby completing the present invention.

DISCLOSURE

Technical Problem

The present invention was devised to solve the aforementioned problems, and the present inventors prepared a phospholipid-photothermal nanoparticle having an antibody bound to the surface thereof, which has an excellent photothermal cancer therapeutic effect, thereby completing the present invention.

Therefore, an object of the present invention is to provide a phospholipid-photothermal nanoparticle having an antibody bound to the surface thereof, including: a phospholipid membrane with entrapped photothermal nanoparticles; and an antibody specific for the surface protein of cancer cells, or a fragment thereof, which is bound to the surface of the phospholipid membrane.

Another object of the present invention is to provide a method for preparing a phospholipid-photothermal nanoparticle having an antibody bound to the surface thereof.

However, the technical problems which the present invention intends to solve are not limited to the technical problems that have been mentioned above, and other technical problems which have not been mentioned will be clearly understood by a person with ordinary skill in the art to which the present invention pertains from the following description.

Technical Solution

The present invention provides a phospholipid-photothermal nanoparticle having an antibody bound to the surface thereof, including: a phospholipid membrane with entrapped photothermal nanoparticles; and an antibody specific for the surface protein of cancer cells, or a fragment thereof, which is bound to the surface of the phospholipid membrane.

In an exemplary embodiment, the photothermal nanoparticle may generate heat by absorbing light in the near-infrared region, but is not limited thereto.

In another exemplary embodiment, the photothermal nanoparticle may be a polydopamine nanoparticle, a gold nanoparticle, a graphene nanosheet, or a melanin nanoparticle, but is not limited thereto.

In still another exemplary embodiment, the phospholipid membrane may include any one or more selected from the group consisting of 1,2-dipalmitoyl-sn-glycero-3-phosphocholine (DPPC), 1,2-dipalmitoyl-sn-glycero-3-phosphorylglycerol (DPPG), phosphorylglycerol (PG), phosphocholine (PC) and 1,2-distearoyl-sn-glycero-3-phosphoethanolamine-N-[maleimide(polyethyleneglycol)-2000] (DSPE-PEG2000-maleimide), but is not limited thereto.

In yet another exemplary embodiment, the DPPC and DPPG may be included at a molar ratio of 5 to 9:1 to 5, but is not limited thereto.

In yet another exemplary embodiment, the DPPC, DPPG, and DSPE-PEG2000-maleimide may be included at a molar ratio of 5 to 9:1 to 5:0.01 to 1, but are not limited thereto.

In yet another exemplary embodiment, the antibody or a fragment thereof may be bound to the surface end of a PEGylated phospholipid membrane, but is not limited thereto.

In yet another exemplary embodiment, the cancer cell surface protein may be any one or more selected from the group consisting of Claudin3, HER2 and a prostate-specific membrane antigen (PSMA), but is not limited thereto.

In yet another exemplary embodiment, the antibody or a fragment thereof may be any one or more selected from the group consisting of IgG, Fab', $F(ab')_2$, Fab, Fv, a recombinant IgG (rIgG), a single chain Fv (scFv), and a diabody, but is not limited thereto.

In yet another exemplary embodiment, the antibody or a fragment thereof may be any one or more selected from the group consisting of an anti-Claudin3 antibody or a fragment thereof; herceptin or a fragment thereof; and an anti-PSMA antibody or a fragment thereof, but is not limited thereto.

In yet another exemplary embodiment, the phospholipid-photothermal nanoparticles may have a particle size of 100 to 250 nm, but the particle size is not limited thereto.

In yet another exemplary embodiment, the antibody or a fragment thereof may be modified so as to have a free thiol group, and the phospholipid membrane may include a phospholipid to which maleimide is bound, but the present invention is not limited thereto. In yet another exemplary embodiment, the free thiol group may be present in the constant site of the light chain of the antibody or a fragment thereof, but is not limited thereto.

In yet another exemplary embodiment, the free thiol group of the antibody or a fragment thereof may bind to the maleimide of the phospholipid membrane, but is not limited thereto. In yet another exemplary embodiment, the phospholipid to which maleimide is bound may be DSPE-PEG2000-maleimide, but is not limited thereto.

In yet another exemplary embodiment, the antibody or a fragment thereof may be an anti-Claudin3 antibody modified so as to have a free thiol group, or a fragment thereof, and may satisfy one or more of the following characteristics, but is not limited thereto:

(a) the modified anti-Claudin3 antibody or a fragment thereof is an anti-Claudin3 antibody including an amino acid sequence of SEQ ID NO: 9, in which the 17 glutamine residue in an amino acid sequence of SEQ ID NO: 8 is substituted with a cysteine residue, or a fragment thereof; or (b) the modified anti-Claudin3 antibody or a fragment thereof is an anti-Claudin3 antibody including an amino acid sequence of SEQ ID NO: 11, in which the 125 glutamine residue in an amino acid sequence of SEQ ID NO: 10 is substituted with a cysteine residue, or a fragment thereof.

In yet another exemplary embodiment, the anti-Claudin3 antibody modified so as to have a free thiol group, or a fragment thereof may include: a light chain variable region including any one or more of amino acid sequences of SEQ ID NOS: 4 to 7; and/or a heavy chain variable region including any one or more of amino acid sequences of SEQ ID NOS: 12 to 15, but is not limited thereto.

The present invention also provides a pharmaceutical composition for treating cancer, including the phospholipid-photothermal nanoparticle having an antibody bound to the surface thereof according to the present invention as an active ingredient.

In an exemplary embodiment, the antibody or a fragment thereof may be an anti-Claudin3 antibody or a fragment thereof, the cancer may be a cancer expressing Claudin3, but the present invention is not limited thereto.

In another exemplary embodiment, the cancer may be one or more selected from the group consisting of ovarian cancer, gastric cancer, colorectal cancer, prostate cancer, pancreatic cancer, and breast cancer, but is not limited thereto.

In still another exemplary embodiment, the phospholipid-photothermal nanoparticle may induce the death of cancer cells upon irradiation with therapeutically effective light, but is not limited thereto.

The present invention also provides a method for preparing a phospholipid-photothermal nanoparticle having an antibody bound to the surface thereof, the method including: (1) preparing polydopamine nanoparticles by mixing a dopamine hydrochloride solution with a sodium hydroxide solution; (2) preparing a phospholipid membrane by dissolving any one or more phospholipids selected from the group consisting of 1,2-dipalmitoyl-sn-glycero-3-phosphocholine (DPPC), 1,2-dipalmitoyl-sn-glycero-3-phosphorylglycerol (DPPG), phosphorylglycerol (PG), phosphocholine (PC) and 1,2-distearoyl-sn-glycero-3-phosphoethanolamine-N-[maleimide(polyethyleneglycol)-2000] (DSPE-PEG2000-maleimide) in an organic solvent and concentrating the resulting solution under reduced pressure; (3) hydrating the phospholipid membrane prepared in Step (2) by adding the polydopamine nanoparticles prepared in Step (1) to the phospholipid membrane; and (4) adding an antibody capable of binding to a cancer cell surface protein, or a fragment thereof and stirring the resulting mixture.

In an exemplary embodiment, the phospholipid and the polydopamine nanoparticles may be mixed at a weight ratio (w/w) of 1 to 20:27, but the weight ratio is not limited thereto.

In another exemplary embodiment, the antibody or a fragment thereof; and the polydopamine nanoparticles may be mixed at a weight ratio (w/w) of 0.025 to 1:1, but the weight ratio is not limited thereto.

The present invention also provides a method for treating cancer, wherein the method includes administering, to a subject in need, a pharmaceutical composition for treating cancer, comprising a phospholipid-photothermal nanoparticle having an antibody bound to the surface thereof as an active ingredient.

The present invention also provides an immunotherapeutic method including administering, to a subject in need, a pharmaceutical composition for immunotherapy, comprising a phospholipid-photothermal nanoparticle having an antibody bound to the surface thereof as an active ingredient.

The present invention also provides a use of a composition for treating cancer, wherein the composition comprises a phospholipid-photothermal nanoparticle having an antibody bound to the surface thereof as an active ingredient.

The present invention also provides a use of a phospholipid-photothermal nanoparticle having an antibody bound to the surface thereof for preparing a drug for treating cancer.

The present invention also provides a use of a composition for immunotherapy, wherein the composition comprises a phospholipid-photothermal nanoparticle having an antibody bound to the surface thereof as an active ingredient.

The present invention also provides a use of a phospholipid-photothermal nanoparticle having an antibody bound to the surface thereof for preparing an immunotherapeutic drug.

Advantageous Effects

A phospholipid-photothermal nanoparticle according to the present invention has a cancer cell surface protein-specific antibody bound to the surface thereof, and thus can specifically bind to cancer cells, has a small particle size and excellent stability, and can effectively induce cancer cell apoptosis by exerting a photothermal effect when irradiated with near-infrared rays. Furthermore, the present inventors confirmed that when the antibody or a fragment thereof is site-specifically conjugated to the phospholipid-photothermal nanoparticle, the cancer cell binding ability and the photothermal cancer therapeutic effect of the phospholipid-photothermal nanoparticle are further improved. Therefore, it is expected that the phospholipid-photothermal nanoparticle having an antibody bound to the surface thereof according to the present invention will be advantageously utilized for cancer therapy.

MODES OF THE INVENTION

Figure 1:
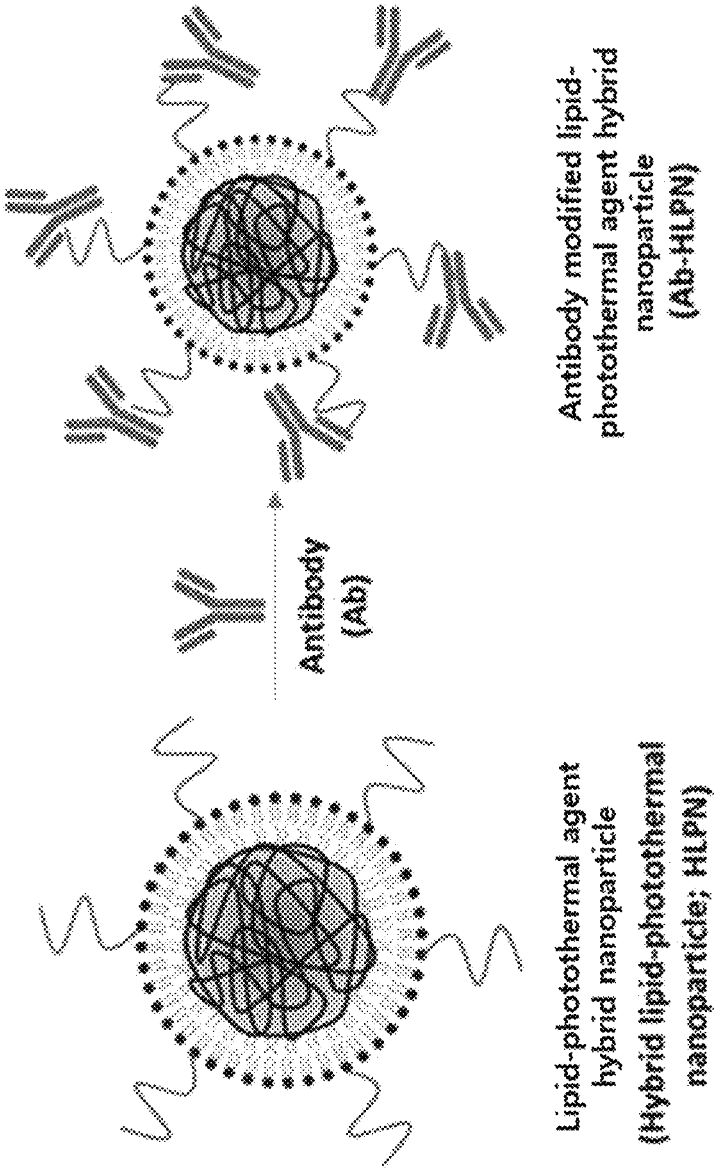
FIG. 1 illustrates a schematic view of a photothermal nanoparticle (hereinafter, referred to as Ab-HLPN), in which an antibody is bound to the end of PEGylated phospholipid on the surface of a hybrid lipid-photothermal nanoparticle (hereinafter, referred to as HLPN) of the present invention, and surrounded by a lipid layer.

The present invention provides a phospholipid-photothermal nanoparticle having an antibody bound to the surface thereof, including: a phospholipid membrane with entrapped photothermal nanoparticles; and an antibody specific for the surface protein of cancer cells, or a fragment thereof, which is bound to the surface of the phospholipid membrane.

In the present invention, the photothermal nanoparticle may be a polydopamine nanoparticle, a gold nanoparticle, a graphene nanosheet, or a melanin nanoparticle, but is not limited thereto. Preferably, the photothermal nanoparticle may be a polydopamine nanoparticle produced by self-polymerization of dopamine, which is a compound represented by the following Chemical Formula 1. The polydopamine nanoparticles may have a size of 10 to 500 nm, more preferably 50 to 200 nm.

[Chemical Formula 1]

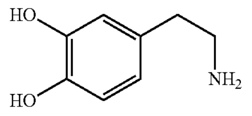

In the present invention, the photothermal nanoparticle may generate heat by absorbing light in the near-infrared region.

In the present invention, the phospholipid membrane may include any one or more selected from the group consisting of 1,2-dipalmitoyl-sn-glycero-3-phosphocholine (DPPC), 1,2-dipalmitoyl-sn-glycero-3-phosphoglycerol (DPPG), phosphoglycerol (PG), phosphocholine (PC) and 1,2-distearoyl-sn-glycero-3-phosphoethanolamine-N-[maleimide (polyethylene glycol)-2000] (DSPE-PEG2000-maleimide), but is not limited thereto. Preferably, the 1,2-dipalmitoyl-sn-glycero-3-phosphocholine (DPPC) may be represented by the following Chemical Formula 2, the 1,2-dipalmitoyl-sn-glycero-3-phosphoglycerol (DPPG) may be represented by the following Chemical Formula 3, the phosphoglycerol (PG) may be represented by Chemical Formula 4, the phosphocholine (PC) may be represented by Chemical Formula 5, and the 1,2-distearoyl-sn-glycero-3-phosphoethanolamine-N-[maleimide(polyethylene glycol)-2000] (DSPE-PEG2000-maleimide) may be represented by the following Chemical Formula 6.

[Chemical Formula 2]

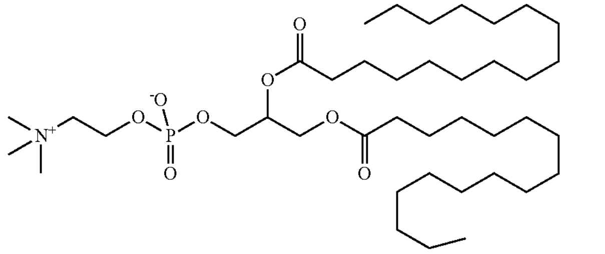

[Chemical Formula 3]

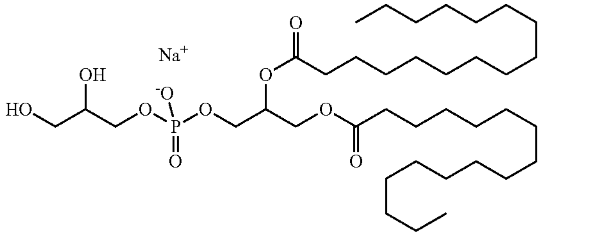

-continued

[Chemical Formula 4]

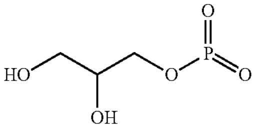

[Chemical Formula 5]

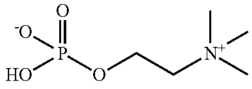

[Chemical Formula 6]

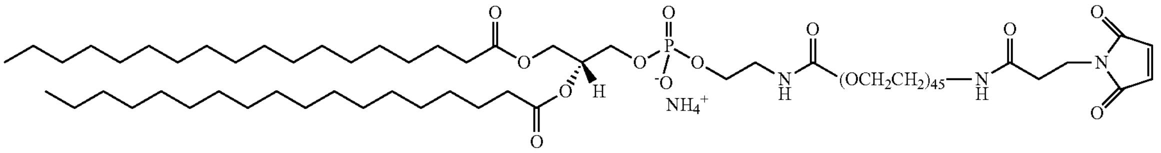

In the present invention, the 1,2-dipalmitoyl-sn-glycero-3-phosphocholine (DPPC) represented by Chemical Formula 2 and the 1,2-dipalmitoyl-sn-glycero-3-phosphoglycerol (DPPG) represented by Chemical Formula 3 may be mixed at a molar ratio of 5 to 9:1 to 5, preferably 6 to 8:2 to 4, and more preferably 6.5 to 7.5:2.5 to 3.5.

In the present invention, the antibody or a fragment thereof may bind to the surface end of a PEGylated phospholipid membrane.

In the present invention, 1,2-dipalmitoyl-sn-glycero-3-phosphocholine (DPPC), 1,2-dipalmitoyl-sn-glycero-3-phosphorylglycerol (DPPG), and 1,2-distearoyl-sn-glycero-3-phosphoethanolamine-N-[maleimide (polyethyleneglycol)-2000] (DSPE-PEG2000-maleimide) may be included at a molar ratio of 5 to 9:1 to 5:0.01 to 1, preferably 6 to 8:2 to 4:0.05 to 0.5, and more preferably 6.5 to 7.5:2.5 to 3.5:0.05 to 0.2.

In the present invention, the cancer cell surface protein may be Claudin3, HER2, or a prostate-specific membrane antigen (PSMA), but is not limited thereto. For example, the cancer cell surface protein Claudin3 may include an amino acid sequence of SEQ ID NO: 1, HER2 may include an amino acid sequence of SEQ ID NO: 2, and PSMA may include a sequence including an amino acid sequence of SEQ ID: 3. In addition to the above proteins, proteins expressed on the surface of cancer cells may be included without limitation.

In the present invention, the antibody or a fragment thereof specifically binds to the surface protein of cancer cells, and may be a compound, a peptide, a peptidomimetic, a substrate analogue, an aptamer, an antibody or an antibody fragment, preferably an antibody or an antibody fragment, but is not limited thereto.

As used herein, the term "antibody" refers to a specific protein molecule capable of specifically reacting with and binding to a specific antigen or an epitope site thereof, and includes an immunoglobulin molecule having an ability to bind to an antigen (for example, a monoclonal antibody, a polyclonal antibody, and the like), a fragment of the immunoglobulin molecule (for example, IgG, Fab', $F(ab')_2$, Fab, Fv, a recombinant IgG (rIgG), a single chain Fv (scFv), a diabody, and the like), and the like. In particular, the immunoglobulin molecule has a heavy chain and a light chain, each heavy chain and light chain including a constant region (site) and a variable region, and the light chain and heavy chain variable regions include three "complementarity determining regions (CDRs)" which are multivariable regions capable of binding to epitopes of an antibody; and four "framework regions (FRs)". The CDRs of each chain are typically referred to sequentially as CDR1, CDR2, and CDR3 starting from the N-end, and are identified by a chain on which a specific CDR is located. An intact antibody is a structure having two full-length light chains and two full-length heavy chains, and each light chain is linked to each heavy chain by a disulfide bond. The antibody may be an animal-derived antibody, a mouse-human chimeric antibody, a humanized antibody, or a human antibody.

In the present invention, the antibody or a fragment thereof can be included without limitation as long as it binds to a cancer cell-specific protein target, but specific examples thereof include an anti-Claudin3 antibody or a fragment thereof: an HER2 antibody (herceptin) or a fragment thereof: an anti-PSMA antibody or a fragment thereof; an EGFR antibody or a fragment thereof: an anti-ganglioside GD2 antibody or a fragment thereof.

Since Claudin3, HER2, or PSMA proteins are known proteins, the antibodies used in the present invention may be prepared using the proteins as antigens by typical methods widely known in the field of immunology. Claudin3, HER2, or PSMA proteins used as antigens of antibodies according to the present invention may be extracted from nature or synthesized, and may be prepared by recombinant methods based on DNA sequences. When a genetic recombination technique is used, the Claudin3, HER2, or PSMA proteins may be obtained by inserting nucleic acids encoding Claudin3, HER2, or PSMA proteins into appropriate expression vectors, culturing host cells so as to express Claudin3, HER2, or PSMA proteins in transformants transformed with recombinant expression vectors, and then recovering Claudin3, HER2, or PSMA proteins from the transformants.

For example, polyclonal antibodies may be produced by a method of obtaining an antibody-containing serum by injecting a Claudin3, HER2, or PSMA protein antigen into an animal and collecting blood from the animal. Such antibodies may be prepared using various warm-blooded animals such as horses, cows, goats, sheep, dogs, chickens, turkeys, rabbits, mice or rats.

Monoclonal antibodies may also be prepared using known fusion method (Kohler and Milstein, European J. Immunol. 6:511-519, 1976), recombinant DNA method (U.S. Pat. No. 4,816,567) and phage antibody library (Clackson et al., Nature, 352, 624-628, 1991: Marks et al., J. Mol. Biol. 222, 58:1-597, 1991) techniques.

More specifically, in the present invention, the anti-Claudin3 antibody or a fragment thereof can be included without limitation as long as it is any antibody or antibody fragment which can specifically bind to Claudin3, which is a cancer cell surface protein. For example, the anti-Claudin3 antibody or a fragment thereof may be an antibody that binds to a Claudin3 protein including an amino acid sequence of SEQ ID NO: 1, or a fragment thereof. Alternatively, the anti-Claudin3 antibody or a fragment thereof may include any one or more of amino acid sequences of SEQ ID NOS: 4 to 17. Specifically, the anti-Claudin3 antibody or a fragment thereof may include: a light chain variable region including any one or more of amino acid sequences of SEQ ID NOS: 4 to 7: a light chain constant region including an amino acid sequence of SEQ ID NO: 8: a heavy chain variable region including any one or more of amino acid sequences of SEQ ID NOS: 12 to 15; and/or a heavy chain constant region including an amino acid sequence of SEQ ID NO: 16. Alternatively, the anti-Claudin3 antibody or a fragment thereof may include: a light chain including an amino acid sequence of SEQ ID NO: 10; and/or a heavy chain including an amino acid sequence of SEQ ID NO: 17.

In the present invention, the herceptin or a fragment thereof can be included without limitation as long as it is any antibody or antibody fragment which can specifically bind to HER2, which is a cancer cell surface protein. For example, the herceptin or a fragment thereof may be an antibody that binds to an HER2 protein including an amino acid sequence of SEQ ID NO: 2, or a fragment thereof. Alternatively, the HER2 antibody or a fragment thereof may include any one or more of amino acid sequences of SEQ ID NOS: 18 to 29. Specifically, the HER2 antibody or a fragment thereof may include: a light chain variable region including any one or more of amino acid sequences of SEQ ID NOS: 18 to 21: a light chain constant region including an amino acid sequence of SEQ ID NO: 22: a heavy chain variable region including any one or more of amino acid sequences of SEQ ID NOS: 24 to 27; and/or a heavy chain constant region including an amino acid sequence of SEQ ID NO: 28. Alternatively, the HER2 antibody or a fragment thereof may include a light chain including an amino acid sequence of SEQ ID NO: 23 and/or a heavy chain including an amino acid sequence of SEQ ID NO: 29.

In the present invention, the anti-PSMA antibody or a fragment thereof can be included without limitation as long as it is any antibody or antibody fragment which can specifically bind to PSMA, which is a cancer cell surface protein. For example, the anti-PSMA antibody or a fragment thereof may be an antibody that binds to a PSMA protein including an amino acid sequence of SEQ ID NO: 3, or a fragment thereof. Alternatively, the anti-PSMA antibody or a fragment thereof may include any one or more of amino acid sequences of SEQ ID NOS: 30 to 41. Specifically, the anti-PSMA antibody or a fragment thereof may include: a light chain variable region including any one or more of amino acid sequences of SEQ ID NOS: 30 to 33; a light chain constant region including an amino acid sequence of SEQ ID NO: 34; a heavy chain variable region including any one or more of amino acid sequences of SEQ ID NOS: 36 to 39; and/or a heavy chain constant region including an amino acid sequence of SEQ ID NO: 40. Alternatively, the anti-PSMA antibody or a fragment thereof may include a light chain including an amino acid sequence of SEQ ID NO: 35 and/or a heavy chain including an amino acid sequence of SEQ ID NO: 41.

In the present specification, a protein including an amino acid sequence of a specific sequence number may include an amino acid sequence of the corresponding sequence number or consist of an amino acid sequence of the corresponding sequence number, and a variant sequence in which functional equivalents thereof, for example, some nucleotide sequences are modified by deletion, substitution, or insertion, but expression products can perform functionally the same action. That is, the protein including the amino acid sequence of the specific sequence number may include an amino acid sequence having a sequence homology of 80% or more, more preferably 90% or more, and even more preferably 95% or more with the amino acid sequence of the corresponding sequence number, or consist of an amino acid having the sequence homology. For example, the protein including the amino acid sequence of the specific sequence number, and the like may include an amino acid sequence having a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% with the amino acid sequence represented by the corresponding sequence number, or consist of an amino acid sequence having the sequence homology.

In the present invention, the antibody or a fragment thereof may be modified so as to have a free thiol group, and the phospholipid membrane may include a phospholipid to which maleimide is bound. Preferably, the free thiol group may be present in the constant region (site) of the light chain of the antibody or a fragment thereof, but is not limited thereto. Preferably, the phospholipid to which maleimide is bound may be 1,2-distearoyl-sn-glycero-3-phosphoethanolamine-N-[maleimide(polyethyleneglycol)-2000] (DSPE-PEG2000-maleimide), but is not limited thereto.

In the present invention, the antibody or a fragment thereof may be an anti-Claudin3 antibody modified so as to have a free thiol group, or a fragment thereof. That is, the modified anti-Claudin3 antibody or a fragment thereof is modified such that the anti-Claudin3 antibody includes a free thiol group, and may be an anti-Claudin3 antibody on the cancer cell surface, and the modification includes both a natural modification and an artificial modification.

For example, the modified anti-Claudin3 antibody or a fragment thereof may include an amino acid sequence of SEQ ID NO: 9, in which the 17 glutamine residue in an amino acid sequence of SEQ ID NO: 8 is substituted with a cysteine residue. More specifically, the anti-Claudin3 antibody modified so as to have the free thiol group, or a fragment thereof may include a light chain constant region including an amino acid sequence of SEQ ID NO: 9, in which the 17 glutamine residue in an amino acid sequence of SEQ ID NO: 8 is substituted with a cysteine residue.

More specifically, the modified anti-Claudin3 antibody or a fragment thereof may include an amino acid sequence of SEQ ID NO: 11, in which the 125 glutamine residue in an amino acid sequence of SEQ ID NO: 10 is substituted with a cysteine residue. Alternatively, the anti-Claudin3 antibody modified so as to have the free thiol group, or a fragment thereof may include a light chain including an amino acid sequence of SEQ ID NO: 11, in which the 125 glutamine residue in an amino acid sequence of SEQ ID NO: 10 is substituted with a cysteine residue.

In the present specification, the anti-Claudin3 antibody including: a light chain constant region consisting of an amino acid sequence of SEQ ID NO: 8; or a light chain consisting of an amino acid sequence of SEQ ID NO: 10 may be referred to as h4G3, and the anti-Claudin3 antibody modified so as to have a free thiol group, including: a light chain constant region consisting of an amino acid sequence of SEQ ID NO: 9; or a light chain consisting of an amino acid sequence of SEQ ID NO: 11 may be referred to as h4G3cys.

Further, the anti-Claudin3 antibody modified so as to have a free thiol group, or a fragment thereof may include: a light chain variable region including any one or more of amino acid sequences of SEQ ID NOS: 4 to 7; and/or a heavy chain variable region including any one or more of amino acid sequences of SEQ ID NOS: 12 to 15. Specifically, the anti-Claudin3 antibody modified so as to have a free thiol group, or a fragment thereof may include a light chain variable region including: a light chain CDR1 including an amino acid sequence of SEQ ID NO: 4; a light chain CDR2 including an amino acid sequence of SEQ ID NO: 5; and a light chain CDR3 including an amino acid sequence of SEQ ID NO: 6. Alternatively, the anti-Claudin3 antibody modified so as to have a free thiol group, or a fragment thereof may include a heavy chain variable region including: a heavy chain CDR1 including an amino acid sequence of SEQ ID NO: 12; a heavy chain CDR2 including an amino acid sequence of SEQ ID NO: 13; and a heavy chain CDR3 including an amino acid sequence of SEQ ID NO: 14. Alternatively, the anti-Claudin3 antibody modified so as to have a free thiol group, or a fragment thereof may include a light chain variable region including an amino acid sequence of SEQ ID NO: 7 and/or a heavy chain variable region including an amino acid sequence of SEQ ID NO: 15.

In addition, the anti-Claudin3 antibody modified so as to have a free thiol group, or a fragment thereof may include a heavy chain constant region of SEQ ID NO: 16.

Furthermore, the anti-Claudin3 antibody modified so as to have a free thiol group, or a fragment thereof may include a heavy chain including an amino acid sequence of SEQ ID NO: 17.

In the present specification, the site-specific conjugation means a bond between an antibody and a linker of phospholipid-photothermal nanoparticles. For example, the site-specific conjugation may mean a bond between the free thiol group of the antibody and the maleimide bound to the phospholipid of phospholipid-photothermal nanoparticles.

In the present invention, when the photothermal nanoparticles are polydopamine nanoparticles, phospholipid and polydopamine nanoparticles (PNs) may be included at a weight ratio (w/w) of 1 to 20:27, preferably at a weight ratio (w/w) of 5 to 15:27, and more preferably at a weight ratio (w/w) of 7 to 12:27. Most preferably, phospholipid: polydopamine may be included at a weight ratio (w/w) of 10:27.

Further, in the present invention, when the photothermal nanoparticles are polydopamine nanoparticles, the weight ratio (w/w) of the antibody or a fragment thereof; and polydopamine nanoparticles may be 0.025 to 1:1, preferably 0.1 to 1:1, more preferably 0.3 to 0.7:1, and even more preferably 0.4 to 0.6:1 (w/w). Most preferably, the weight ratio (w/w) of the antibody or a fragment thereof; and polydopamine nanoparticles may be 0.5:1 (w/w).

The phospholipid-photothermal nanoparticle having the antibody or a fragment thereof bound to the surface thereof may have a particle size of 50 to 300 nm, preferably a particle size of 100 to 250 nm, and more preferably a particle size of 120 to 200 nm.

In addition, the present invention provides a method for preparing a phospholipid-photothermal nanoparticle having an antibody bound to the surface thereof, the method including: (1) preparing polydopamine nanoparticles by mixing a dopamine hydrochloride solution with a sodium hydroxide solution; (2) preparing a phospholipid membrane by dissolving any one or more phospholipids selected from the group consisting of 1,2-dipalmitoyl-sn-glycero-3-phosphocholine (DPPC), 1,2-dipalmitoyl-sn-glycero-3-phosphorylglycerol (DPPG), phosphorylglycerol (PG), phosphocholine (PC) and 1,2-distearoyl-sn-glycero-3-phosphoethanolamine-N-[maleimide(polyethyleneglycol)-2000] (DSPE-PEG2000-maleimide) in an organic solvent and concentrating the resulting solution under reduced pressure; (3) hydrating the phospholipid membrane prepared in Step (2) by adding the polydopamine nanoparticles prepared in Step (1) to the phospholipid membrane; and (4) adding an antibody capable of binding to a cancer cell surface protein, or a fragment thereof and stirring the resulting mixture.

The pH of the mixture of the dopamine hydrochloride solution and the sodium hydroxide solution in Step (1) may be pH 8 to 11, preferably pH 9 to 10.5, and more preferably pH 9.5 to 10.

Step (1) may be performed at 40 to 60° C., preferably 45 to 55° C., and more preferably 47 to 52° C.

The organic solvent may be any one or more selected from the group consisting of chloroform, hexane, ethyl acetate, methanol, dichloromethane, carbon tetrachloride, benzene, DMSO and DMF, may be preferably chloroform and methanol, but is not limited thereto.

The chloroform and the methanol may be mixed at a volume ratio of 1 to 7:0.1 to 2, and at a volume ratio of preferably 3 to 5:0.5 to 1.5.

The 1,2-dipalmitoyl-sn-glycero-3-phosphocholine (DPPC) and the 1,2-dipalmitoyl-sn-glycero-3-phosphoglycerol (DPPG) may be mixed at a molar ratio of 5 to 9:1 to 5, preferably 6 to 8:2 to 4, and more preferably 6.5 to 7.5:2.5 to 3.5.

Alternatively, 1,2-dipalmitoyl-sn-glycero-3-phosphocholine (DPPC), 1,2-dipalmitoyl-sn-glycero-3-phosphorylglycerol (DPPG), and 1,2-distearoyl-sn-glycero-3-phosphoethanolamine-N-[maleimide(polyethyleneglycol)-2000] (DSPE-PEG2000-maleimide) may be included at a molar ratio of 5 to 9:1 to 5:0.01 to 1, preferably 6 to 8:2 to 4:0.05 to 0.5, and more preferably 6.5 to 7.5:2.5 to 3.5:0.05 to 0.2.

Furthermore, the phospholipid and polydopamine nanoparticles (PNs) may be mixed at a weight ratio (w/w) of 1 to 20:27, preferably at a weight ratio (w/w) of 5 to 15:27, and more preferably at a weight ratio (w/w) of 7 to 12:27.

Step (4) may be performed at 1 to 10° C., preferably 2 to 6° C., and more preferably 3 to 5° C.

Further, the antibody or a fragment thereof; and polydopamine may be mixed at a weight ratio (w/w) of 0.025 to 1:1, preferably at a weight ratio (w/w) of 0.1 to 1:1, more preferably at a weight ratio of 0.3 to 0.7:1, and even more preferably at a weight ratio of 0.4 to 0.6:1.

In addition, the antibody or a fragment thereof may be modified so as to have a free thiol group, and may be preferably an anti-Claudin3 antibody modified so as to have a free thiol group, or a fragment thereof.

The phospholipid-photothermal nanoparticle having the antibody bound to the surface thereof may have a particle size of 50 to 300 nm, preferably a particle size of 100 to 250 nm, and more preferably a particle size of 120 to 200 nm.

Furthermore, the present invention provides a pharmaceutical composition for treating cancer, including a phospholipid-photothermal nanoparticle having an antibody or a fragment thereof bound to the surface thereof as an active ingredient.

Further, the present invention provides a pharmaceutical composition for cancer immunotherapy, including a phospholipid-photothermal nanoparticle having an antibody or a fragment thereof bound to the surface thereof as an active ingredient.

The cancer may be a solid cancer or a hematological cancer. Specifically, the solid cancer may be brain tumors, pilocytic astrocytoma, anaplastic astrocytoma, pituitary adenoma, meningioma, brain lymphoma, oligodendroglioma, craniopharyngioma, ependymoma, brain stem tumors, head and neck tumors, laryngeal cancer, oropharyngeal cancer, nasal cavity cancer, nasopharyngeal cancer, salivary gland cancer, hypopharyngeal cancer, thyroid cancer, oral cancer, chest tumors, small cell lung cancer, non-small cell lung cancer, thymus cancer, mediastinal tumors, esophageal cancer, breast cancer, male breast cancer, abdominal tumors, gastric cancer, liver cancer, gallbladder cancer, biliary tract cancer, pancreatic cancer, small bowel cancer, colorectal cancer, anal cancer, bladder cancer, renal cancer, male genital tumors, penile cancer, prostate cancer, female genital tumors, cervical cancer, endometrial cancer, ovarian cancer, uterine sarcoma, vaginal cancer, vulva cancer, female urethral cancer, skin cancer, or the like, and the hematological cancer may be leukemia, malignant lymphoma, multiple myeloma, anemia aplastic, or the like. Preferably, the cancer may be a cancer expressing Claudin3. Specifically, the cancer may be ovarian cancer, gastric cancer, colorectal cancer, prostate cancer, pancreatic cancer, and the like.

The photothermal nanoparticles induce the death of cancer cells upon irradiation with therapeutically effective light.

The content of the phospholipid-photothermal nanoparticle having the antibody bound to the surface thereof (Ab-HLPN) in the composition of the present invention can be appropriately adjusted according to the symptoms of the disease, the degree of progression of the symptoms, the condition of the patient, and the like, and may be, for example, 0.0001 to 99.9 wt %, or 0.001 to 50 wt % based on the total weight of the composition, but is not limited thereto. The content ratio is a value based on a dry amount from which the solvent is removed.

The pharmaceutical composition of the present invention may further include an appropriate carrier, an appropriate excipient, and an appropriate diluent, which are typically used to prepare a pharmaceutical composition. The excipient may be, for example, one or more selected from the group consisting of a diluent, a binder, a disintegrant, a lubricant, an adsorbent, a moisturizer, a film-coating material, and a controlled release additive.

The pharmaceutical composition according to the present invention may be used by being formulated into the form of an external preparation such as a powder, a granule, a sustained-release granule, an enteric granule, a liquid, a collyrium, an elixir, an emulsion, a suspension, a spirit, a troche, aromatic water, a limonade, a tablet, a sustained-release tablet, an enteric tablet, a sublingual tablet, a hard capsule, a soft capsule, a sustained-release capsule, an enteric capsule, a pill, a tincture, a soft extract agent, a dry extract agent, a fluid extract agent, an injection, a capsule, a perfusate, a plaster, a lotion, a paste, a spray, an inhalant, a patch, a sterilized injection solution, or an aerosol, and the external preparation may have a formulation such as a cream, a gel, a patch, a spray, an ointment, a plaster, a lotion, a liniment, a paste or a cataplasma.

Examples of a carrier, an excipient or a diluent which may be included in the composition according to the present invention include lactose, dextrose, sucrose, an oligosaccharide, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

When the pharmaceutical composition is prepared, the pharmaceutical composition is prepared using a diluent or excipient, such as a filler, an extender, a binder, a wetting agent, a disintegrant, and a surfactant, which are commonly used.

As an additive of the tablet, powder, granule, capsule, pill, and troche according to the present invention, it is possible to use an excipient such as corn starch, potato starch, wheat starch, lactose, white sugar, glucose, fructose, D-mannitol, precipitated calcium carbonate, synthetic aluminum silicate, calcium monohydrogen phosphate, calcium sulfate, sodium chloride, sodium hydrogen carbonate, purified lanolin, microcrystalline cellulose, dextrin, sodium alginate, methyl cellulose, carboxymethyl cellulose sodium, kaolin, urea, colloidal silica gel, hydroxypropyl starch, hydroxypropyl methylcellulose (HPMC) 1928, HPMC 2208, HPMC 2906, HPMC 2910, propylene glycol, casein, calcium lactate, and Primojel; and a binder such as gelatin, arabic gum, ethanol, agar powder, cellulose acetate phthalate, carboxymethyl cellulose, carboxymethyl cellulose calcium, glucose, purified water, sodium caseinate, glycerin, stearic acid, carboxymethyl cellulose sodium, methylcellulose sodium, methylcellulose, microcrystalline cellulose, dextrin, hydroxycellulose, hydroxypropyl starch, hydroxymethyl cellulose, purified shellac, starch, hydroxypropyl cellulose, hydroxypropyl methyl cellulose, polyvinyl alcohol, and polyvinylpyrrolidone, and it is possible to use a disintegrant such as hydroxypropyl methyl cellulose, corn starch, agar powder, methyl cellulose, bentonite, hydroxypropyl starch, carboxymethyl cellulose sodium, sodium alginate, carboxymethyl cellulose calcium, calcium citrate, sodium lauryl sulfate, silicic anhydride, 1-hydroxypropyl cellulose, dextran, an ion exchange resin, polyvinyl acetate, formaldehyde-treated casein and gelatin, alginic acid, amylose, guar gum, sodium bicarbonate, polyvinylpyrrolidone, calcium phosphate, gelled starch, arabic gum, amylopectin, pectin, sodium polyphosphate, ethyl cellulose, white sugar, magnesium aluminum silicate, a D-sorbitol solution, and light anhydrous silicic acid; and a lubricant such as calcium stearate, magnesium stearate, stearic acid, hydrogenated vegetable oil, talc, lycopodium powder, kaolin, Vaseline, sodium stearate, cacao butter, sodium salicylate, magnesium salicylate, polyethylene glycol (PEG) 4000, PEG 6000, liquid paraffin, hydrogenated soybean oil (Lubriwax), aluminum stearate, zinc stearate, sodium lauryl sulfate, magnesium oxide, Macrogol, synthetic aluminum silicate, silicic anhydride, higher fatty acids, higher alcohols, silicone oil, paraffin oil, polyethylene glycol fatty acid ether, starch, sodium chloride, sodium acetate, sodium oleate, dl-leucine, and light anhydrous silicic acid.

As an additive for liquid formulation according to the present invention, it is possible to use water, diluted hydrochloric acid, diluted sulfuric acid, sodium citrate, sucrose monostearates, polyoxyethylene sorbitol fatty acid esters (Tween esters), polyoxyethylene monoalkyl ethers, lanolin ethers, lanolin esters, acetic acid, hydrochloric acid, aqueous ammonia, ammonium carbonate, potassium hydroxide, sodium hydroxide, prolamin, polyvinyl pyrrolidone, ethyl cellulose, carboxymethyl cellulose sodium, and the like.

In a syrup according to the present invention, a solution of sucrose, other sugars or sweeteners, and the like may be used, and a fragrance, a colorant, a preservative, a stabilizer, a suspending agent, an emulsifier, a thickener, and the like may be used, if necessary.

Purified water may be used for the emulsion according to the present invention, and an emulsifier, a preservative, a stabilizer, a fragrance, and the like may be used, if necessary.

In the suspending agent according to the present invention, a suspending agent such as acacia, tragacanth, methyl cellulose, carboxymethyl cellulose, carboxymethyl cellulose sodium, microcrystalline cellulose, sodium alginate, hydroxypropyl methyl cellulose, HPMC 1828, HPMC 2906, and HPMC 2910 may be used, and a surfactant, a preservative, a colorant, and a fragrance may be used, if necessary.

The injection according to the present invention may include: a solvent such as distilled water for injection, 0.9% sodium chloride injection, Ringer's injection, dextrose injection, dextrose+sodium chloride injection, PEG, lactated Ringer's injection, ethanol, propylene glycol, non-volatile oil-sesame oil, cottonseed oil, peanut oil, corn oil, ethyl oleate, isopropyl myristate, and benzoic acid benzene: a solubilizing aid such as sodium benzoate, sodium salicylate, sodium acetate, urea, urethane, monoethyl acetamide, butazolidin, propylene glycol, Tweens, nijungtinateamide, hexamine, and dimethylacetamide: a buffer such as a weak acid and a salt thereof (acetic acid and sodium acetate), a weak base and a salt thereof (ammonia and ammonium acetate), an organic compound, a protein, albumin, peptone, and gums: an isotonic agent such as sodium chloride; a stabilizer such as sodium bisulfite ($NaHSO_3$), carbon dioxide gas, sodium metabisulfite ($Na_2S_2O_5$), sodium sulfite ($Na_2SO_3$), nitrogen gas ($N_2$), and ethylenediaminetetraacetic acid; an antioxidant such as 0.1% sodium bisulfide, sodium formaldehydesulfoxylate, thiourea, disodium ethylenediaminetetraacetate, and acetone sodium bisulfite: an analgesic such as benzyl alcohol, chlorobutanol, procaine hydrochloride, glucose, and calcium gluconate; and a suspending agent such as carboxymethyl cellulose sodium, sodium alginate, Tween 80, and aluminum monostearate.

In a suppository according to the present invention, it is possible to use a base such as cacao butter, lanolin, Witepsol, polyethylene glycol, glycerogelatin, methylcellulose, carboxymethyl cellulose, a mixture of stearic acid and oleic acid, Subanal, cottonseed oil, peanut oil, palm oil, cacao butter+cholesterol, lecithin, ranetwax, glycerol monostearate, Tween or Span, Imhausen, monolen (propylene glycol monostearate), glycerin, Adeps solidus, Buytyrum Tego-G, Cebes Pharma 16, hexalide base 95, Cotomar, Hydroxote SP, S-70-XXA, S-70-XX75(S-70-XX95), Hydrokote 25, Hydrokote 711, idropostal, Massa estrarium (A, AS, B, C, D, E, I, T), Massa-MF, Masupol, Masupol-15, Neosupostalene, Paramound-B, Suposhiro (OSI, OSIX, A, B, C, D, H, L), suppository base IV types (AB, B, A, BC, BBG, E, BGF, C, D, 299), Supostal (N, Es), Wecobee (W, R, S, M, Fs), and tegester triglyceride base (TG-95, MA, 57).

A solid formulation for oral administration includes a tablet, a pill, a powder, a granule, a capsule, and the like, and the solid formulation is prepared by mixing at least one excipient, for example, starch, calcium carbonate, sucrose or lactose, gelatin, and the like with the extract. Further, in addition to a simple excipient, lubricants such as magnesium stearate and talc are also used.

A liquid formulation for oral administration corresponds to a suspension, a liquid for internal use, an emulsion, a syrup, and the like, and the liquid formulation may include, in addition to water and liquid paraffin which are simple commonly used diluents, various excipients, for example, a wetting agent, a sweetener, a fragrance, a preservative, and the like. Examples of a formulation for parenteral administration include an aqueous sterile solution, a non-aqueous solvent, a suspension, an emulsion, a freeze-dried preparation, and a suppository. As the non-aqueous solvent and the suspension, it is possible to use propylene glycol, polyethylene glycol, a vegetable oil such as olive oil, an injectable ester such as ethyl oleate, and the like.

The pharmaceutical composition according to the present invention is administered in a pharmaceutically effective amount. In the present invention, "pharmaceutically effective amount" means an amount sufficient to treat diseases at a reasonable benefit/risk ratio applicable to medical treatment, and an effective dosage level may be determined according to factors including the type of disease of patients, the severity of disease, the activity of drugs, sensitivity to drugs, administration time, administration route, excretion rate, treatment period, and simultaneously used drugs, and other factors well known in the medical field.

The pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by a person with ordinary skill in the art to which the present invention pertains.

The pharmaceutical composition of the present invention may be administered to a subject in need via various routes. All methods of administration may be expected, but the pharmaceutical composition may be administered by, for example, oral administration, subcutaneous injection, peritoneal administration, intravenous injection, intramuscular injection, paraspinal space (intradural) injection, sublingual administration, buccal administration, intrarectal insertion, intravaginal injection, ocular administration, ear administration, nasal administration, inhalation, spray via the mouth or nose, skin administration, transdermal administration, and the like.

The pharmaceutical composition of the present invention is determined by the type of drug that is an active ingredient, as well as various related factors such as the disease to be treated, the route of administration, the age, sex, and body weight of a patient, and the severity of the disease.

As used herein, the "individual" refers to a subject in need of treatment of a disease, and more specifically, refers to a mammal such as a human or a non-human primate, a mouse, a rat, a dog, a cat, a horse, and a cow.

The "administration" as used herein refers to the provision of a predetermined composition of the present invention to a subject in need thereof by any suitable method.

As used herein, the "prevention" refers to all actions that suppress or delay the onset of a target disease, and the "treatment" refers to all actions that ameliorate or beneficially change a target disease and the resulting metabolic abnormalities by administration of the pharmaceutical composition according to the present invention, and the "amelioration" refers to all actions that reduce a target disease and associated parameters, for example, the severity of symptoms, by administration of the composition according to the present invention.

The cancer treatment method or immunotherapy method according to the present invention may be particularly suitable for patients with increased expression of Claudin3, HER2 and/or PSMA.

Hereinafter, examples of the present invention will be briefly described.

In specific exemplary embodiment of the present invention, the present inventors prepared phospholipid-photothermal nanoparticles having antibodies including phospholipids of various compositions (Compositions 1 to 7) bound to the surfaces thereof.

Figure 2:
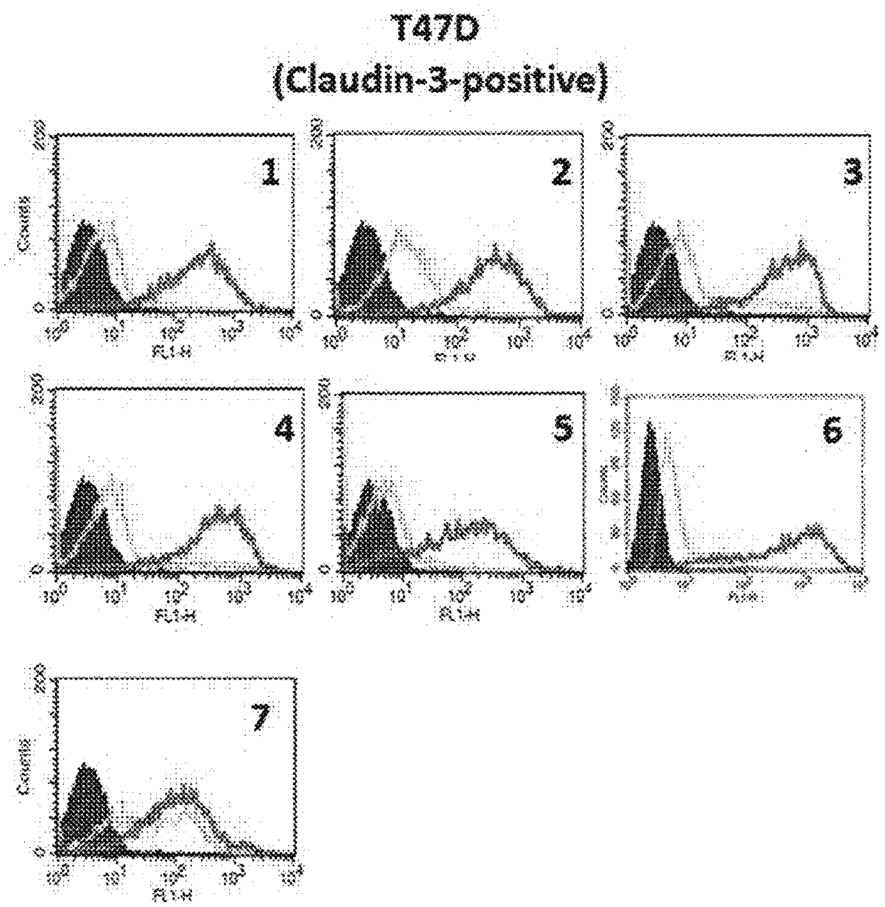
FIG. 2 illustrates the measurement of the ability of 7 types of Claudin3 Ab-HLPN with different phospholipid compositions to bind to Claudin3-overexpressing cancer cells by flow cytometry, and is a set of views confirming that Ab-HLPN containing phospholipids of Compositions 1 to 6 binds well to Claudin3-overexpressing cancer cells.
Figure 3:
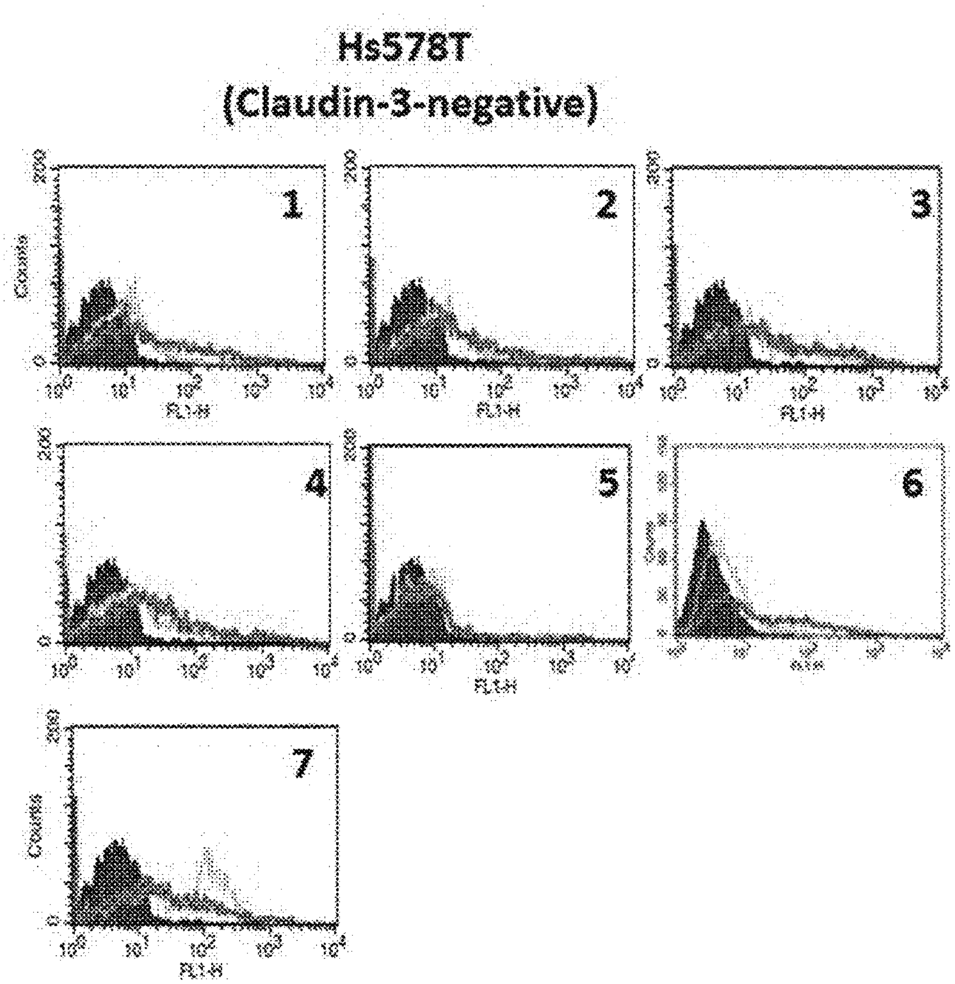
FIG. 3 illustrates the measurement of the ability of 7 types of Claudin3 Ab-HLPN with different phospholipid compositions to bind to Claudin3-non-expressing cancer cells by flow cytometry, and is a set of views confirming that Ab-HLPN containing phospholipids of Compositions 1 to 7 does not bind to Claudin3-non-expressing cancer cells.

In addition, the present inventors confirmed that the phospholipid-photothermal nanoparticle having antibodies including phospholipids of Compositions 1 to 6 among Compositions 1 to 7 bound to the surfaces thereof bind well to Claudin3-overexpressing cells, but not to Claudin3-non-expressing cells (FIGS. 2 and 3).

Figure 4:
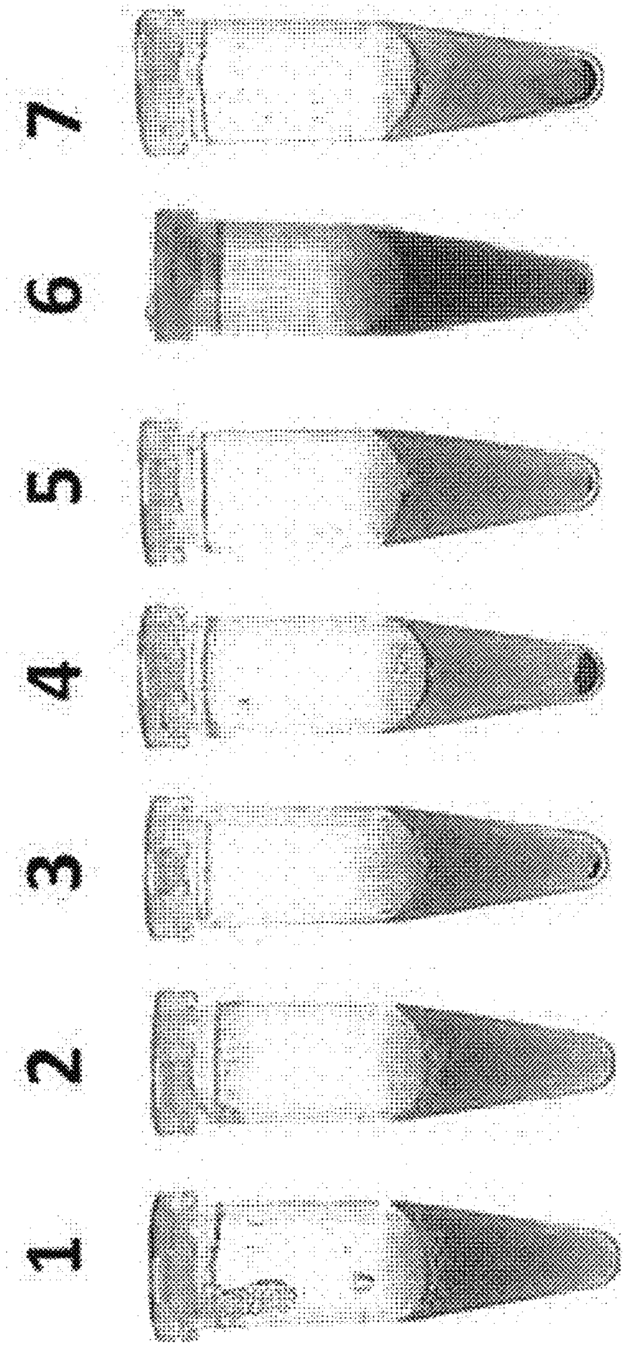
FIG. 4 is a view illustrating the stability observations of 7 types of Ab-HLPN with different phospholipid compositions.

Furthermore, by confirming that nanoparticles including the phospholipid of Composition 1 among Compositions 1 to 7 have the highest stability and a small particle size, a phospholipid-photothermal nanoparticle having an antibody including the phospholipid of Composition 1 bound to the surface thereof was selected (FIG. 4 and Table 1).

Figure 5:
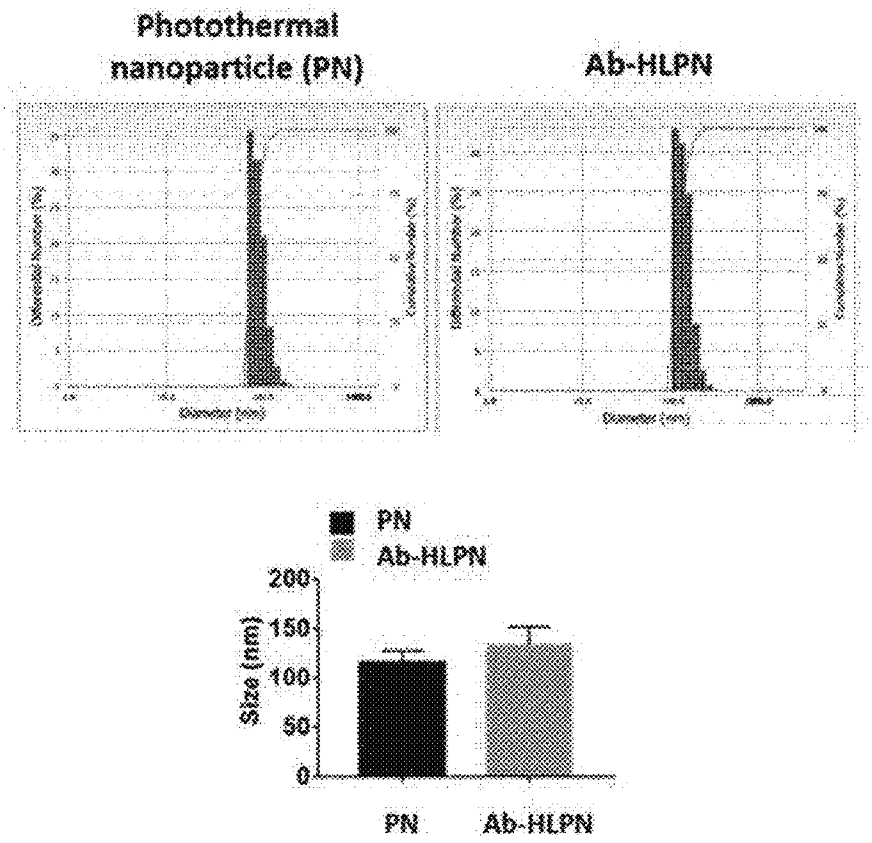
FIG. 5 illustrates the measurement of the particle size distributions of a photothermal nanoparticle (hereinafter, referred to as PN) and Ab-HLPN having a phospholipid composition of Composition 1 by dynamic light scattering, and is a set of views confirming that there was almost no difference in particle size.
Figure 6:
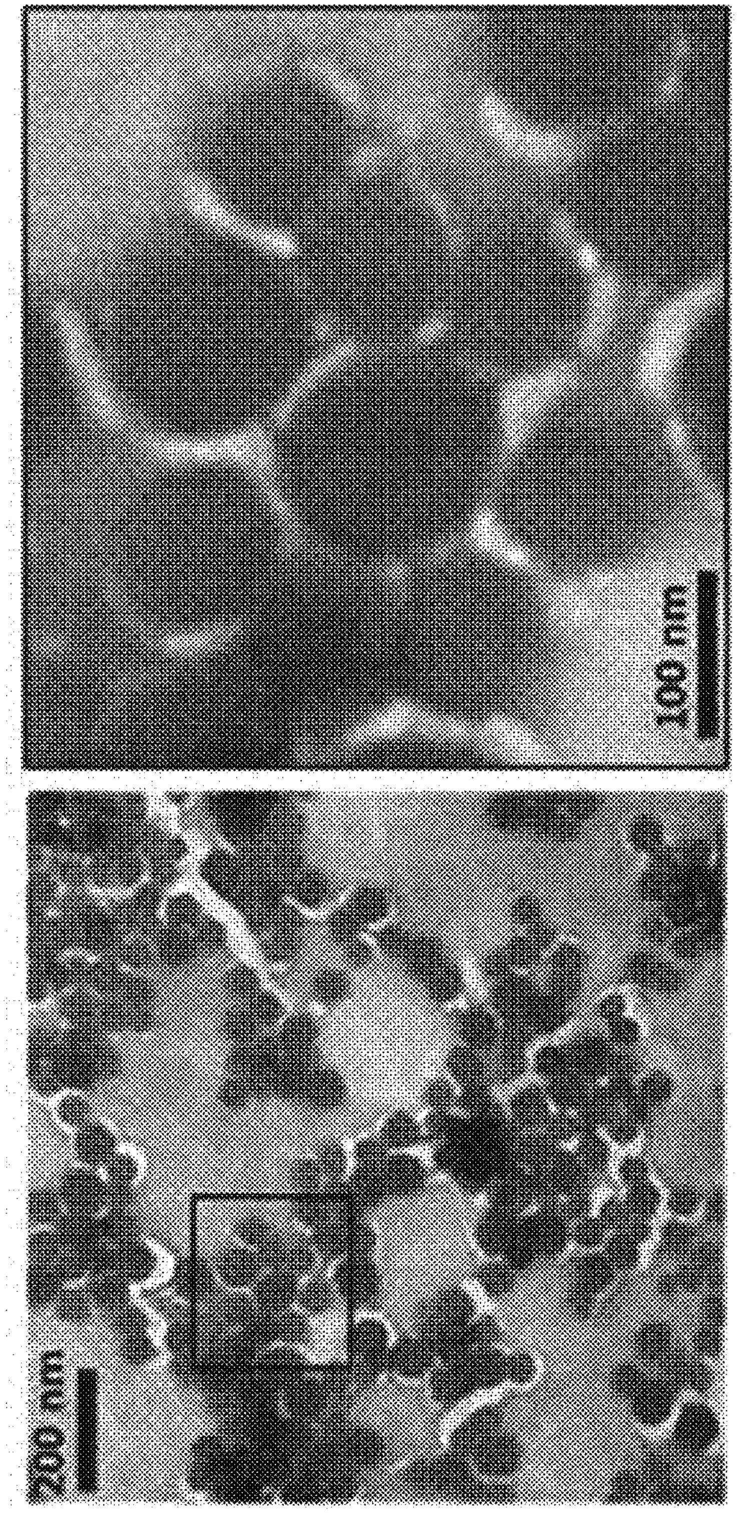
FIG. 6 is a set of photographs of Ab-HLPN having a phospholipid composition of Composition 1 taken by a transmission electron microscope (TEM).

Further, it was confirmed that the average particle size of the nanoparticle including the phospholipid of Composition 1 was slightly increased compared to the polydopamine nanoparticle (FIG. 5), and it was confirmed that for the morphology of the particle, a morphology in which the polydopamine nanoparticles are surrounded by a lipid thin layer was also observed (FIG. 6).

Figure 7:
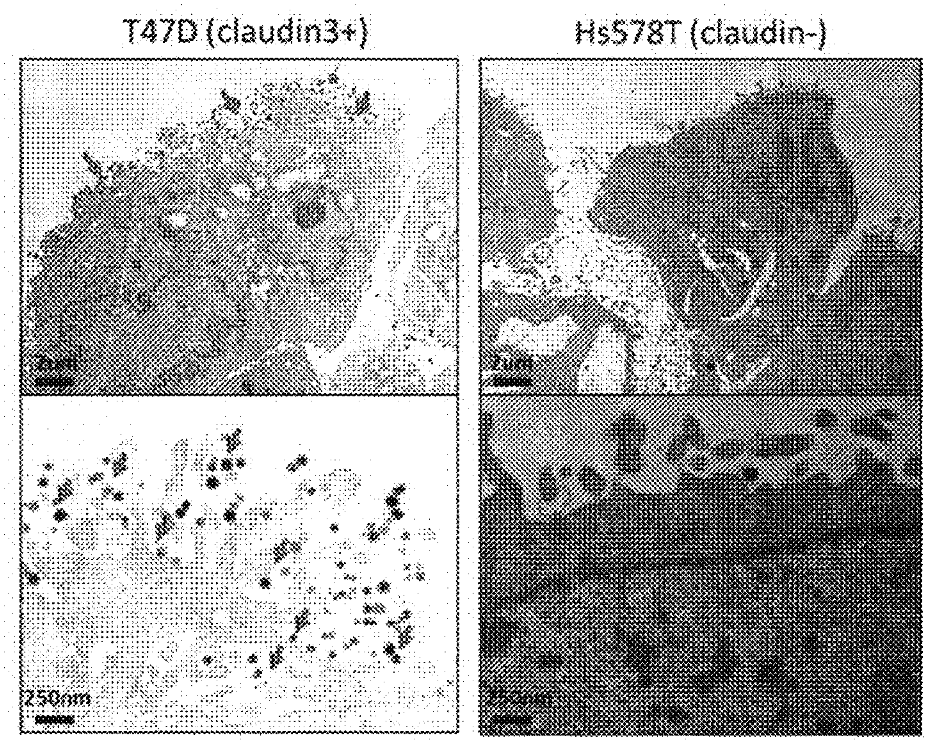
FIG. 7 illustrates the measurement of the ability of Claudin3 Ab-HLPN having a phospholipid composition of Composition 1 to bind to cancer cells by a transmission electron microscope, and is a set of views confirming that the Claudin3 Ab-HLPN of the present invention specifically binds to Claudin-3-overexpressing cells.
Figure 8:
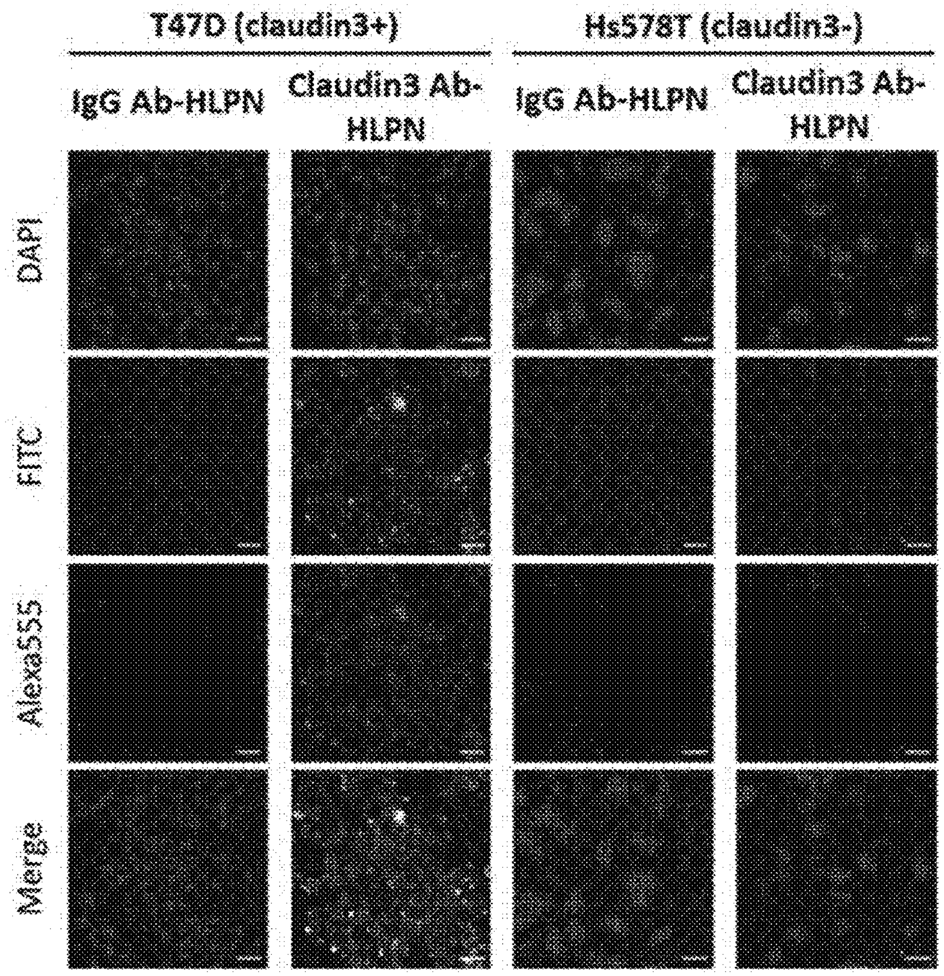
FIG. 8 illustrates the measurement of the ability of Claudin3 Ab-HLPN having a phospholipid composition of Composition 1 to bind to cancer cells by a confocal fluorescence microscope, and is a set of views confirming that the Claudin3 Ab-HLPN of the present invention specifically binds well to Claudin-3-overexpressing cells, and does not bind to Claudin3-non-expressing cells.

In addition, it was confirmed that the nanoparticles including the phospholipid of Composition 1 have remarkably higher ability to bind to Claudin3-overexpressing cancer cells than to Claudin3-non-expressing cancer cells (FIGS. 7 and 8).

Figure 9:
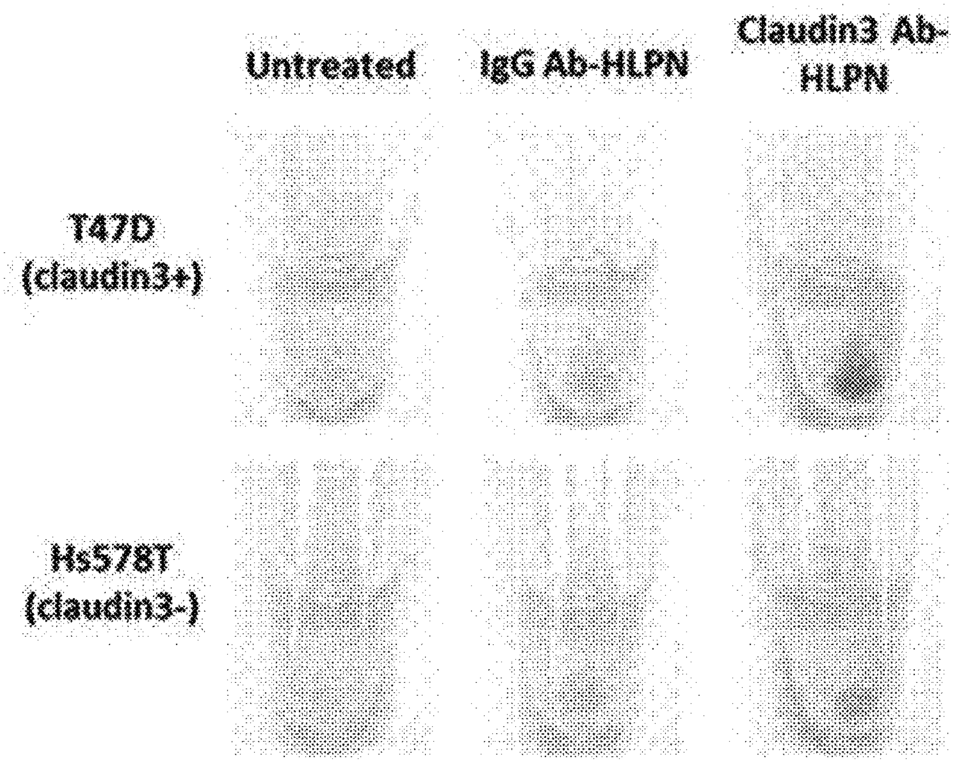
FIG. 9 illustrates the ability of Claudin3 Ab-HLPN to bind to cancer cells by observing the colors of cell pellets, and is a view confirming that Claudin3 Ab-HLPN having a phospholipid composition of Composition 1 can induce a photothermal effect in cancer cells expressing Claudin by observing the dark colors of cell pellets in Claudin3-overexpressing calls.
Figure 10:
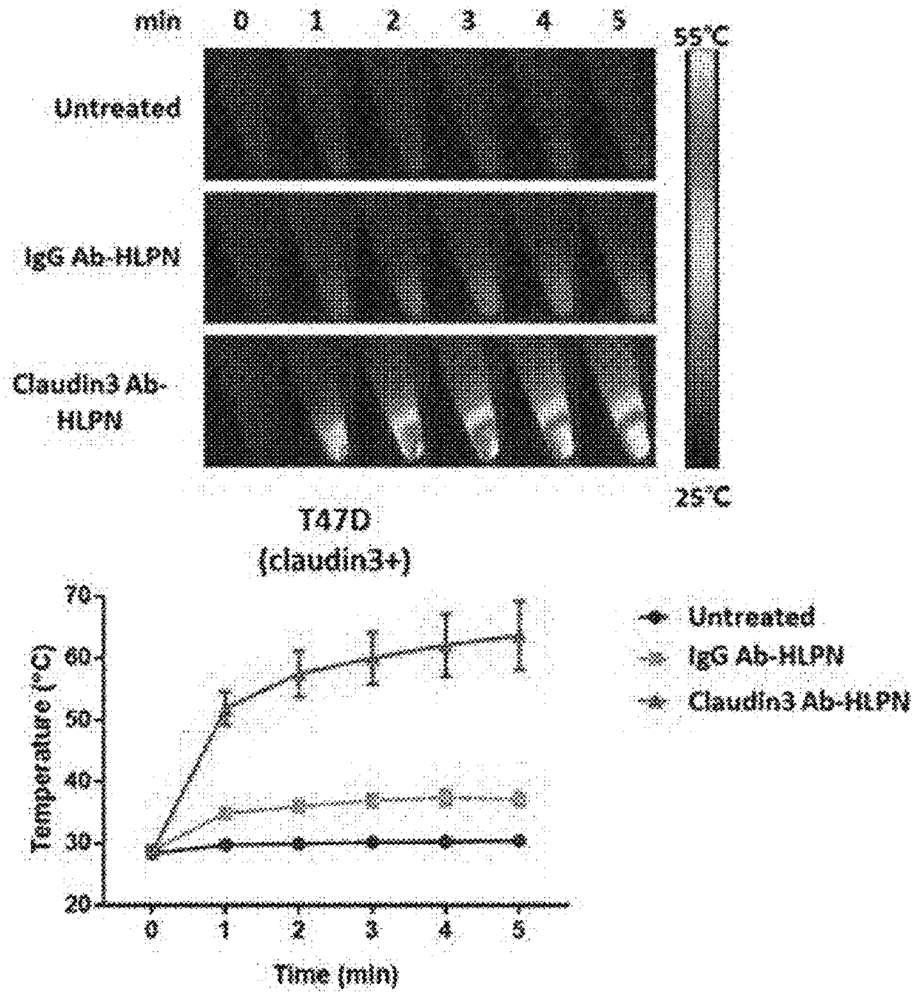
FIG. 10 illustrates the measurement of the temperature of cancer cells over the time of irradiation with near-infrared rays in Claudin3-overexpressing cancer cells treated with Claudin3 Ab-HLPN having a phospholipid composition of Composition 1, and is a set of views confirming that the temperature was increased to 50° C. or higher, and thus the temperature of cancer cells could be increased.
Figure 11:
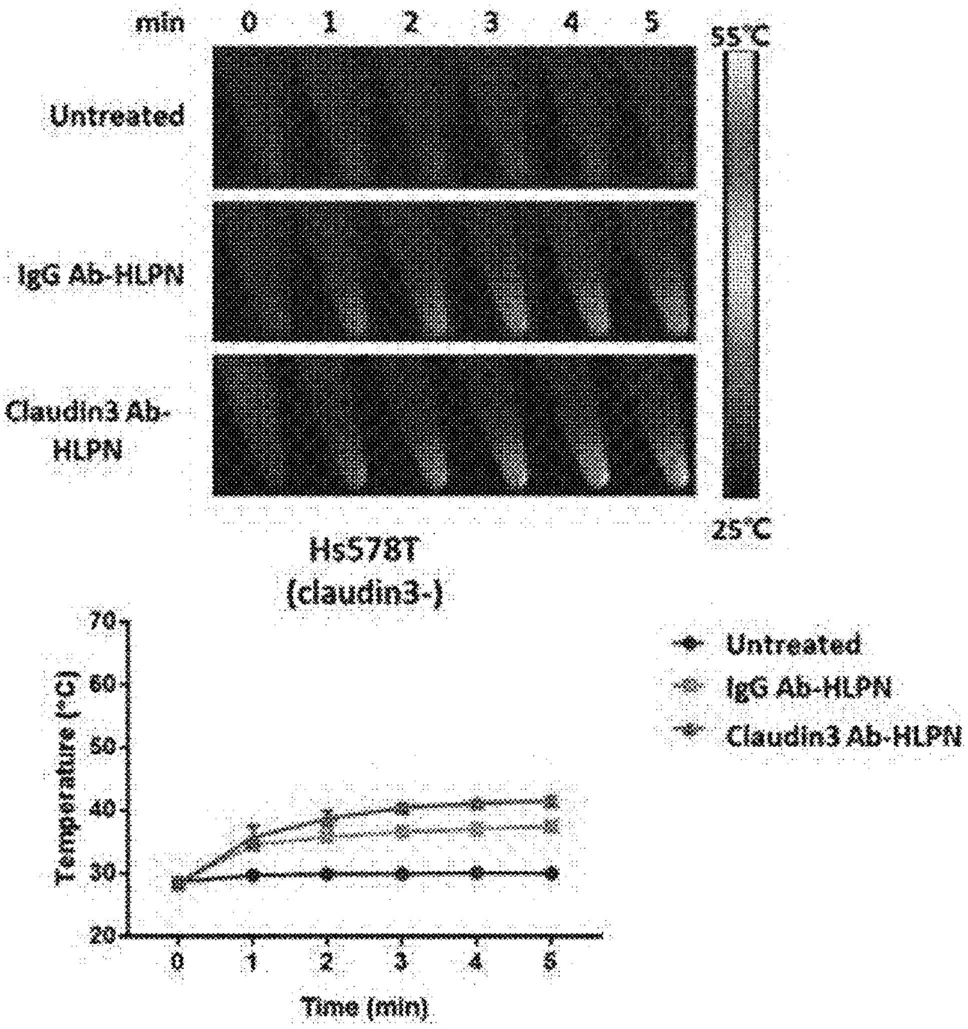
FIG. 11 illustrates the measurement of the temperature of cancer cells over the time of irradiation with near-infrared rays in Claudin3-non-expressing cancer cells treated with Claudin3 Ab-HLPN having a phospholipid composition of Composition 1, and is a set of views confirming that the temperature was not increased.

Furthermore, it was confirmed that the nanoparticle including the phospholipid of Composition 1 can induce a photothermal effect by increasing the temperature when irradiated with light in Claudin3-overexpressing cancer cells (FIGS. 9 to 11).

Figure 12:
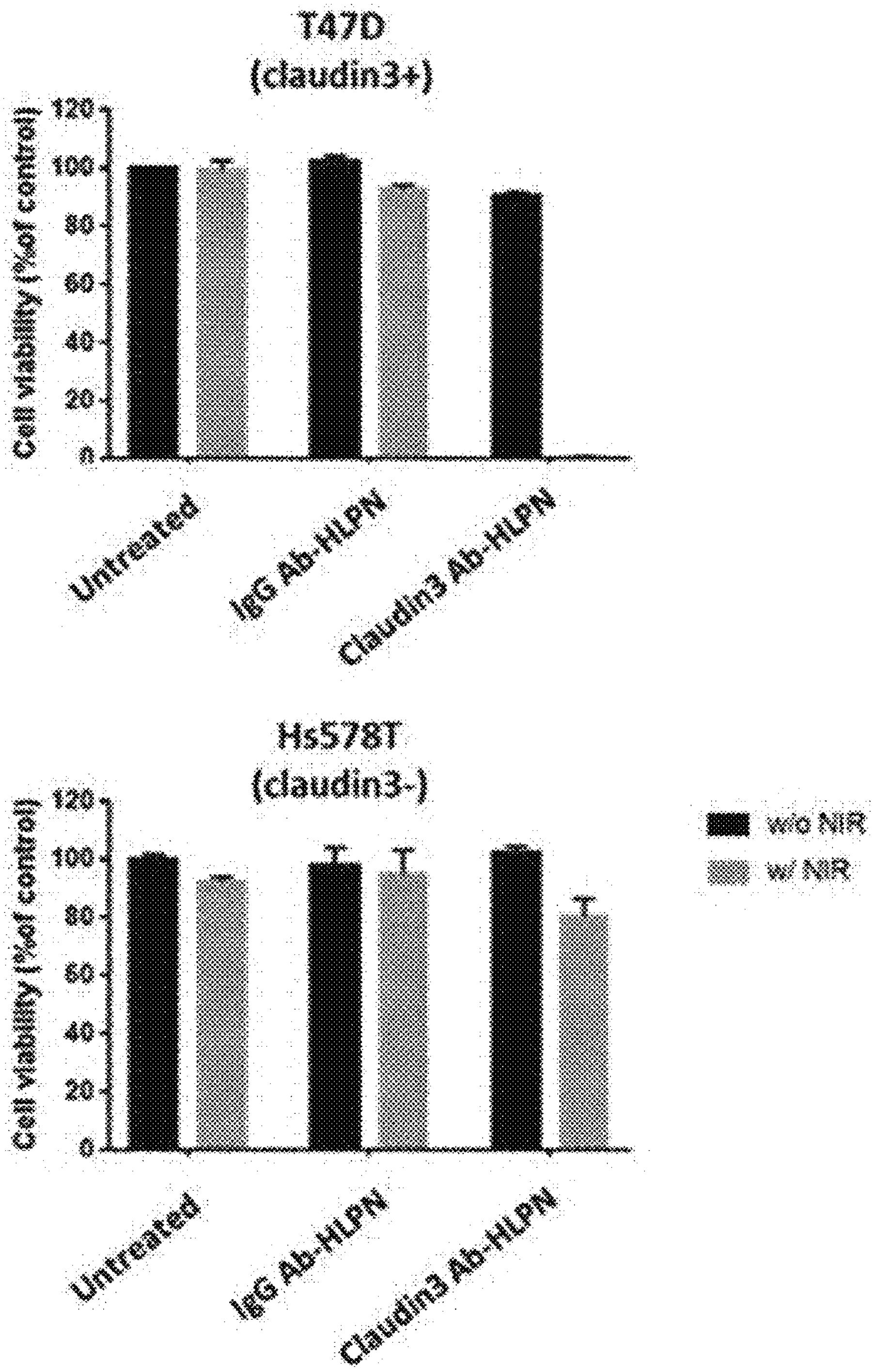
FIG. 12 illustrates the measurement of the survival rate of cancer cells after cancer cells treated with Claudin3 Ab-HLPN having a phospholipid composition of Composition 1 are irradiated with near-infrared rays, and is a view confirming that most of the Claudin3-expressing cancer cells were killed.
Figure 13:
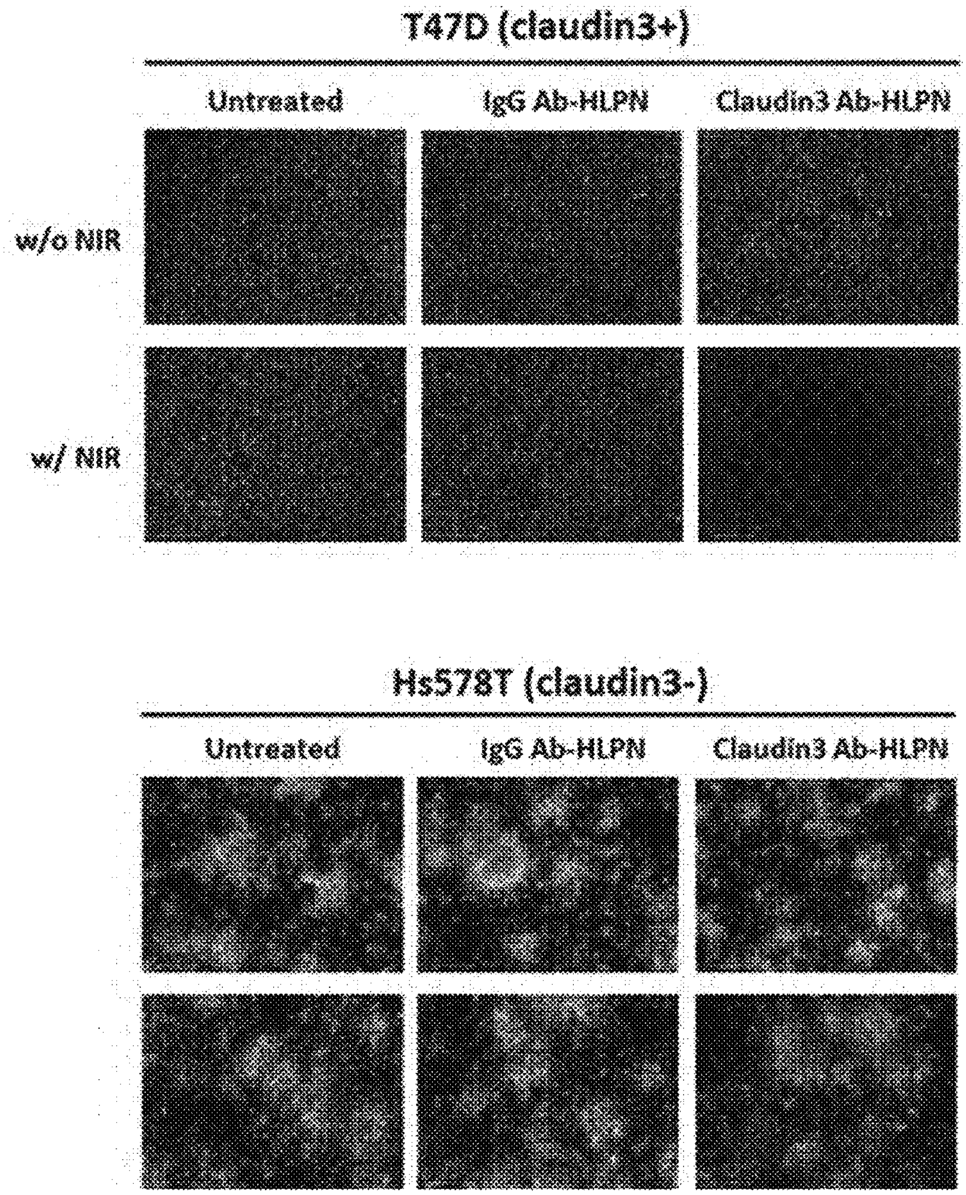
FIG. 13 illustrates the observation of stained surviving cancer cells by a fluorescence microscope after irradiating cancer cells treated with Claudin3 Ab-HLPN having a phospholipid composition of Composition 1 with near-infrared rays, and is a set of views confirming that most of the Claudin3-expressing cancer cells were killed.

Further, it was confirmed that the nanoparticle including the phospholipid of Composition 1 can kill cancer cells by inducing a photothermal effect when irradiated with light in Claudin3-overexpressing cancer cells (FIGS. 12 and 13).

Figure 14:
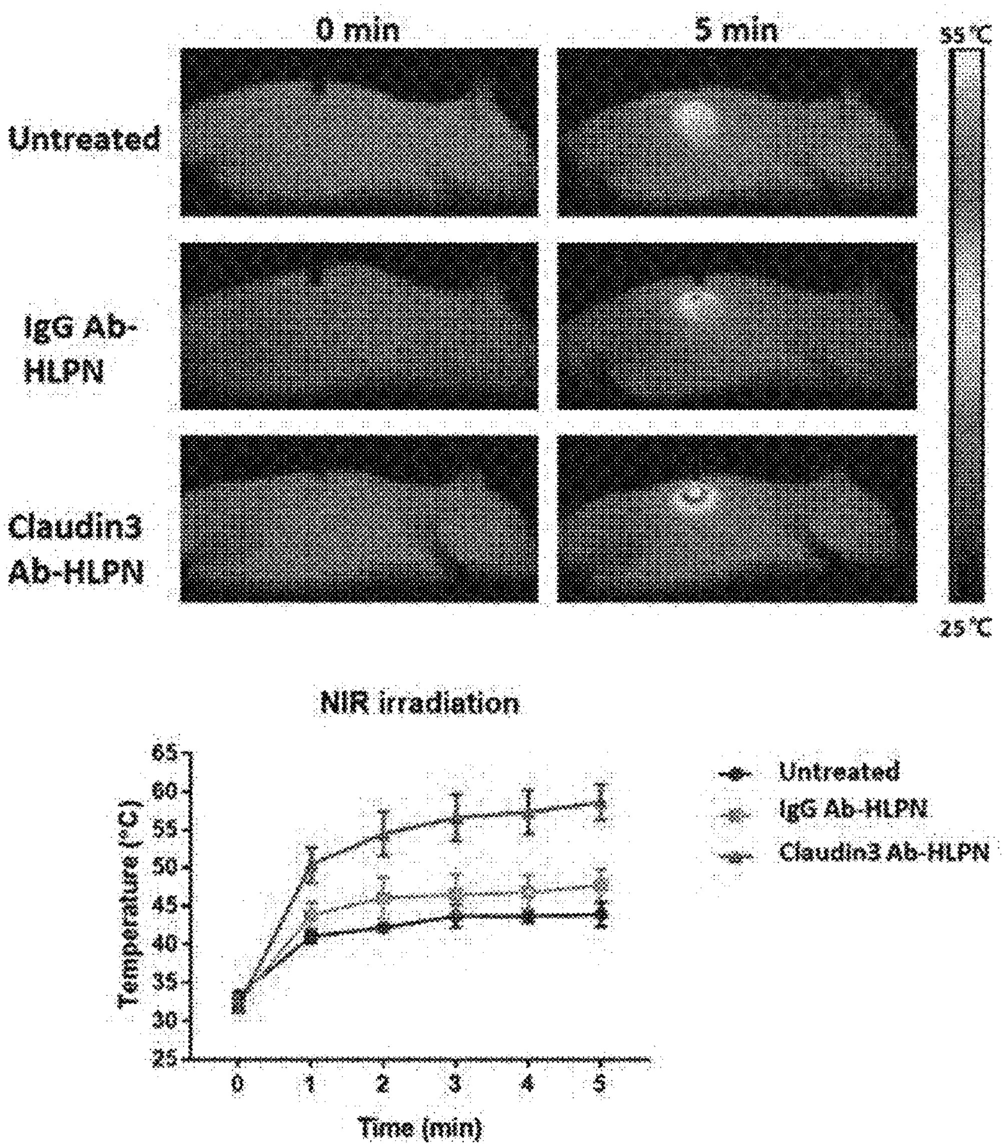
FIG. 14 illustrates the measurement of the temperature after tumor animal models overexpressing Claudin3 are systemically administered Claudin3 Ab-HLPN having a phospholipid composition of Composition 1, and then irradiated with near-infrared rays, and is a set of views confirming that the temperature was increased to 50° C. or higher, and thus the temperature of cancer cells could be increased.
Figure 15:
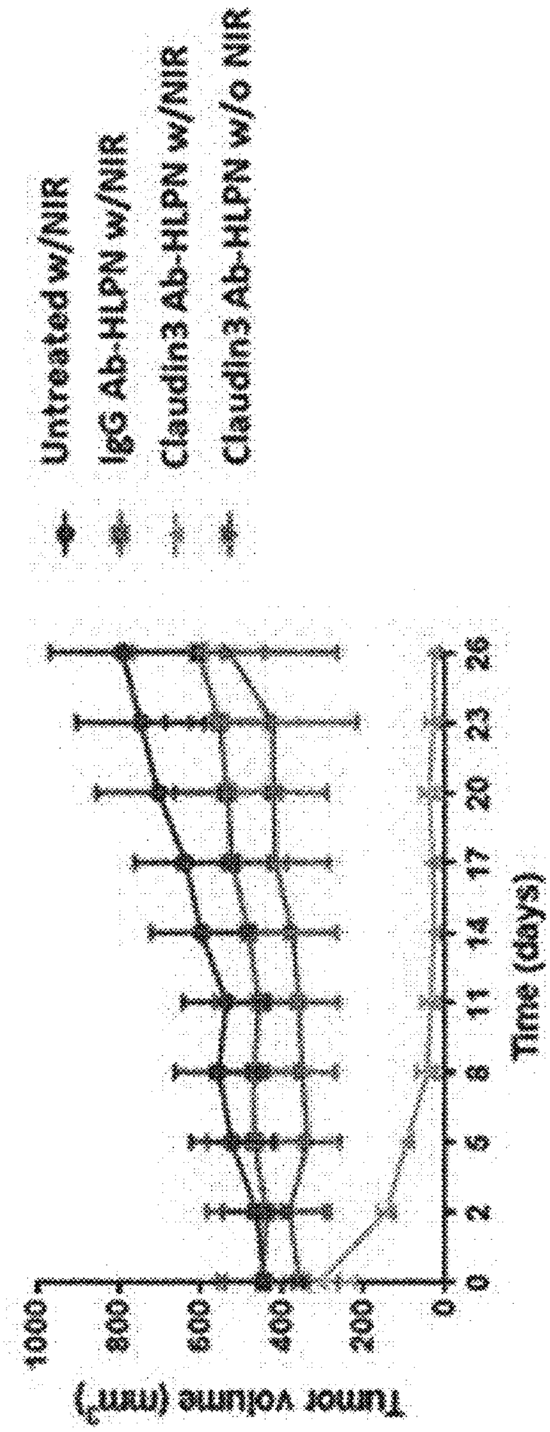
FIG. 15 illustrates the measurement of the volume of primary tumors after tumor animal models overexpressing Claudin3 are systemically administered Claudin3 Ab-HLPN having a phospholipid composition of Composition 1, and then irradiated with near-infrared rays, and is a view confirming that the tumor volume can be remarkably reduced.
Figure 16:
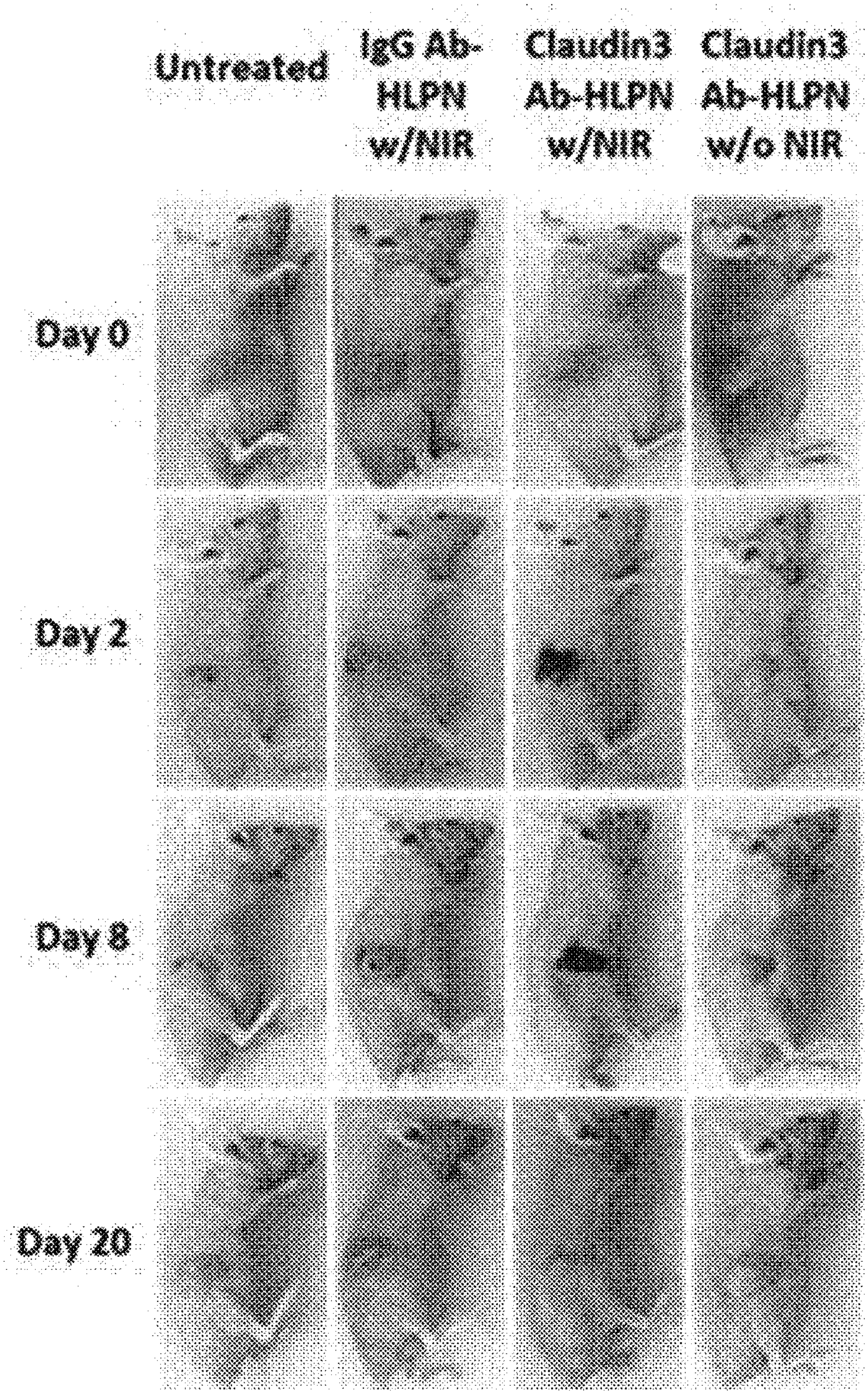
FIG. 16 illustrates the observation of the tumors of animals during a period when tumor animal models overexpressing Claudin3 are systemically administered Claudin3 Ab-HLPN having a phospholipid composition of Composition 1 and irradiated with near-infrared rays, and is a set of views confirming that the growth of primary tumors can be effectively suppressed.

In addition, it was confirmed that when the nanoparticle including the phospholipid of Composition 1 was irradiated with light in an animal model into which Claudin3-overexpressing cancer cells were injected, the temperature was increased by inducing a photothermal effect, and tumor volumes could be reduced due to the induced photothermal effect (FIGS. 14 to 16).

Figure 20:
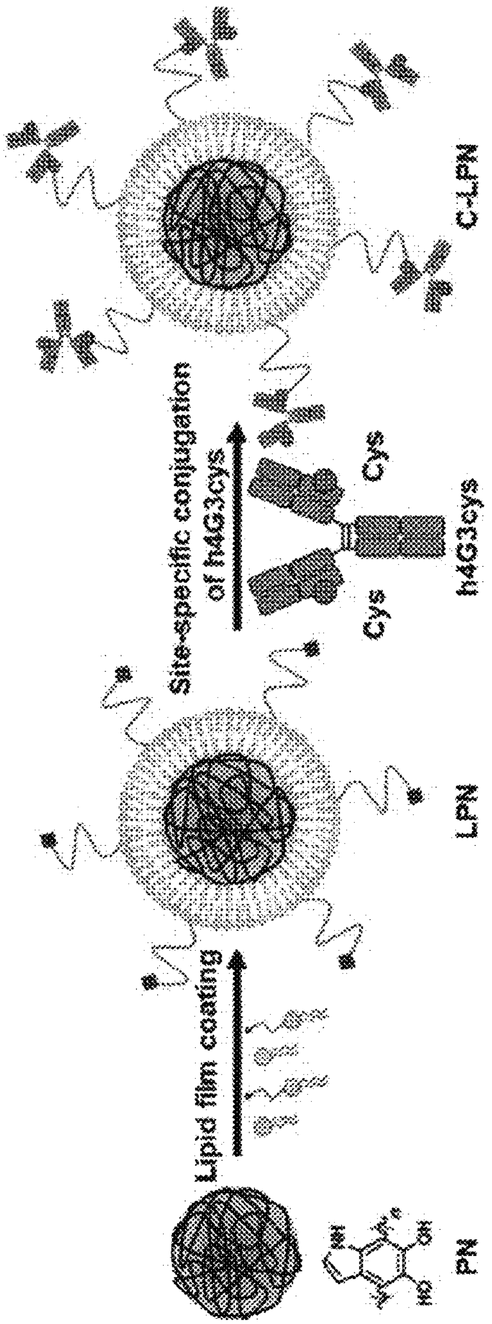
FIG. 20 is a view illustrating the process of preparing lipid-photothermal nanoparticle (C-LPN), in which a modified anti-Claudin3 antibody (h4G3cys) according to the present invention is site-specifically conjugated on the surface.

Furthermore, in specific exemplary embodiments of the present invention, the present inventors prepared a phospholipid-photothermal nanoparticle having an antibody site-specifically conjugated to the surface thereof (FIG. 20).

Therefore, the present inventors confirmed that a Claudin antibody (h43Gcys), in which the Q125 residue is substituted with cysteine, has no change in cancer cell binding ability, higher thiol reactivity, and more strongly binds to a maleimide group than an existing group (h43G) (FIGS. 21 to 24).

Further, by preparing a nanoparticle (C-LPN) in which h43Gcys is site-specifically conjugated to maleimide of a polydopamine hybrid nanoparticle (LPN), the morphology and size thereof, constituent elements, lipid content, and antibody binding efficiency were confirmed (FIGS. 25 to 30).

In addition, it was confirmed that when C-LPN was irradiated with near-infrared rays, an excellent photothermal ability was exhibited, and the ability to bind to Claudin3-overexpressing cancer cells was remarkably better than the ability to bind to Claudin3-non-expressing cancer cells (FIGS. 31 to 37).

Furthermore, when Claudin3-expressing cancer cells were treated with C-LPN, and then irradiated with near-infrared rays, the temperature of the cancer cells was increased and the cell viability was remarkably reduced, so that it was confirmed that C-LPN exhibits an excellent photothermal therapeutic effect against cancer cells (FIGS. 38 to 41).

Figure 42:
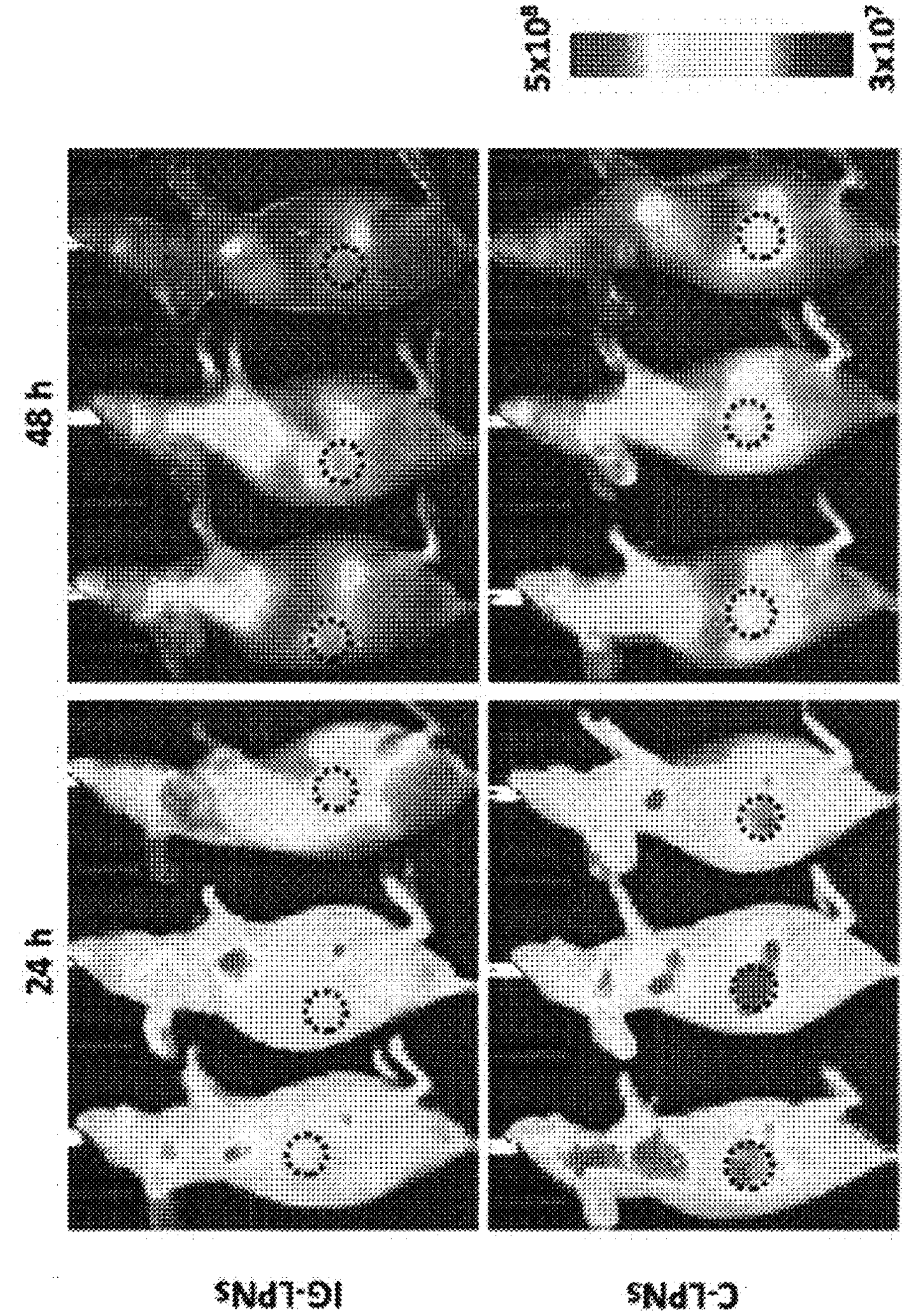
FIG. 42 illustrates the observation of the distribution of nanoparticles in the whole bodies of mice after treating a tumor animal model with IG-LPN or C-LPN, and is a set of views confirming that C-LPN was accumulated in tumor tissue.
Figure 43:
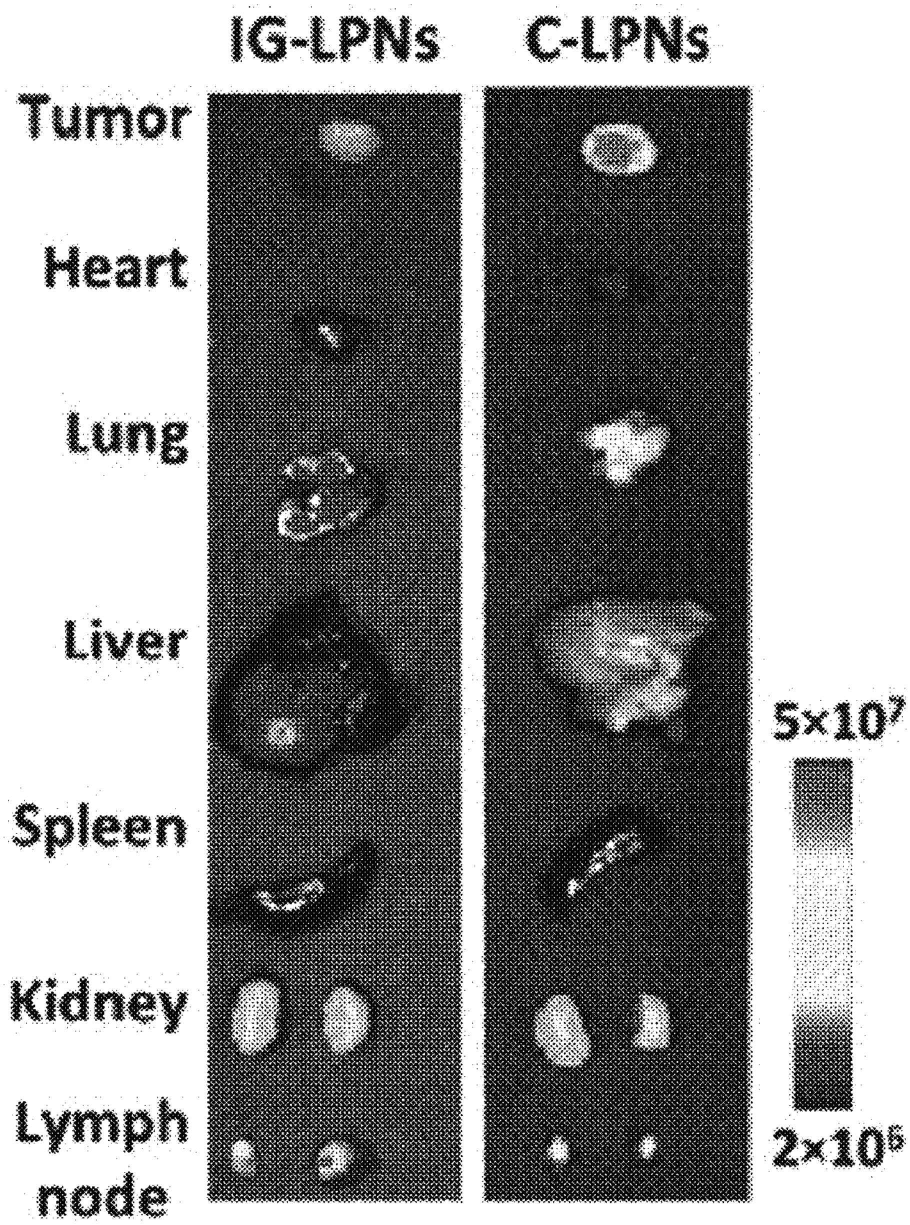
FIG. 43 illustrates the observation of the distribution of nanoparticles by removing tumor tissue and major organs after treating a tumor animal model with IG-LPN or C-LPN, and is a set of views confirming that C-LPN was accumulated in tumor tissues.
Figure 44:
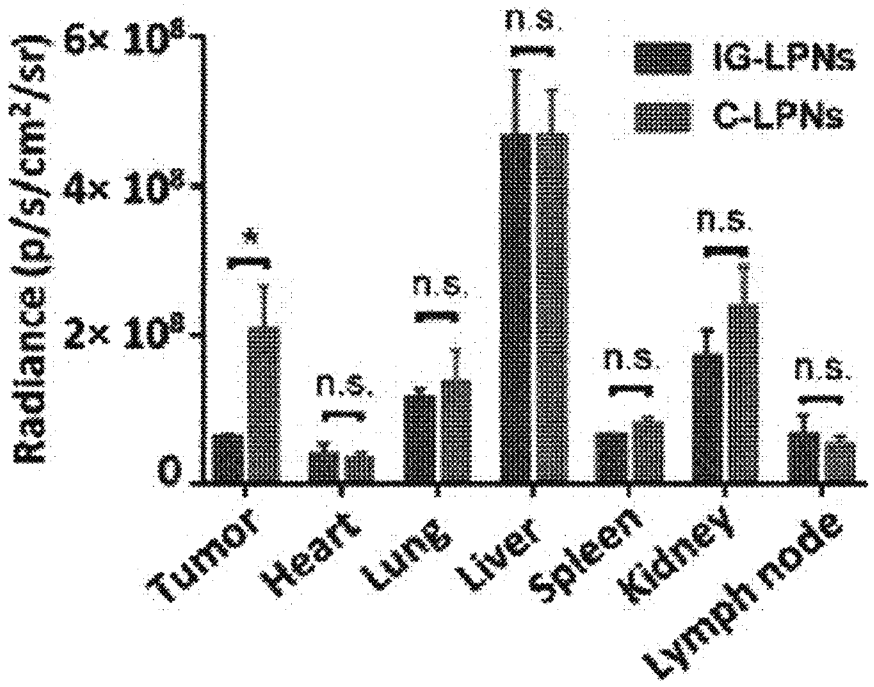
FIG. 44 confirms the distribution of nanoparticles by ex vivo imaging by removing tumor tissue and major organs after treating a tumor animal model with IG-LPN or C-LPN, and is a view confirming that C-LPN was specifically accumulated in tumor tissue compared to IG-LPN.

Further, a tumor animal model was prepared and treated with C-LPN, its distribution was confirmed, and as a result, it was confirmed that C-LPN was intensively accumulated in tumor tissue (FIGS. 42 to 44).

In addition, as a result of treating the tumor animal model with C-LPN, and then irradiating the tumor animal model with near-infrared rays, the tumor tissue temperature of the animal model was increased, the tumor volume was reduced, and the cell apoptosis of cancer cells in tumor tissue occurred actively, so that it was confirmed that C-LPN also exhibits an excellent photothermal effect in the tumor animal model (FIGS. 42 to 51).

Therefore, the pharmaceutical composition of the present invention has high stability when a phospholipid at a specific composition ratio is included, can induce a photothermal effect due to photothermal nanoparticles entrapped inside the phospholipid by specifically binding to proteins expressed on the surface of cancer cells, can kill cancer cells due to the photothermal effect, and then may be usefully used for a pharmaceutical composition for treating cancer.

Hereinafter, the present invention will be described in detail with reference to the following Examples and Experimental Examples.

However, the following Examples and Experimental Examples are only for exemplifying the present invention, and the present invention is not limited by the following Examples and Experimental Examples.

<Example 1> Preparation of Lipid-Photothermal Nanoparticle Having Antibody Bound to Surface Thereof (Ab-HLPN)

A polydopamine nanoparticle having an antibody bound to the surface lipid end thereof and surrounded by a phospholipid layer thin film (hereinafter, referred to as Ab-HLPN) was prepared at various phospholipid composition ratios.

<1-1> Preparation of Polydopamine Nanoparticle (PDN)

Polydopamine nanoparticles were synthesized through self-polymerization of dopamine in an alkaline solution.

Specifically, after 50 mg of dopamine hydrochloride (Sigma-Aldrich, St. Louis, MO, USA) was dissolved in 25 ml of triple distilled water (TDW), pH was titrated to 10 by slowly adding a 1 N sodium hydroxide solution dropwise to the dopamine hydrochloride solution, and the resulting mixture was magnetically stirred at 50° C. for 12 hours. A black pellet of polydopamine nanoparticles was collected by centrifuging the reaction solution at 13500×g for 20 minutes, and the pellet was washed with triple distilled water (TDW) until the supernatant became clear. After the final washing, the polydopamine nanoparticles were resuspended in triple distilled water and stored at 4° C.

<1-2> Preparation of Ab-HLPN (Composition 1)

A lipid thin film was hydrated with the polydopamine nanoparticles prepared in Example 1-1 to prepare a lipid-photothermal nanoparticle (HLPN) having a phospholipid composition of DPPC:DPPG=7:3.

Specifically, after 1,2-dipalmitoyl-sn-glycero-3-phosphocholine (DPPC), 1,2-dipalmitoyl-sn-glycero-3-phosphorylglycerol (DPPG), and 1,2-distearoyl-sn-glycero-3-phosphoethanolamine-N-[maleimide(polyethyleneglycol)-2000] (ammonium salt) (DSPE-PEG2000-maleimide) were dissolved at a molar ratio of 7:3:0.1 in chloroform-methanol (4:1, v/v), the resulting solution was concentrated under reduced pressure to prepare a lipid thin film. The prepared lipid thin film was hydrated by adding the polydopamine solution prepared in Example 1-1. Thereafter, an antibody was added and the resulting mixture was vigorously stirred. The corresponding reaction was performed at 4° C. overnight, and one day later, a lipid-photothermal nanoparticle having an antibody having a lipid composition of Composition 1 bound to the surface thereof (Ab-HLPN) was collected by centrifugation at 13500×g for 20 minutes, the collected lipid-photothermal nanoparticles were re-suspended in 1 ml of distilled water, and then the resulting suspension was allowed to pass through a 400-nm polycarbonate membrane and stored at 4° C.

<1-3> Preparation of Ab-HLPN (Composition 2)

A lipid thin film was hydrated with the polydopamine nanoparticles prepared in Example 1-1 to prepare a lipid-photothermal nanoparticle (HLPN) having a phospholipid composition of DPPC:PG=7:3.

Specifically, after 1,2-dipalmitoyl-sn-glycero-3-phosphocholine (DPPC), phosphorylglycerol (PG), and DSPE-PEG2000-maleimide were dissolved at a molar ratio of 7:3:0.1 in chloroform-methanol (4:1, v/v), the resulting solution was concentrated under reduced pressure to prepare a lipid thin film. The prepared lipid thin film was hydrated by adding the polydopamine solution prepared in Example 1-1. Thereafter, an antibody was added and the resulting mixture was vigorously stirred. The corresponding reaction was performed at 4° C. overnight, and one day later, a lipid-photothermal nanoparticle having an antibody having a lipid composition of Composition 2 bound to the surface thereof (Ab-HLPN) was collected by centrifugation at 13500×g for 20 minutes, the collected lipid-photothermal nanoparticles were re-suspended in 1 ml of distilled water, and then the resulting suspension was allowed to pass through a 400-nm polycarbonate membrane and stored at 4° C.

<1-4> Preparation of Ab-HLPN (Composition 3)

A lipid thin film was hydrated with the polydopamine nanoparticles prepared in Example 1-1 to prepare a lipid-photothermal nanoparticle (HLPN) having a phospholipid composition of PC:DPPG=7:3.

Specifically, after phosphocholine (PC), 1,2-dipalmitoyl-sn-glycero-3-phosphorylglycerol (DPPG), and DSPE-PEG2000-maleimide were dissolved at a molar ratio of 7:3:0.1 in chloroform-methanol (4:1, v/v), the resulting solution was concentrated under reduced pressure to prepare a lipid thin film. The prepared lipid thin film was hydrated by adding the polydopamine solution prepared in Example 1-1. Thereafter, an antibody was added and the resulting mixture was vigorously stirred. The corresponding reaction was performed at 4° C. overnight, and one day later, a lipid-photothermal nanoparticle having an antibody having a lipid composition of Composition 3 bound to the surface thereof (Ab-HLPN) was collected by centrifugation at 13500×g for 20 minutes, the collected lipid-photothermal nanoparticles were re-suspended in 1 ml of distilled water, and then the resulting suspension was allowed to pass through a 400-nm polycarbonate membrane and stored at 4° C.

<1-5> Preparation of Ab-HLPN (Composition 4)

A lipid thin film was hydrated with the polydopamine nanoparticles prepared in Example 1-1 to prepare a lipid-photothermal nanoparticle (HLPN) having a phospholipid composition of PC:PG=7:3.

Specifically, after phosphocholine (PC), phosphorylglycerol (PG), and DSPE-PEG2000-maleimide were dissolved at a molar ratio of 7:3:0.1 in chloroform-methanol (4:1, v/v), the resulting solution was concentrated under reduced pressure to prepare a lipid thin film. The prepared lipid thin film was hydrated by adding the polydopamine solution prepared in Example 1-1. Thereafter, an antibody was added and the resulting mixture was vigorously stirred. The corresponding reaction was performed at 4° C. overnight, and one day later, a lipid-photothermal nanoparticle having an antibody having a lipid composition of Composition 4 bound to the surface thereof (Ab-HLPN) was collected by centrifugation at 13500×g for 20 minutes, the collected lipid-photothermal nanoparticles were re-suspended in 1 ml of distilled water, and then the resulting suspension was allowed to pass through a 400-nm polycarbonate membrane and stored at 4° C.

<1-6> Preparation of Ab-HLPN (Composition 5)

A lipid thin film was hydrated with the polydopamine nanoparticles prepared in Example 1-1 to prepare a lipid-photothermal nanoparticle (HLPN) having a phospholipid composition of DPPC=10.

Specifically, after 1,2-dipalmitoyl-sn-glycero-3-phosphocholine (DPPC) and DSPE-PEG2000-maleimide were dissolved at a molar ratio of 10:0.1 in chloroform-methanol (4:1, v/v), the resulting solution was concentrated under reduced pressure to prepare a lipid thin film. The prepared lipid thin film was hydrated by adding the polydopamine solution prepared in Example 1-1. Thereafter, an antibody was added and the resulting mixture was vigorously stirred. The corresponding reaction was performed at 4° C. overnight, and one day later, a lipid-photothermal nanoparticle having an antibody having a lipid composition of Composition 5 bound to the surface thereof (Ab-HLPN) was collected by centrifugation at 13500×g for 20 minutes, the collected lipid-photothermal nanoparticles were re-suspended in 1 ml of distilled water, and then the resulting suspension was allowed to pass through a 400-nm polycarbonate membrane and stored at 4° C.

<1-7> Preparation of Ab-HLPN (Composition 6)

A lipid thin film was hydrated with the polydopamine nanoparticles prepared in Example 1-1 to prepare a lipid-photothermal nanoparticle (HLPN) having a phospholipid composition of PC=10.

Specifically, after phosphocholine (PC) and DSPE-PEG2000-maleimide were dissolved at a molar ratio of 10:0.1 in chloroform-methanol (4:1, v/v), the resulting solution was concentrated under reduced pressure to prepare a lipid thin film. The prepared lipid thin film was hydrated by adding the polydopamine solution prepared in Example 1-1. Thereafter, an antibody was added and the resulting mixture was vigorously stirred. The corresponding reaction was performed at 4° C. overnight, and one day later, a lipid-photothermal nanoparticle having an antibody having a lipid composition of Composition 6 bound to the surface thereof (Ab-HLPN) was collected by centrifugation at 13500×g for 20 minutes, the collected lipid-photothermal nanoparticles were re-suspended in 1 ml of distilled water, and then the resulting suspension was allowed to pass through a 400-nm polycarbonate membrane and stored at 4° C.

<1-8> Preparation of Ab-HLPN (Composition 7)

A lipid thin film was hydrated with the polydopamine nanoparticles prepared in Example 1-1 to prepare a lipid-photothermal nanoparticle (HLPN) having a phospholipid composition of DPPG=10.

Specifically, after 1,2-dipalmitoyl-sn-glycero-3-phosphorylglycerol (DPPG) and DSPE-PEG2000-maleimide were dissolved at a molar ratio of 10:0.1 in chloroform-methanol (4:1, v/v), the resulting solution was concentrated under reduced pressure to prepare a lipid thin film. The prepared lipid thin film was hydrated by adding the polydopamine solution prepared in Example 1-1. Thereafter, an antibody was added and the resulting mixture was vigorously stirred. The corresponding reaction was performed at 4° C. overnight, and one day later, a lipid-photothermal nanoparticle having an antibody having a lipid composition of Composition 7 bound to the surface thereof (Ab-HLPN) was collected by centrifugation at 13500×g for 20 minutes, the collected lipid-photothermal nanoparticles were re-suspended in 1 ml of distilled water, and then the resulting suspension was allowed to pass through a 400-nm polycarbonate membrane and stored at 4° C.

<Experimental Example 1> Evaluation of Cancer Cell Binding Ability According to Phospholipid Composition of Ab-HLPN The ability of Ab-HLPN (Compositions 1 to 7) each prepared in Example 1 to bind to a Claudin3-overexpressing cell line T47D was confirmed.

Specifically, T47D cells were cultured at a density of $2\times10^5$ cells per well in an RPMI medium supplemented with 10% fetal bovine serum, 100 units/ml penicillin and 100 mg/ml streptomycin. The next day, each well was treated with the Ab-HLPN (Compositions 1 to 7) prepared in Example 1 so as to have a concentration of 50 μg/ml, and after 1 hour, cells were isolated using a cell dissociation solution (enzyme-free, phosphate-buffered saline (PBS)-based cell dissociation buffer), washed with cold phosphate buffered saline (PBS) and further cultured with Alexa Flour 647-conjugated goat anti-human IgG (Biolegend Inc., San Diego, CA, USA) for 1 hour. The cultured cells were washed with PBS, and the intensity of fluorescence was measured by flow cytometry.

As a result, as illustrated in FIG. 2, it was confirmed that Compositions 1 to 6 all bind well to Claudin3-overexpressing cancer cells, but it was confirmed that Composition 7 does not bind well to Claudin3-overexpressing cancer cells. The results suggest that the cancer cell binding ability may vary depending on the type and composition of the phospholipid, even though nanoparticles are prepared using the same antibody.

<Experimental Example 2> Evaluation of Cancer Cell Binding Ability According to Phospholipid Composition of Ab-HLPN The ability of Ab-HLPN (Compositions 1 to 7) each prepared in Example 1 to bind to a Claudin3-non-expressing cell line Hs578T was confirmed.

Specifically, Hs578T cells were cultured at a density of $2\times10^5$ cells per well in a DMEM medium supplemented with 10% fetal bovine serum, 100 units/ml penicillin and 100 mg/ml streptomycin. The next day, each well was treated with the Ab-HLPN (Compositions 1 to 7) prepared in Example 1 so as to have a concentration of 50 μg/ml, and after 1 hour, cells were isolated using a cell dissociation solution (enzyme-free, phosphate-buffered saline (PBS)-based cell dissociation buffer), washed with cold phosphate buffered saline (PBS) and further cultured with Alexa Flour 647-conjugated goat anti-human IgG (Biolegend Inc., San Diego, CA, USA) for 1 hour. The cultured cells were washed with PBS, and the intensity of fluorescence was measured by flow cytometry.

As a result, as illustrated in FIG. 3, it was confirmed that none of Compositions 1 to 7 bind to Claudin3-non-expressing cancer cells.

<Experimental Example 3> Evaluation of Particle Stability According to Phospholipid Composition of Ab-HLPN After the preparation of Ab-HLPN (Compositions 1 to 7) each prepared in Example 1, stability was observed.

Specifically, after Ab-HLPN according to various phospholipid compositions was prepared according to Example 1, particle stability was identified in a medium supplemented with 10% fetal bovine serum, 100 units/ml penicillin and 100 mg/ml streptomycin by the naked eye after 24 hours.

As a result, as illustrated in FIG. 4, it was confirmed that in Compositions 3 to 7, precipitates were observed at the bottom end of an EP tube, the particles were not stabilized and were separated, but Ab-HLPN of Example 1-2 (Composition 1) and Example 1-3 (Composition 2) maintained a uniform composition even after 24 hours from the preparation of the particles, the particle size was maintained without precipitation, and the particles were most stable. Stability is a physical property that is essentially required for product development, and Ab-HLPN of Compositions 1 and 2 are determined to be suitable for in vivo administration due to high stability.

<Experimental Example 4> Evaluation of Particle Size of Ab-HLPN

<4-1> Evaluation of Particle Size of Ab-HLPN of Compositions 1 to 7

Particle size was evaluated as a physicochemical property of the Ab-HLPN having phospholipid compositions of Compositions 1 to 7 prepared in Example 1.

Specifically, after the preparation of the polydopamine nanoparticles and Compositions 1 to 7 prepared in Example 1, they were stored in a medium supplemented with 10% fetal bovine serum, 100 units/ml penicillin and 100 mg/ml streptomycin for 24 hours, and the size of Ab-HLPN was measured using a dynamic scattering method (ELS8000 instrument, Photal, Osaka, Japan).

As a result, as illustrated in Table 1, it was confirmed that the Ab-HLPN of Compositions 1 and 2 had the smallest particle size. Since Compositions 1 and 2 maintain their particle size at 10% FBS/media (cell culture conditions) without being precipitated or growing like the rest of the compositions, it is possible to predict that particle stability will be maintained even during in vivo application.

TABLE 1

| Composition | Lipid composition | Particle size (nm) in 10% FBS/Media |
|---|---|---|
| Composition 1 | DPPC:DPPG = 7:3 | 175 ± 55 |
| Composition 2 | DPPC:PG = 7:3 | 167 ± 40 |
| Composition 3 | PC:DPPG = 7:3 | 758 ± 86 |
| Composition 4 | PC:PG = 7:3 | 2463 ± 648 |
| Composition 5 | DPPC = 10 | 486 ± 136 |
| Composition 6 | PC = 10 | 650 ± 79.3 |
| Composition 7 | DPPG = 10 | 342 ± 94 |

<4-2> Evaluation of Particle Size and Morphology of Ab-HLPN of Composition 1

The particle size and morphology of the Ab-HLPN of Composition 1 prepared in Example 1-2 were evaluated.

Specifically, the particle size was measured in the same manner as described in Experimental Example 4-2, and the particle morphology was confirmed by a transmission electron microscope (TEM, JEOL, Tokyo, Japan).

As a result, as illustrated in FIG. 5, it was found that the Ab-HLPN particles of Composition 1 had a slightly larger average particle size than the polydopamine nanoparticles, and as illustrated in FIG. 6, for the morphology of the particles, a morphology in which a lipid thin film layer surrounded the polydopamine nanoparticles was observed.

Based on the above results, Ab-HLPN particles of Composition 1, which have the highest particle stability and the smallest size, were selected to evaluate their binding ability and photothermal therapeutic effect on the following cancer cells.

<Experimental Example 5> Evaluation of Ability to Bind to Cancer Cells

The ability of the Ab-HLPN of Composition 1 prepared in Example 1-2 to bind to cancer cells was evaluated using a transmission electron microscope and a fluorescence microscope.

<5-1> Evaluation of Ability to Bind to Cancer Cells Using Transmission Electron Microscope In order to confirm the ability of the Ab-HLPN prepared in Example 1 to bind to cancer cells, colorectal cancer cells treated with each particle were observed by a transmission electron microscope (TEM).

Specifically, after T74D, which is a cell line that overexpresses Claudin3, or Hs578T cells, which are a cell line that does not express Claudin3, was or were cultured in a 100 mm culture dish such that the area of the cells reached about 70% of the culture dish, each culture dish was treated with the Ab-HLPN of Composition 1 prepared in Example 1-2 so as to have a concentration of 0.5 mg/ml. After 6 hours, each cell was harvested and fixed in a Kamnovsky solution for 2 hours, then washed three times with cold 0.05 M sodium carcodylate buffer, and the pellet was post-fixed with 1% osmium tetroxide at 4° C. for 2 hours. The fixed pellet was washed three times with cold triple distilled water, then stained with 0.5% uranyl acetate at 4° C. overnight and dehydrated in ethanol (30%, 50%, 70%, 80%, 90% and 100% three times). The dehydrated cell pellet was infiltrated with 50:50 propyleneoxide/Spurr resin for 2 hours, then replaced with 100% Spurr resin and solidified in an oven at 70° C. for 24 hours. The pellet was cut into ultrafine cross sections (60 nm) and observed by TEM.

As a result, as illustrated in FIG. 7, it could be confirmed that the Ab-HLPN of Composition 1 has remarkably excellent ability to bind to T47D cancer cells, which are a Claudin3-overexpressing cell line.

<5-2> Evaluation of Ability to Bind to Cancer Cells Using Fluorescence Microscope In order to confirm the ability of Composition 1 Ab-HLPN prepared in Example 1-2 to bind to cancer cells, Ab-HLPN-treated T74D or Hs578T was stained with FITC fluorescence and fluorescence-labeled antibody linked to a lipid and observed under a fluorescence microscope.

Specifically, T74D or Hs578T cells were cultured at a density of $0.5\times10^5$ cells per well in an RPMI medium supplemented with 10% fetal bovine serum, 100 units/ml penicillin and 100 mg/ml streptomycin. The next day, each well was treated with the Ab-HLPN of Composition 1 prepared in Example 1-2 so as to have a concentration of 0.5 mg/ml, and after 4 hours, each cell was washed with cold phosphate buffer solution (PBS) and further cultured with an Alexa Fluor 488-Goat-anti Rat IgG antibody (Biolegend, San Diego, CA, USA) for 1 hour. The cultured cells were washed with PBS, fixed with 4% paraformaldehyde for 15 minutes, and then stained with 4',6-diamidino-2-phenylindole dihydrochloride (DAPI, Sigma-Aldrich). The fluorescence of the cells was observed under a fluorescence microscope.

As a result, as illustrated in FIG. 8, fluorescence appeared only in Claudin3-overexpressing cancer cells treated with the Ab-HLPN particles of Composition 1 to which an anti-Claudin3 antibody was bound, showing that the ability to bind to cancer cells can be imparted by binding the antibody to the particle surface.

<Experimental Example 6> Evaluation of Photothermal Therapeutic Effect

In order to evaluate the photothermal therapeutic effect of Composition 1 Ab-HLPN prepared in Example 1-2, the cancer cells treated with each particle were irradiated with near-infrared rays to measure the change in temperature over time and the viability of the cancer cells after the irradiation.

<6-1> Measurement of Change in Temperature of Cancer Cells Over Time of Irradiation with Near-Infrared Rays T74D or Hs578T cells were treated with Composition 1 Ab-HLPN prepared in Example 1-2 and irradiated with near-infrared rays to observe the change in temperature of cancer cells over the time of irradiation.

Specifically, cancer cells were treated with particles dispersed in triple distilled water and irradiated using a near-infrared laser beam device (BWT Beijing LTD, Beijing, China) with an output power of 1.5 W at 808 nm. The change in temperature of the sample was measured and photographed by a thermal imaging camera (FLIR T420, FLIR system Inc., Danderyd, Sweden).

As a result, as illustrated in FIG. 9, a darker color of polydopamine nanoparticles was observed in a Claudin3-overexpressing cancer cell pellet (T47D) treated with Claudin3 Ab-HLPN than that of cells treated with isotype IgG-modified particles. The corresponding group did not show a significant difference in color between cell pellets in the Claudin3-non-expressing cell line (Hs578T). The above results suggest that the Claudin3-overexpressing cancer cell pellet (T47D) treated with Claudin3 Ab-HLPN induced a photothermal effect to increase the temperature.

Further, as illustrated in FIG. 10, it was confirmed that the temperature was higher in Claudin3-overexpressing cancer cells treated with Claudin3 Ab-HLPN than in cells treated with isotype IgG modified particles, the temperature was increased to 50° C. or higher upon irradiation with near-infrared rays for 1 minute or more, and thus particles to which the anti-Claudin3 antibody was bound were specifically accumulated in cancer cells to increase the temperature of cancer cells. The above results suggest that the Ab-HLPN particles prepared in the present invention can effectively induce the photothermal effect.

In addition, as illustrated in FIG. 11, it was confirmed that there was no difference between the groups in the Claudin3-non-expressing cancer cells treated with isotype IgG modified particles or Claudin3 Ab-HLPN, and the temperature did not exceed 40° C. during irradiation with near-infrared rays for 1 minute or more. The above results suggest that an antibody modified with Ab-HLPN target an antigen that can be specifically expressed in cancer cells to show photothermal therapeutic effects specifically on cancer cells, but not on normal cells.

<6-2> Measurement of Viability of Cancer Cells after Irradiation with Near-Infrared Rays After T74D or Hs578T cells were treated with the anti-Claudin3 antibody-bound Ab-HLPN of Composition 1 prepared in Example 1-2 and irradiated with near-infrared rays, the viability of cancer cells was measured by MTT assay.

Specifically, a 3-(4,5-dimethylthizol-2-yl)-2,5-diphenyltetrazolium bromide (MTT) reagent (Sigma-Aldrich) as much as 10% of the medium was added to cancer cells treated with the Ab-HLPN particles of Composition 1 prepared in Example 1-2, and the cells were cultured for 2 hours. Thereafter, the medium and the MTT reagent were removed, formazan was dissolved by adding DMSO, and absorbance was measured at 570 nm.

As a result, as illustrated in FIG. 12, it was found that there was a greater cell death effect in Claudin3-overexpressing cancer cells treated with the anti-Claudin3 antibody-bound Ab-HLPN, and almost all the cancer cells were killed. It was confirmed that antibody-bound particles are specifically accumulated in cancer cells to enhance the effect of photothermal therapy on cancer cells.

<6-3> Observation of Surviving Cancer Cells after Irradiation with Near-Infrared Rays After T74D or Hs578T cells were treated with the anti-Claudin3 antibody-bound Ab-HLPN prepared in Example 1 and irradiated with near-infrared rays, the viability of cancer cells was observed under a fluorescence microscope.

Specifically, a Calcein reagent was added to the cancer cells treated with particles, and after 10 minutes, the medium and the reagent were removed, and the surviving cells were observed under a fluorescence microscope by adding a new medium.

As a result, as illustrated in FIG. 13, it was found that there was a greater cell death effect in Claudin3-overexpressing cancer cells treated with the anti-Claudin3 antibody-bound Ab-HLPN, and almost all the cancer cells were killed. It was confirmed that antibody-bound particles are specifically accumulated in cancer cells to enhance the effect of photothermal therapy on cancer cells.

<Experimental Example 7> Evaluation of Photothermal Therapeutic Effect in Tumor Animal Model In order to evaluate the photothermal therapeutic effect of the anti-Claudin3 antibody-bound Ab-HLPN of Composition 1 prepared in Example 1-2 in a tumor animal model, the ability of each particle to bind to cancer cells was observed by a transmission electron microscope, and the temperature of cancer cells was measured by irradiating the animal model to which each particle was administered with near-infrared rays.

Specifically, after 107 T47D cells were subcutaneously injected into the right flank of Balb/c mice (6 weeks old), isotype IgG or the Claudin3 Ab-HLPN of Composition 1 prepared in Example 1-2 were intravenously administered at a dose of 2 mg of polydopamine nanoparticles per mouse by randomly assigning mice when the volume of tumor reached 300 $mm^3$. The next day, after the mouse was anesthetized and placed in a mouse holder, tumor sites were irradiated with an 808 nm near-infrared laser at an output of 1.5 W for 10 minutes, and the temperature was measured.

As a result, as illustrated in FIG. 14, it was confirmed that even in an animal model, particles to which the anti-Claudin3 antibody is bound may be specifically accumulated in cancer cells to enhance the photothermal therapeutic effect because the temperature was shown to be higher in an animal model to which Ab-HLPN in which the anti-Claudin3 antibody of Composition 1 was modified was administered than polydopamine nanoparticles alone or isotype IgG.

<Experimental Example 8> Evaluation of Tumor Therapeutic Effect in Tumor Animal Model In order to evaluate the photothermal therapeutic effect of the anti-Claudin3 antibody-bound Ab-HLPN of Composition 1 prepared in Example 1-2 in an animal model, the volume of cancer cells and the survival rate of mice were measured by irradiating a tumor animal model to which each particle was administered with near-infrared rays.

<8-1> Measurement of Tumor Volume

After the tumor animal model was administered isotype IgG or Claudin3 Ab-HLPN and irradiated with near-infrared rays, the tumor volume was measured over time.

Specifically, after 107 T47D cells were subcutaneously injected into the right flank of Balb/c mice (6 weeks old), isotype IgG or Claudin3 Ab-HLPN were intravenously administered at a dose of 2 mg of polydopamine nanoparticles per mouse by randomly assigning mice when the volume of tumor reached 300 $mm^3$. The next day, after the mouse was anesthetized and placed in a mouse holder, tumor sites were irradiated with an 808 nm near-infrared laser at an output of 1.5 W for 10 minutes. Tumor size was measured with calipers and tumor volume was calculated by an equation $a \times b^2 \times 0.5$, where a is the largest diameter and b is the smallest diameter.

As a result, as illustrated in FIGS. 15 and 16, it was confirmed that in an animal model administered Claudin3 Ab-HLPN and irradiated with near-infrared rays, the growth of primary tumors was effectively suppressed.

<8-2> Measurement of Body Weight of Animal Model

After the tumor animal model was administered isotype IgG or Claudin3 Ab-HLPN and irradiated with near-infrared rays, the body weight of the animal was measured over time.

Specifically, after 107 T47D cells were subcutaneously injected into the right flank of Balb/c mice (6 weeks old), isotype IgG or Claudin3Ab-HLPN were intravenously administered at a dose of 2 mg of polydopamine nanoparticles per mouse by randomly assigning mice when the volume of tumor reached 300 $mm^3$. The next day, after the mouse was anesthetized and placed in a mouse holder, tumor sites were irradiated with an 808 nm near-infrared laser at an output of 1.5 W for 10 minutes, and the body weight of the animal was measured.

Figure 17:
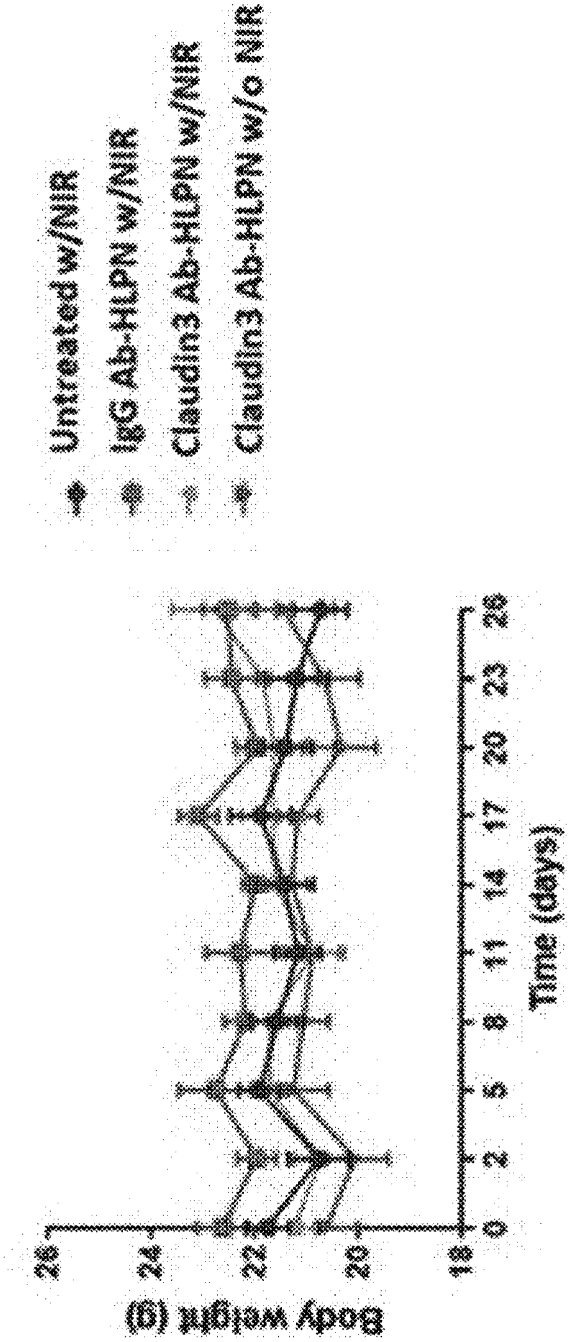
FIG. 17 illustrates the measurement of the body weights of animals after tumor animal models overexpressing Claudin3 are systemically administered Claudin3 Ab-HLPN having a phospholipid composition of Composition 1 and irradiated with near-infrared rays, and is a view confirming that there was no change in body weight.

As a result, as illustrated in FIG. 17, it was confirmed that there was no difference in the body weight of animals in all groups.

<Experimental Example 9> Evaluation of Cancer Cell Binding Ability of Ab-HLPN in which Herceptin Antibody is Modified It was confirmed whether Ab-HLPN in which other types of antibodies were modified also binds well to cancer cells in addition to the anti-Claudin3 antibody-modified Ab-HLPN prepared in Example 1.

Specifically, a herceptin antibody-modified Ab-HLPN was prepared in the same manner and conditions as the method of preparing Ab-HLPN in Example 1, except that as the used antibody, herceptin, which is an antibody against HER2, was used instead of an anti Claudin3 antibody. Thereafter, the ability to bind to an HER2-overexpressing cell line HCC1954 and an HER2-non-expressing cell line Hs578T was confirmed in the same manner as in Experimental Example 1.

Figure 18:
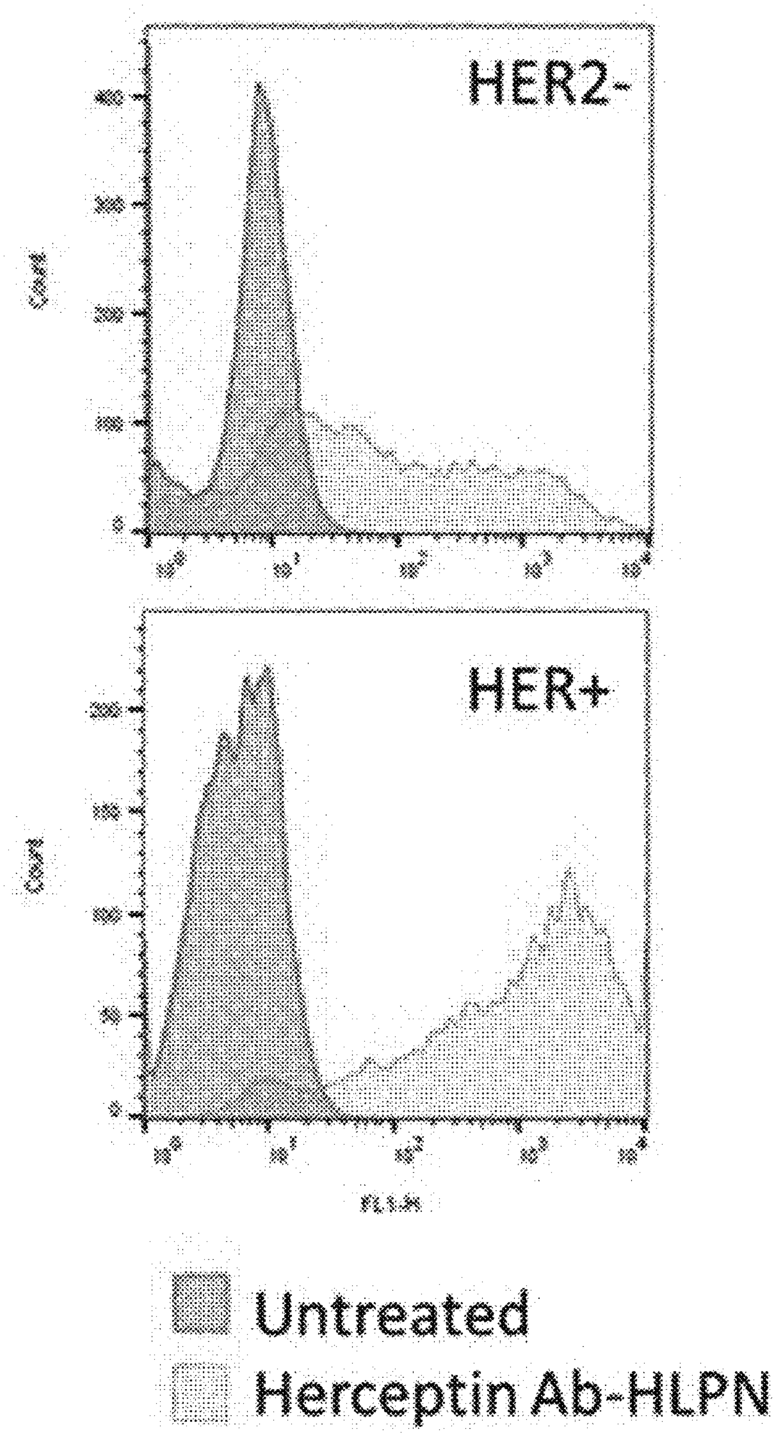
FIG. 18 illustrates the measurement of the ability of Ab-HLPN to which herceptin, which is an HER2 antibody, is bound to bind to HER2-overexpressing or non-expressing cancer cells by flow cytometry, and is a set of views confirming that herceptin-bound Ab-HLPN can bind well to HER2-overexpressing cells.

As a result, as illustrated in FIG. 18, it was confirmed that Herceptin Ab-HLPN binds well to HER2-overexpressing cancer cells. The above results suggest that various types of cancers can be treated by surface modification of antibodies that bind to antigens specifically expressed on cancer cells.

<Experimental Example 10> Evaluation of Cancer Cell Binding Ability of Ab-HLPN in which an Anti-PSMA Antibody is Modified It was confirmed whether Ab-HLPN in which other types of antibodies were modified also binds well to cancer cells in addition to the anti-Claudin3 antibody-modified Ab-HLPN prepared in Example 1.

Specifically, an anti-PSMA antibody-modified Ab-HLPN was prepared in the same manner and conditions as the method of preparing Ab-HLPN in Example 1, except that as the used antibody, an anti PSMA antibody was used instead of an anti Claudin3 antibody. Thereafter, the ability to bind to a PSMA-overexpressing cell line LNcaP b and a PSMA-non-expressing cell line PC3 was confirmed in the same manner as in Experimental Example 1.

Figure 19:
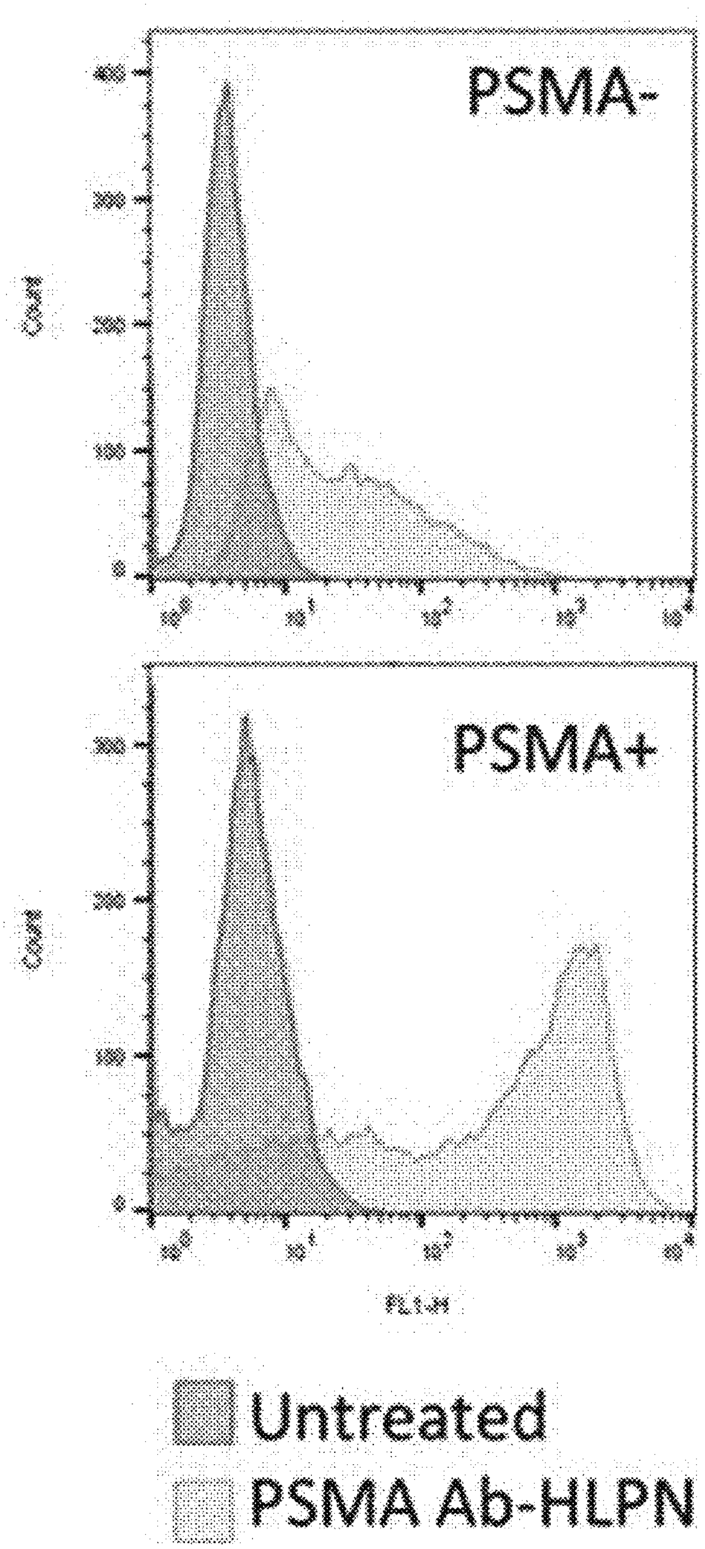
FIG. 19 illustrates the measurement of the ability of Ab-HLPN to which an anti-PSMA antibody is bound to bind to PSMA-overexpressing or non-expressing cancer cells by flow cytometry, and is a set of views confirming that an anti-PSMA antibody-bound Ab-HLPN can bind well to PSMA-overexpressing cells.

As a result, as illustrated in FIG. 19, it was confirmed that PSMA Ab-HLPN binds well to PSMA-overexpressing cancer cells. The above results suggest that various types of cancers can be treated by surface modification of antibodies that bind to antigens specifically expressed on cancer cells.

<Example 2> Preparation of Lipid-Photothermal Nanoparticle Having Antibody Site-Specifically Conjugated to Surface Thereof Hereinafter, after an antibody modified so as to have a free thiol group was prepared, a phospholipid-photothermal nanoparticle, in which the antibody was site-specifically conjugated to the phospholipid membrane surface of the nanoparticle, was prepared to confirm the cancer cell-target photothermal therapeutic effect of the same.

<Experimental Example 11> Preparation of h4G3Cys-Conjugated Lipid-Polydopamine Hybrid Nanoparticles (h4G3Cys-Conjugated LPNs, C-LPNs)

In order to prepare phospholipid-photothermal nanoparticles in which a Claudin3-specific antibody is site-specifically conjugated to the surface of the phospholipid membrane, an anti-Claudin3 antibody variant and lipid-photothermal nanoparticles (LPNs) including a maleimide group were prepared to conjugate the two. The anti-Claudin3 antibody variant is site-specifically conjugated to the nanoparticle surface by binding a free thiol group added through genetic mutation to the maleimide of LPN (FIG. 20).

<11-1> Preparation of Cysteine-Substituted Anti-Claudin3 Human Monoclonal Antibody An anti-Claudin3 antibody variant (h4G3cys) capable of site-specifically conjugating to nanoparticles was prepared by selecting h4G3 as an anti-Claudin3 antibody that targets Claudin3 and substituting the 125 glutamine residue (that is, the 17 glutamine residue of a light chain constant region) of the light chain of h4G3 with cysteine. In order to establish CHO-S cells stably expressing h4G3cys, a light chain including a cysteine mutant; and a heavy chain of h4G3 were cloned into a Freedom pCHO 1.0 vector (Thermo Fisher Scientific, Inc.), and then transfected into Freedom CHO-S cells (Thermo Fisher Scientific, Inc.). The transfected CHO-S cells were cultured on an orbital shaker (130 rpm) in a humidified environment at 37° C. and 8% $CO_2$ for 2 weeks, and treated with 4 g/L glucose on days 3 and 5 and 6 g/L on day 7. A bound antibody was eluted and washed by loading the supernatant of a culture isolate into a MabSelect SuRe Protein A resin (GE Healthcare, Piscataway), and the antibody was neutralized with 1 mol/L Tris-HCl (pH 8.0). Buffer exchange and concentration were performed using an Amicon Ultra-15 centrifugal concentrator (Merck Millipore).

<11-2> Evaluation of Antigen-Binding Ability of h4G3Cys Antibody

It was confirmed whether an anti-Claudin3 antibody variant h4G3cys prepared in Example 11-1 showed similar binding patterns in various cancer cell lines compared to an existing antibody h4G3cys.

Specifically, after a Claudin3-non-expressing cell line (TOV-112D, Hs578T): a cell line (claudin-stable expressing TOV-112D, CLDN3/TOV-112D) modified so as to express Claudin3; and a Claudin3-expressing cell line (T47D, OVCAR-3, Caov-3, MCF-7) were cultured with 2.5 μg/Ml h4G3 or h4G3cys antibody for 1 hour, the antibody bound to cancer cells was detected by flow cytometry using an FITC-conjugated goat anti-human IgG secondary antibody.

Figure 21:
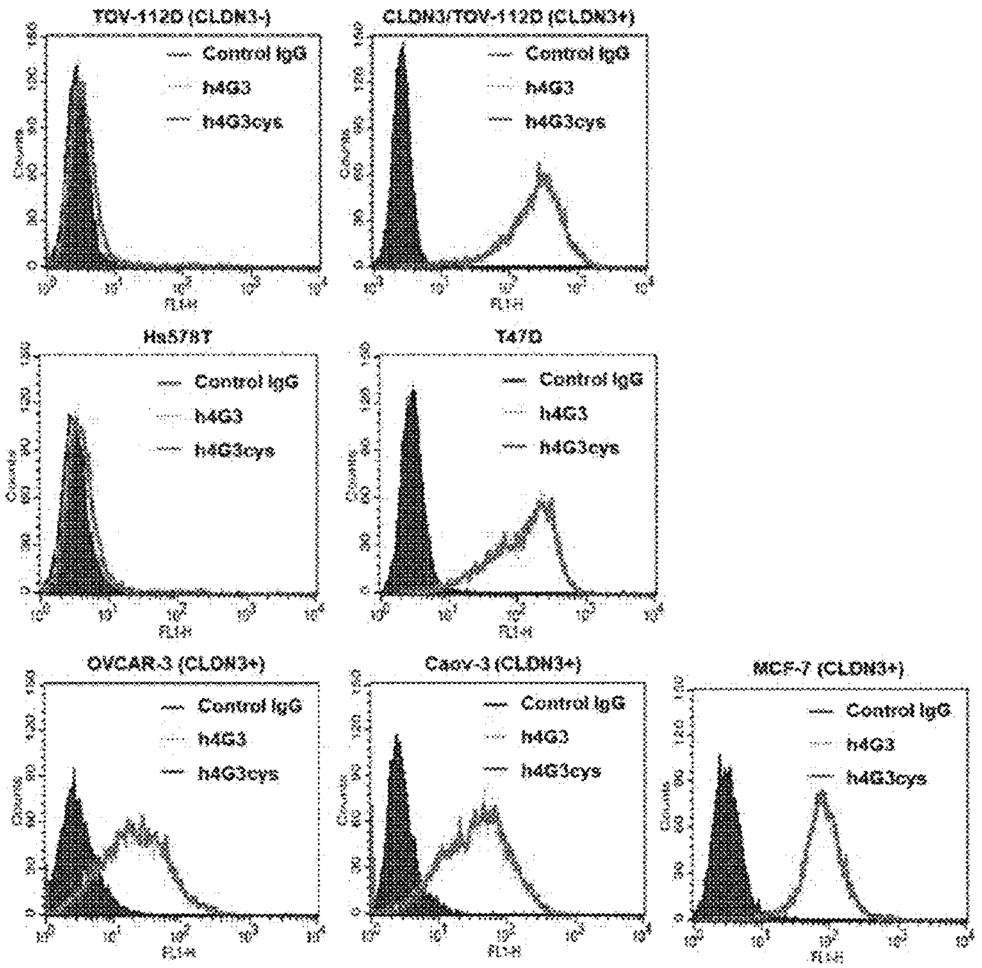
FIG. 21 illustrates the comparison of the cancer cell binding patterns of an anti-Claudin3 antibody (h4G3) and a modified anti-Claudin3 antibody (h4G3cys), and is a set of views confirming that cysteine substitution does not affect cancer cell binding ability.

As a result, it was confirmed that compared to an existing antibody h4G3, h4Gcys, in which the Q125 residue was substituted with cysteine, exhibited a binding pattern similar to that of h4G3 in all cell lines (FIG. 21). The above results indicate that the cysteine substitution of the anti-Claudin3 antibody variant does not change the ability to bind to Claudin3.

<11-3> Evaluation of Thiol Reactivity of h4G3Cys Antibody

Genetically engineered h4G3cys has the Q125 residue replaced with cysteine and two free-thiol groups per antibody, compared to h4G3. To specifically confirm this, thiol reactivity was evaluated by measuring 4-mercaptopyridine by UV-Vis spectroscopy.

Specifically, a 7 μmol/L purified h4G3cys solution was reacted with a 500 μmol/L solution of 4,4'-dithiopyridine (4-PDS) in a 0.1 mol/L sodium phosphate buffer (pH 6.0) at room temperature for 15 minutes. After the reaction was completed, the absorbance was measured at 324 nm with a UV-Vis spectrometer (Ultrospect 2100 Pro). A standard curve was obtained by titrating N-acetyl-L-cysteine with 4-PDS.

Figure 22:
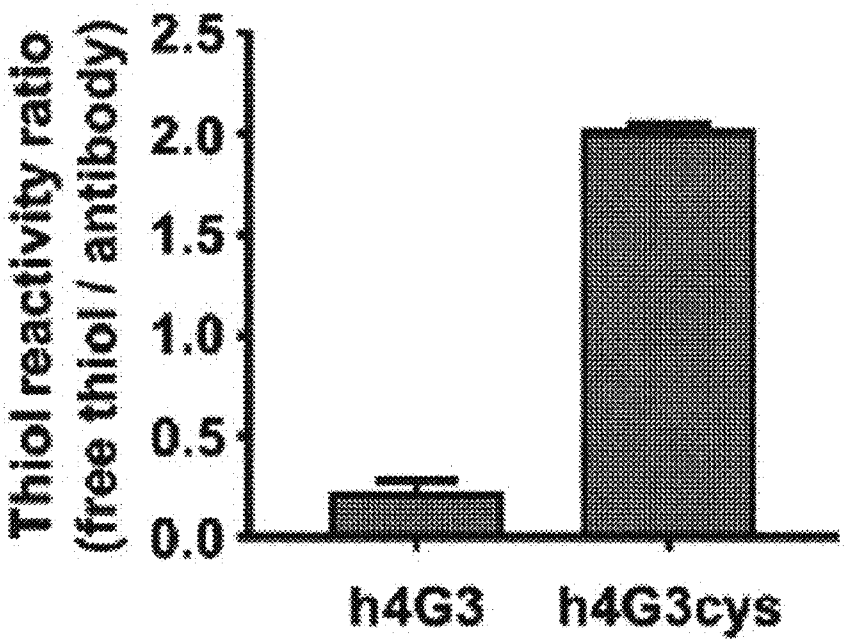
FIG. 22 illustrates the comparison of thiol reactivity of the h4G3 antibody and the h4G3cys antibody, and is a view confirming that the thiol reactivity of h4G3cys is higher than that of h4G3.

As a result of the experiment, it was shown that h4G3cys engineered so as to include a cysteine residue was 9.5-fold more thiol-reactive than h4G3 (FIG. 22). That is, the above results show that the anti-Claudin3 antibody variant h4G3cys according to the present invention has more free thiol groups than h4G3.

<11-4> Evaluation of Site-Specific Conjugation Ability of h4G3Cys Antibody

Next, western blotting using streptavidin horseradish peroxidase (SHRP) was performed to compare the ability of maleimide-PEG2-biotin to site-specifically conjugate to a thiol group of h4G3cys or a light chain of h4G3. Specifically, the degree of binding of maleimide-PEG2-biotin to h4G3cys or h4G3 was compared by reacting h4G3cys or h4G3 with maleimide-PEG2-biotin using an EZ-Link Maleimide-PEG Solid Phase Biotinylation Kit (Thermo Fisher Scientific) according to the manufacturer's instructions and detecting biotin by western blotting using SHRP.

Figure 23:
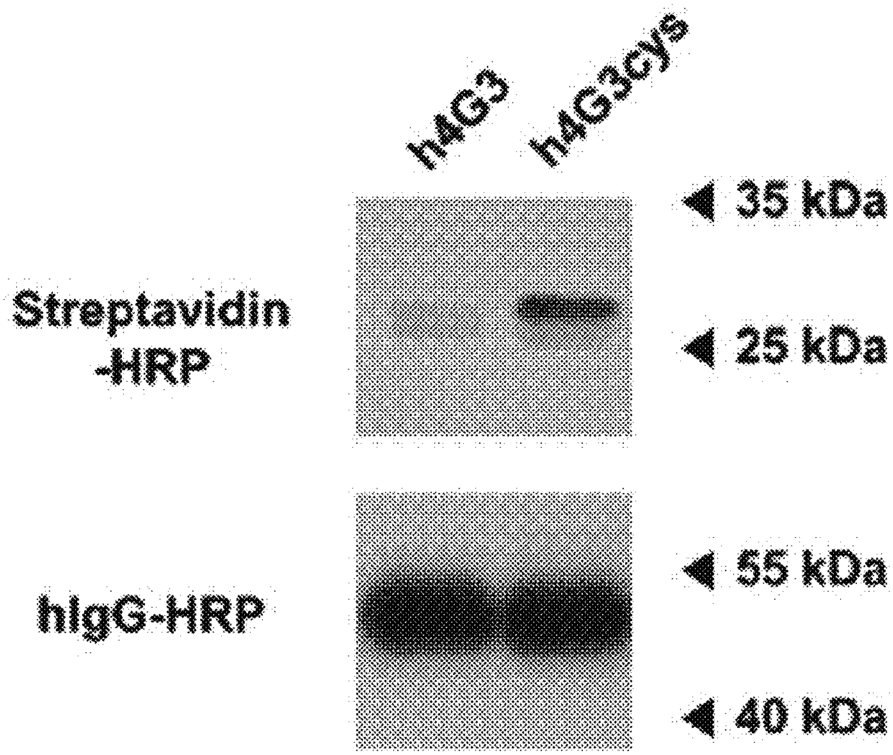
FIG. 23 illustrates the comparison of the ability of the h4G3 antibody and the h4G3cys antibody to bind to maleimide-PEG2-biotin, and is a view confirming that the h4G3cys antibody more strongly binds to maleimide.

As a result, it could be confirmed that maleimide-PEG2-biotin had higher binding strength to h4G3cys than h4G3 (FIG. 23). The aforementioned results show that h4G3cys, in which the Q125 residue is replaced with cysteine, binds to maleimide more effectively than h4G3.

Figure 24:
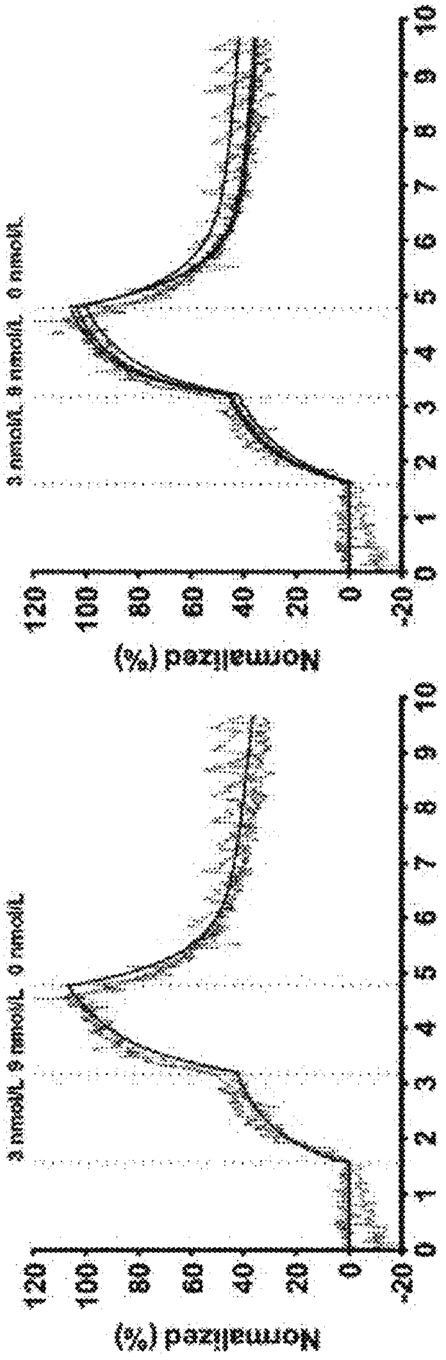
FIG. 24 is a view confirming the binding affinity of the h4G3cys antibody to CLDN3/TOV-112D (TOV-112D cells modified to express Claudin3). Each curve exhibits each independent experimental result.
Figure 25:
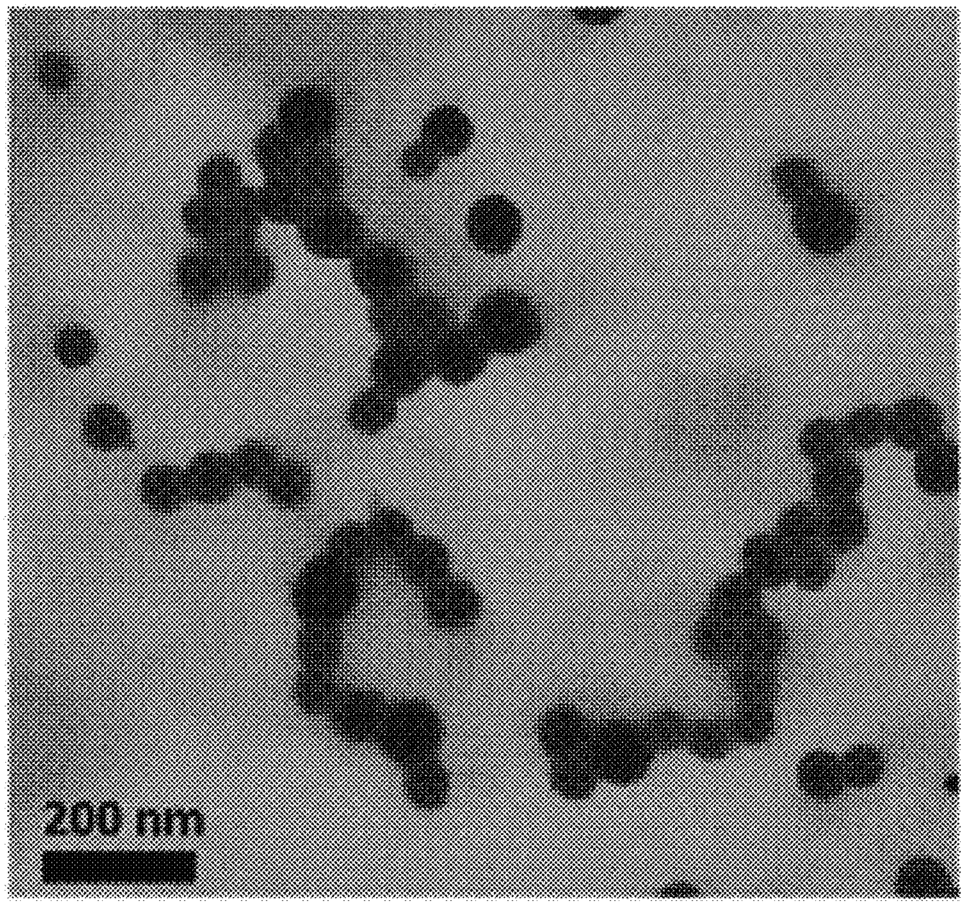
FIG. 25 is a view confirming the morphology of polydopamine nanoparticles (PNs) by a transmission electron microscope.
Figure 26:
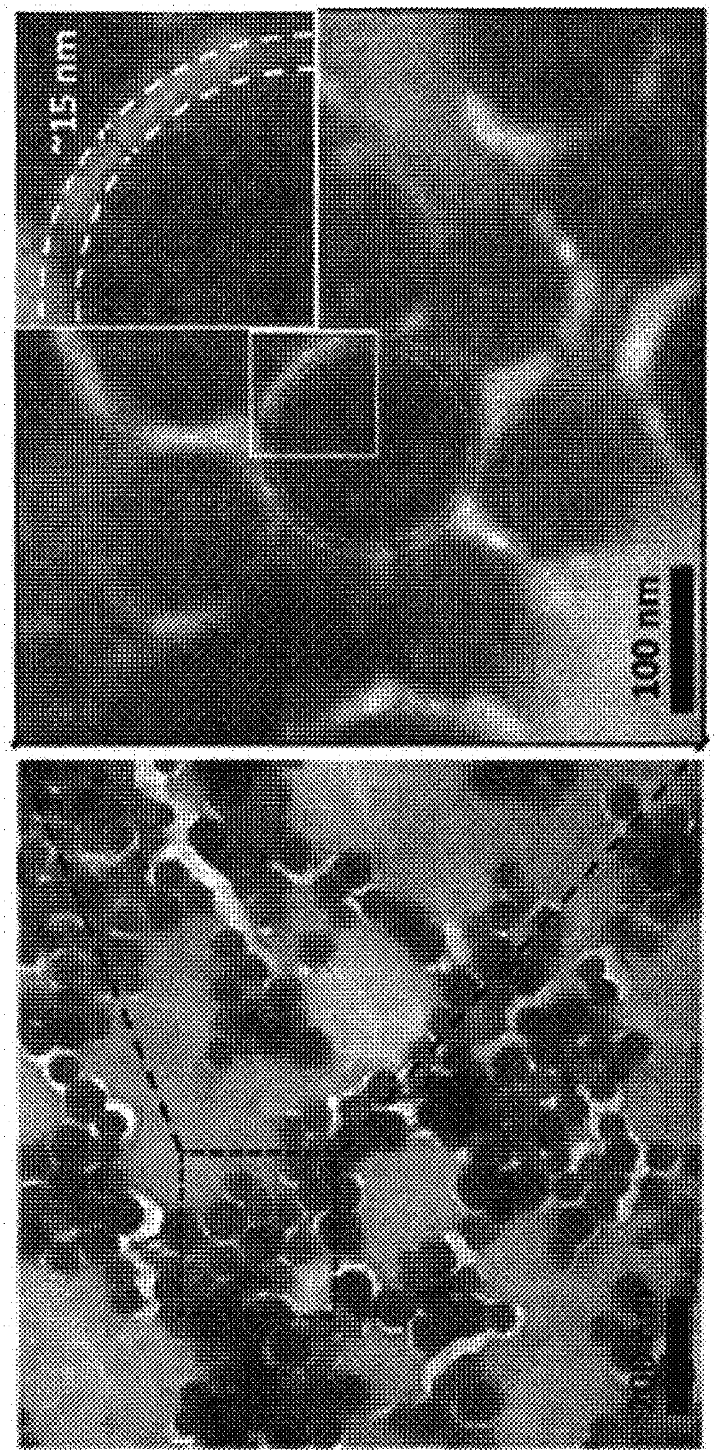
FIG. 26 is a set of views confirming the morphology of C-LPN by a transmission electron microscope.

Further, as a result of treating TOV-112D cells (CLDN3/TOV-112D) engineered so as to express Claudin3 with FITC-labeled h4G3cys, and then measuring fluorescence by FITC, the binding affinity of h4G3cys for CLDN3/TOV-112D was shown to be 5.24 nmol/L in a 'one-to-one two-state' model (A+B↔AB↔AB*) reflecting the state in which a ligand and a target were bound to each other, and then rearranged as a stronger binding complex (left side of FIG. 24), and a first binding affinity ($K_{D1}$) and a second binding affinity ($K_{D2}$) were shown to be 11.00 nmol/L and 0.58 nmol/L, respectively in an 'one-to-two' model ($A+B_1 \leftrightarrow AB_1+B_2 \leftrightarrow AB_1B_2$) in consideration of avidity due to the bivalent properties that the antibody has a bivalent ability to bind to a target (right side of FIG. 24).

<11-5> Preparation of h4G3Cys-Bound LPN (C-LPN)

The phospholipid-photothermal nanoparticles (h4G3cys-conjugated LPNs, C-LPNs) in which h4G3cys was site-specifically conjugated to the surface of the phospholipid membrane were prepared by binding the anti-Claudin3 antibody variant h4G3cys prepared in Example 11-1 to lipid polydopamine hybrid nanoparticles.

A polydopamine nanoparticle (PN) was prepared according to Experimental Example 1-1, but the pH was adjusted to pH 9.6 by slowly adding a 1 N sodium hydroxide solution dropwise to the dopamine hydrochloride solution.

First, PN was coated with maleimide-functionalized lipid using a co-extrude technique through the following process: DPPC, DPPG, and DSPE-PEG2000-maleimide were dissolved in a solvent (chloroform:methanol=4:1, v v) at a molar ratio of 7:3:0.1. However, in experiments for nanoparticle tracking, DSPE-PEG2000-FITC was added at a rate of 0.02% (mol/mol) of total lipids, and in in vivo distribution confirmation experiments, DSPE-PEG2000-Cy5 was added at a rate of 0.1% (mol/mol) of total lipids. Subsequently, the lipid solution was evaporated in a vacuum state using a rotary vacuum concentrator to prepare a lipid thin film, and the lipid thin film was hydrated with 1 mL of a 10 mg/mL PN solution. A hybrid lipid polydopamine nanoparticle (LPN) was obtained by allowing the resulting solution to pass through a 0.4 μm polycarbonate membrane (Merck Millipore).

Next, the h4G3cys antibody was site-specifically conjugated to the maleimide of the lipid-polydopamine hybrid nanoparticles through the following process: 100 μL of isotype IgG (Q125C: IgG genetically engineered so as to express cysteine in a Q125 residue) or h4G3cys (10 mg/mL) was mixed with 1 mL of LPN and allowed to react at 4° C. overnight. After the reaction was completed, the reaction product was centrifuged at 13,000×g for 10 minutes, a pellet was rehydrated with 1 mL of 5% glucose, and then extruded using a 0.4 μm polycarbonate membrane. The resulting isotype IgG antibody-bound LPN (IG-LPN) and h4G3cys antibody-bound LPN (C-LPN) were collected and stored at 4° C. A schematic view of the manufacturing process and the prepared C-LPN is illustrated in FIG. 20.

<Experimental Example 12> Characteristic Analysis of C-LPN

The physical characteristics, elements, and photothermal ability of C-LPN prepared through Experimental Example 11 were confirmed.

<12-1> Confirmation of Morphology and Size of C-LPN

First, the morphology of C-LPN was analyzed using a transmission electron microscope (TEM). Nanoparticles were briefly stained with a 1% uranyl acetate solution before observation with TEM.

As a result of observation, it was confirmed that both PN (FIG. 25) and C-LPN nanoparticles (FIG. 26) had an overall spherical morphology and a uniform surface. In particular, in the case of C-LPN, it could be confirmed that the dark spherical particles were covered with a bright thin film (right side of FIG. 26). The thin film had a thickness of about 15 nmol/L, and from this, it could be directly confirmed that PN was successfully coated with a lipid thin film layer.

Figure 27:
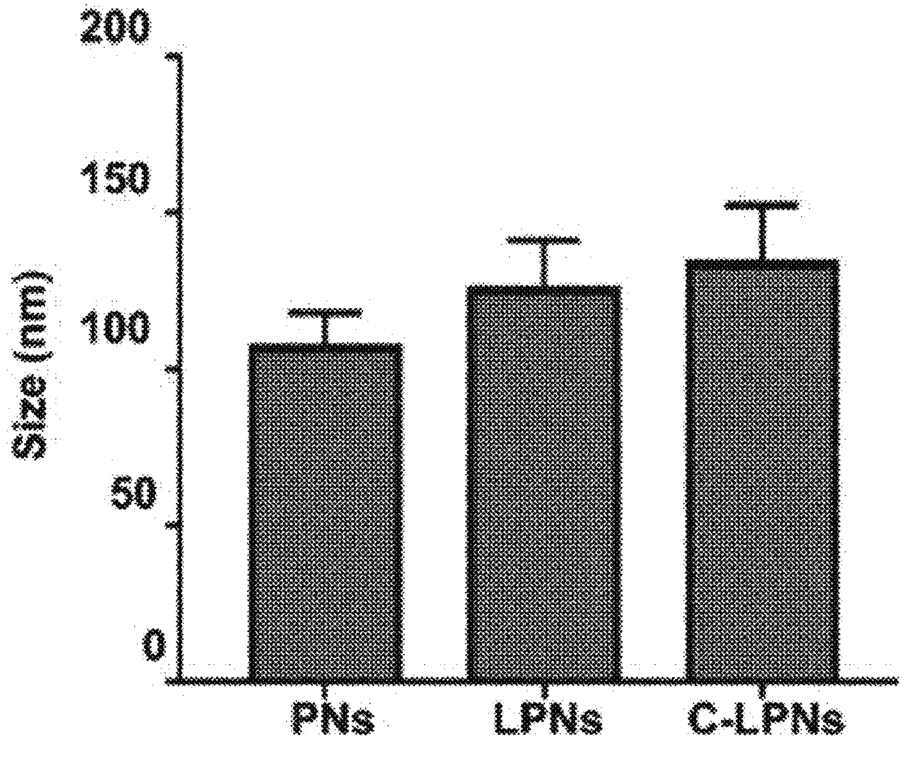
FIG. 27 illustrates the composition of particles sizes of PN, LPN, and C-LPN using dynamic light scattering, and is a view confirming that there was no significant difference in average size.

In addition, as a result of comparing the sizes of the particles using dynamic light scattering, it was confirmed that there was no significant difference in the average size of LPN compared to PN even though LPN was coated with a thin lipid thin film layer (FIG. 27).

<12-2> Analysis of Constituent Elements of C-LPN

Figure 28:
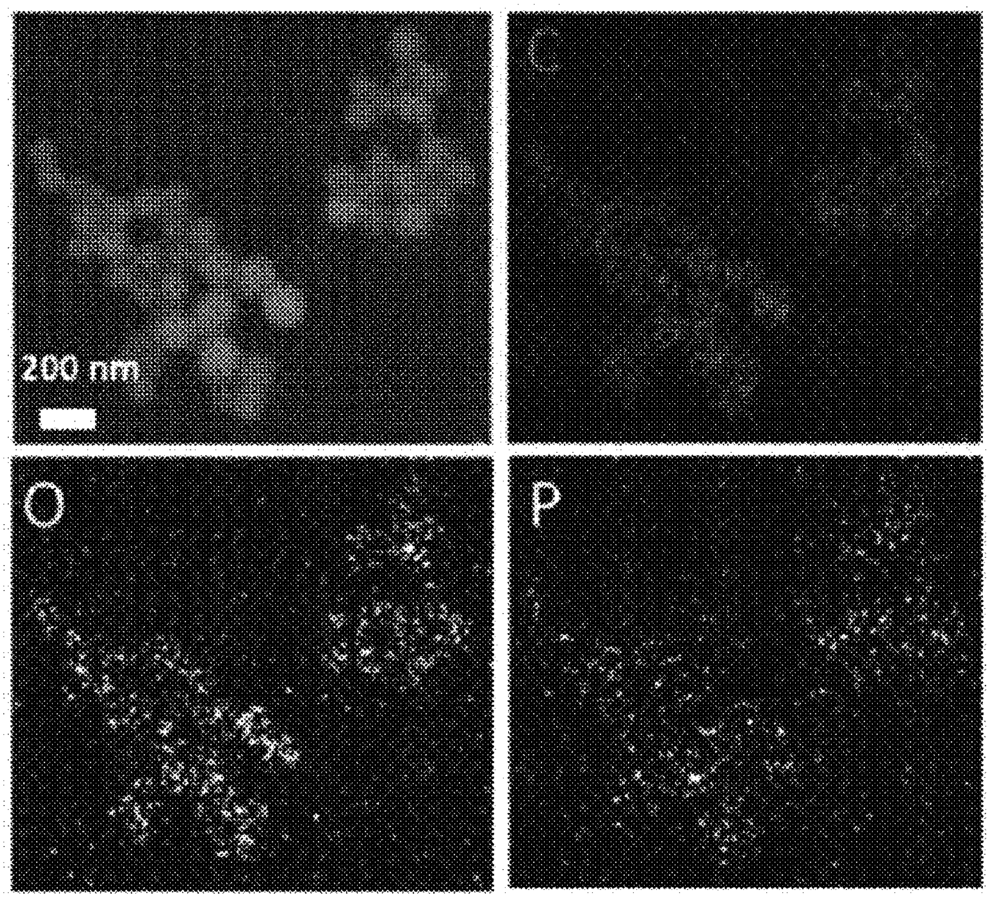
FIG. 28 is a set of views confirming the constituent elements of C-LPN (C: carbon, O: oxygen, and P: phosphorus).

Next, elemental mapping was performed using energy dispersive X-ray spectroscopy-scanning transmission electron microscopy (EDSSTEM) to analyze the elements present in C-LPN. As a result, it could be again confirmed that PN was coated with lipids due to the presence of carbon and oxygen in the PN basic structure, particularly the presence of phosphorus (FIG. 28).

Figure 29:
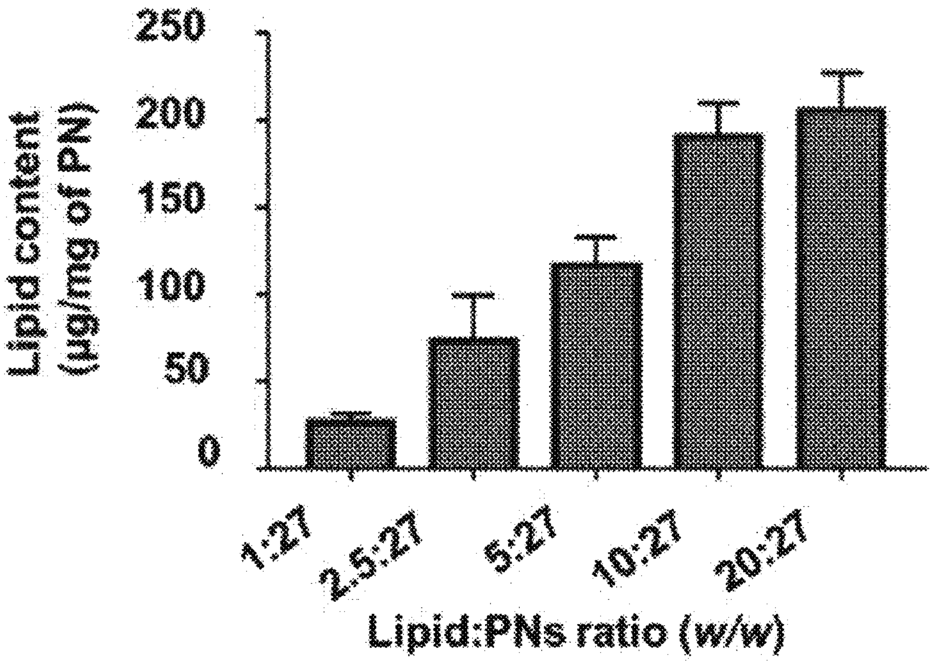
FIG. 29 is a view confirming the lipid content according to the lipid: PN weight ratio (w/w) of C-LPN.
Figure 30:
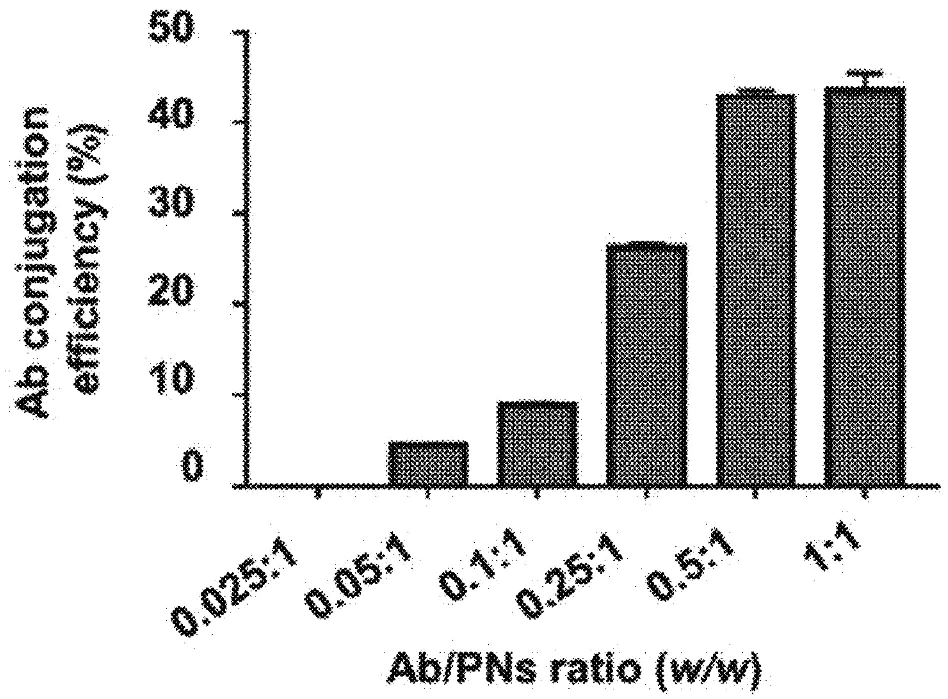
FIG. 30 is a view confirming the Ab conjugation efficiency according to the antibody (Ab): PN weight ratio (w/w) of C-LPN.

Furthermore, as a result of quantifying the phosphorus content of each C-LPN particle through phosphate assay, it was found that the lipid content of particles was highest at a ratio of lipid:PN of 10:27 (w/w), and no significant increase in the lipid content of particles was observed even though the proportion of lipid was increased more than the ratio (FIG. 29). Subsequently, as a result of measuring the content of antibodies immobilized on the nanoparticles using Cedex Bio Analyzer (Roche), it was found that the antibody binding efficiency increased with increasing antibody concentration and did not increase any more when the ratio of antibody:PN reached 0.5:1 (w/w) (FIG. 30).

<12-3> Analysis of Photothermal Ability of C-LPN

Figure 31:
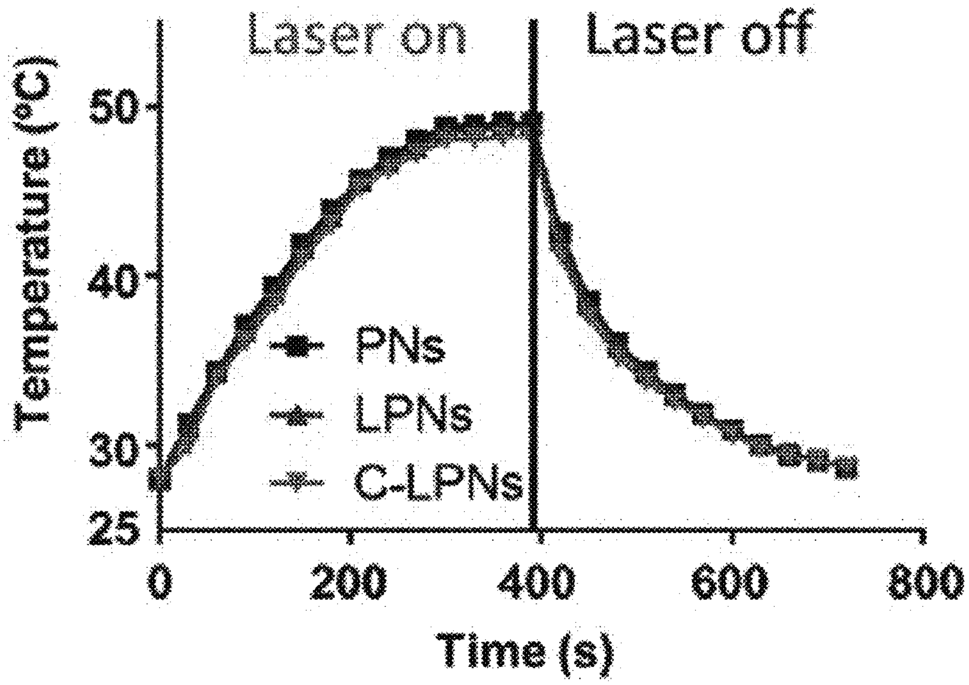
FIG. 31 is a view measuring the change in temperature over time after irradiating PN, LPN, and C-LPN with near-infrared rays.
Figure 32:
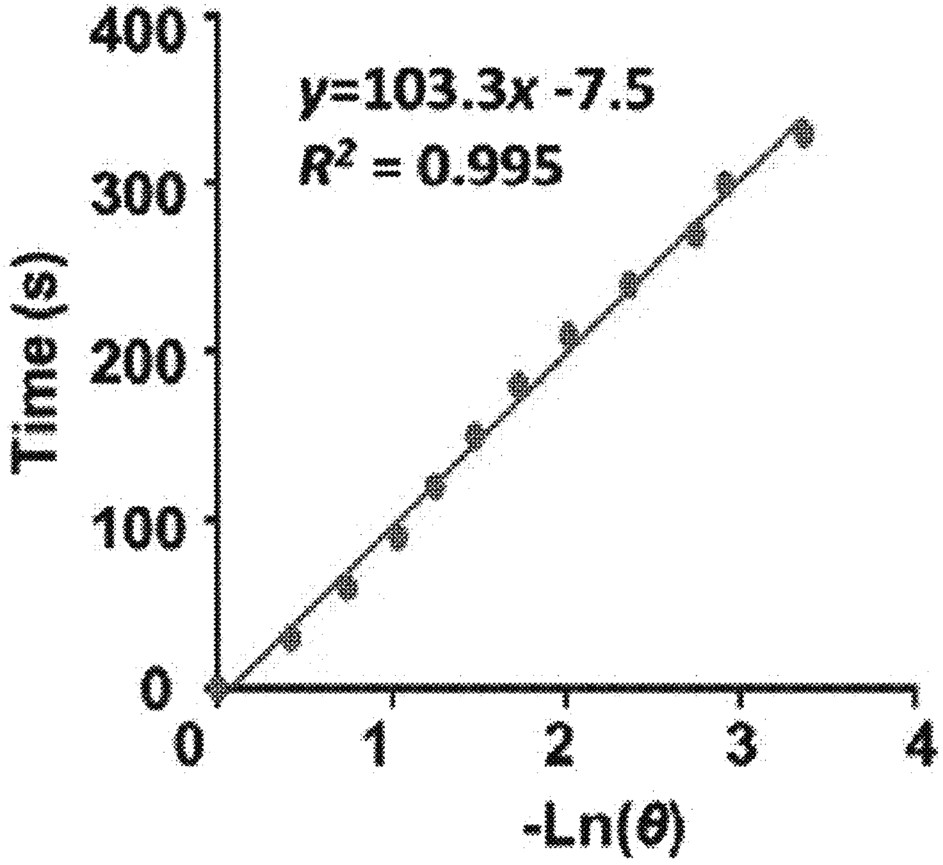
FIG. 32 is a graph showing-Lnθ obtained from the cooling interval of C-LPN over time.
Figure 33:
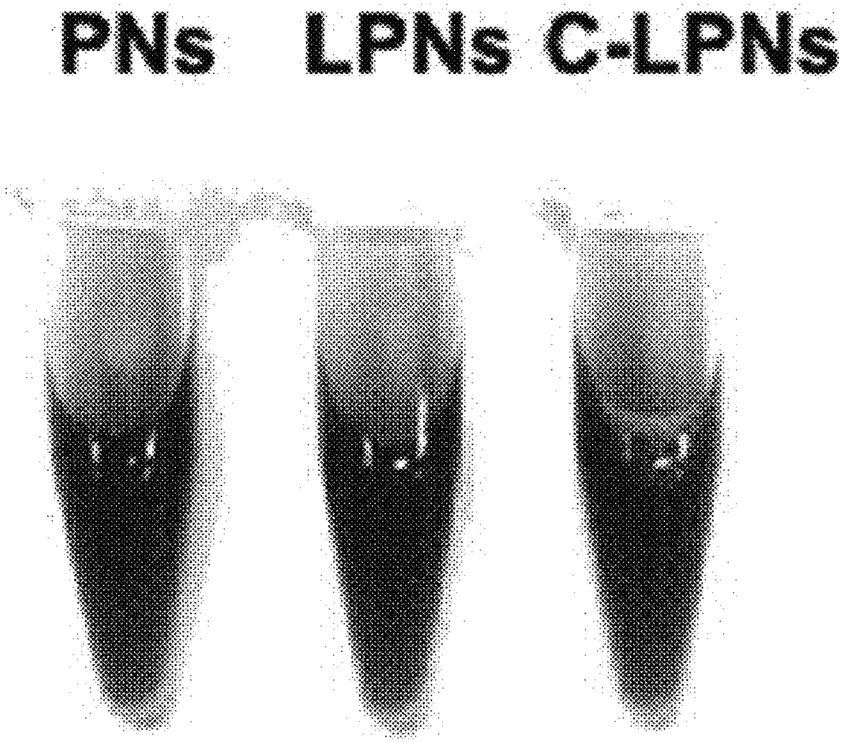
FIG. 33 is a view confirming the change in appearance after adding PN, LPN, or C-LPN to the culture medium.

Subsequently, the photothermal ability of the nanoparticles was confirmed by measuring the change in temperature before and after the irradiation with near-infrared rays according to Experimental Example 6. As a result, at a concentration of 400 μL/mL, the maximum steady-state temperature and ambient temperature of C-LPN were 48.2° C. and 28.0° C., respectively (FIG. 31). FIG. 32 illustrates a graph showing-Lnθ obtained from the cooling interval of C-LPN over time. Finally, no difference in appearance was found when PN, LPN and C-LPN were added to the culture medium and compared by the naked eye (FIG. 33).

<Experimental Example 13> Evaluation of Ability of C-LPN to Bind to Cancer Cells The ability of the C-LPN prepared in Experimental Example 11 to bind to cancer cells was confirmed using a Claudin3-overexpressing cell line T47D and a Claudin3-non-expressing cell line Hs578T.

<13-1> Evaluation of Ability of C-LPN to Bind to Cancer Cells Using Flow Cytometry An analysis of cancer cell binding ability using flow cytometry was performed in the same manner as in Experimental Examples 1 and 2, but cells were treated with FITC-labeled IG-LPN or C-LPN at a concentration of 50 μg/ml in order to compare the binding ability of IG-LPN and C-LPN.

Figure 34:
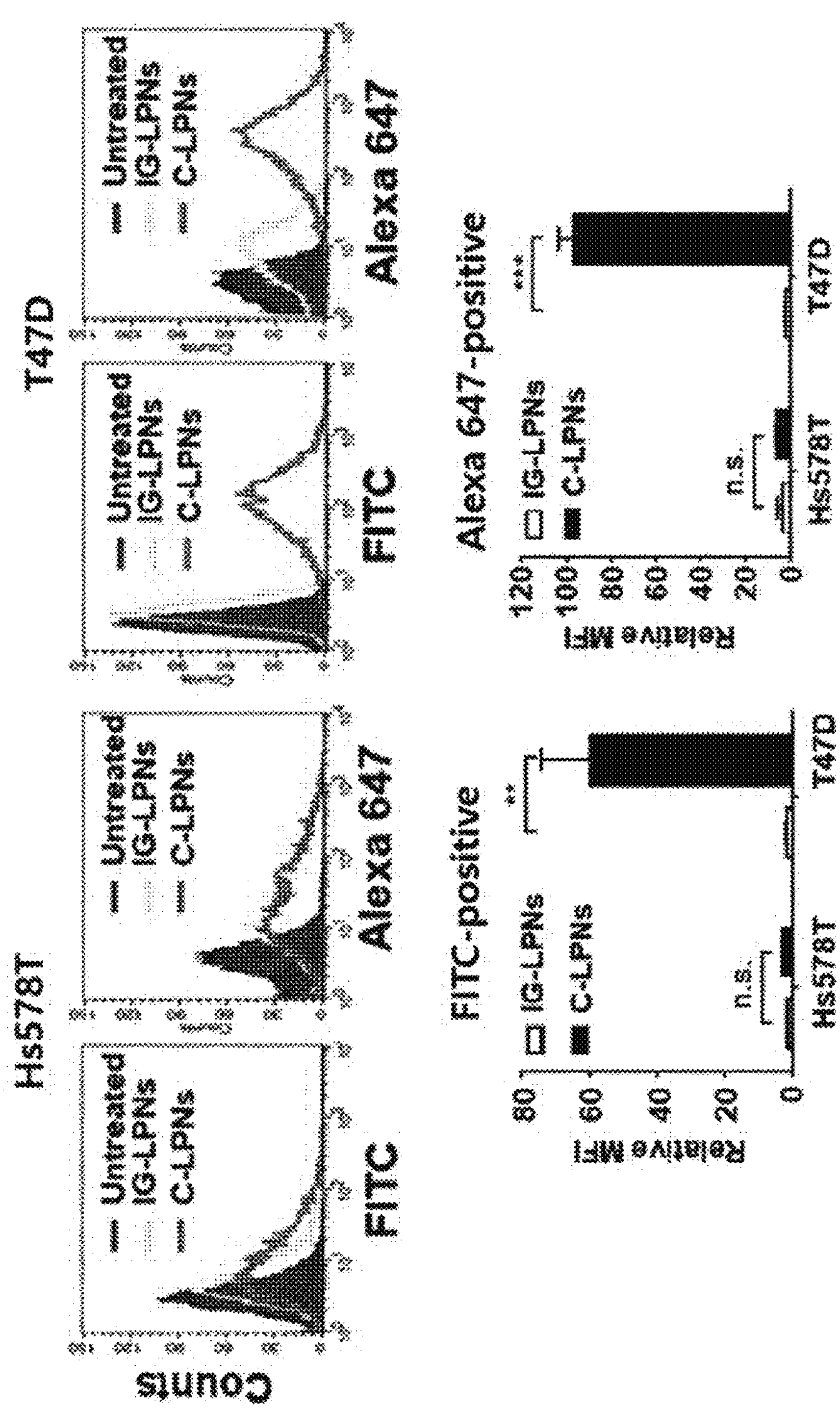
FIG. 34 illustrates the comparison of the ability of isotype IgG antibody-bound LPN (IG-LPN) and C-LPN to bind to cancer cells by flow cytometry, and is a set of views confirming that the ability of C-LPN to bind to T47D cells which are Claudin3-expressing cells is higher than that of IG-LPN.

As a result, it was confirmed that in the case of Hs578T cells that do not express Claudin3, there was no difference in binding ability between IG-LPN and C-LPN, but in the case of T47D cells expressing Claudin3, the binding ability of C-LPN was 33.7-fold to 53.3-fold higher than that of IG-LPN (FIG. 34).

<13-2> Evaluation of Ability of C-LPN to Bind to Cancer Cells Using Fluorescence Microscope To further confirm the cell surface binding of the antibody, immunostaining was performed according to Experimental Example 5-2. Specifically, Hs578T cells and T47D cells were inoculated into a 4-well plate, and when a confluence of 80% was reached, the 4-well plate was treated with FITC-labeled IG-LPN or C-LPN at 37° C. for 1 hour. Subsequently, the cells were cultured and fixed with 4% formaldehyde for 15 minutes, and cultured with Alexa 555-conjugated anti-human IgG antibody (Thermo Fisher Scientific) for 1 hour. The nuclei of the cells were stained with Hoechst 33345 (Invitrogen), and the cells were observed with an LSM 700 ZEISS laser-scanning confocal microscope (Carl Zeiss).

Figure 35:
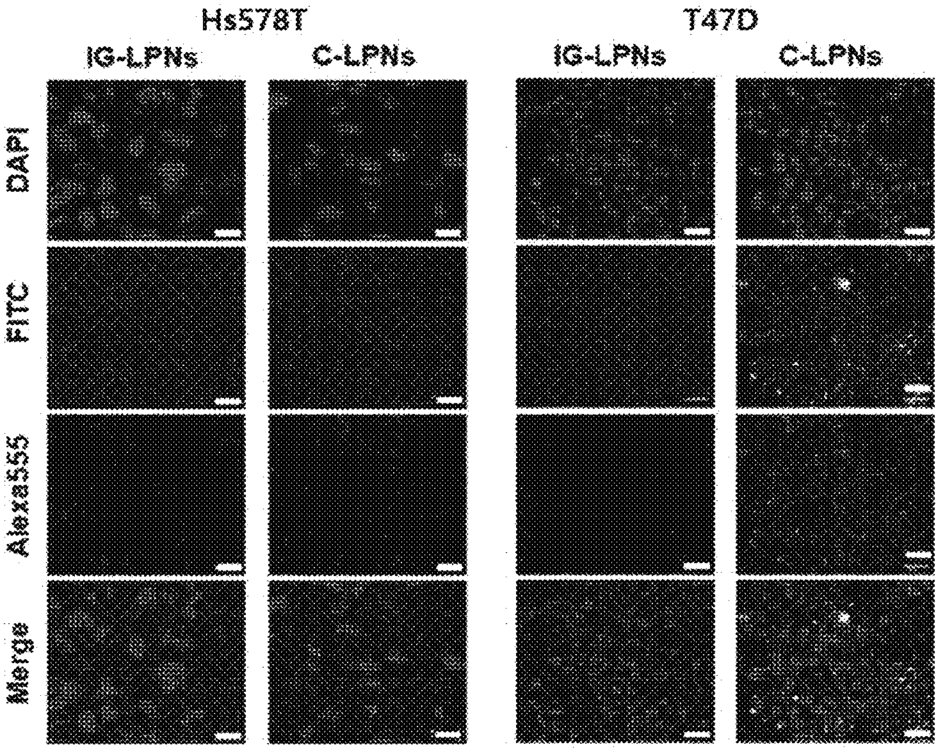
FIG. 35 confirms the ability of IG-LPN and C-LPN to bind to cancer cells by a fluorescence microscope, and is a set of views confirming that the ability of C-LPN to bind to T47D cells is higher than that of IG-LPN.

As a result, it could be confirmed that when Hs578T cells were treated with IG-LPN or C-LPN, there was no difference, but when T47D cells were treated with IG-LPN, no fluorescence signal appeared, whereas when T47D cells were treated with C-LPN, strong fluorescence signals appeared (FIG. 35). The aforementioned results demonstrate that the h4G3cys antibody-bound nanoparticles effectively bind to Claudin3-expressing cancer cells.

<13-3> Evaluation of Ability of C-LPN to Bind to Cancer Cells Using Transmission Electron Microscope The ability of C-LPN to bind to cancer cells was confirmed using a transmission electron microscope (TEM) in the same manner as in Experimental Example 5-1. T74D or Hs578T cells were cultured in a 100 mm culture dish to reach about 80% of the area of the culture dish, and then treated with C-LPN at a concentration of 300 μg/ml.

Figure 36:
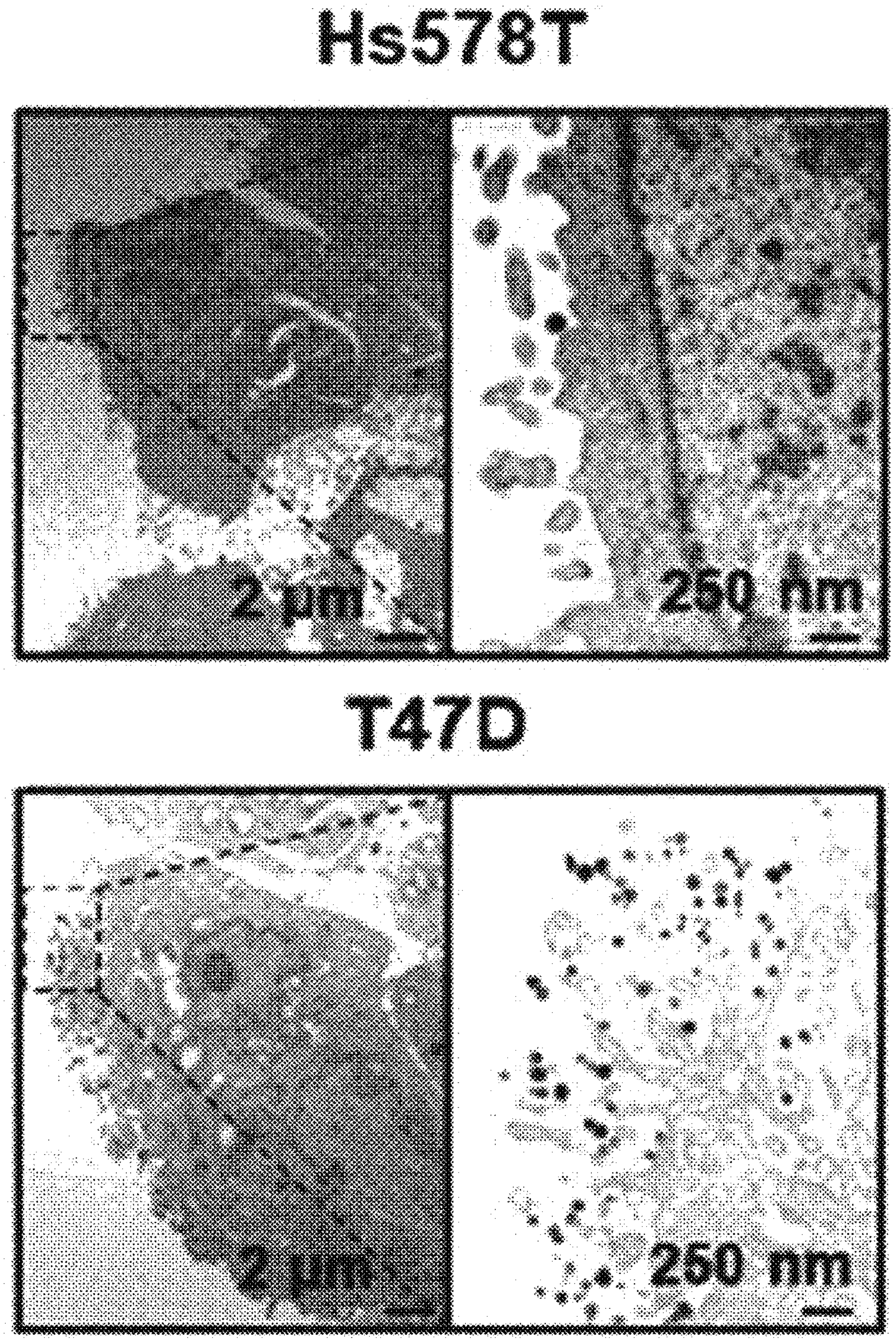
FIG. 36 confirms the ability of IG-LPN and C-LPN to bind to cancer cells by a transmission electron microscope, and is a set of views confirming that the ability of C-LPN to bind to T47D cells is higher than that of IG-LPN.

As a result of analyzing TEM images, the binding of C-LPN as well as IG-LPN could not be confirmed in Hs578T cells, but it could be confirmed that C-LPN bound to the cell surface and the cell pellet were stained darker when T47D cells were treated with C-LPN than when T47D cells were treated with IG-LPN (FIG. 36). The aforementioned results demonstrate that the h4G3cys antibody-bound nanoparticles effectively bind to Claudin3-expressing cancer cells as in Experimental Example 13-2.

<13-4> Macroscopic Evaluation of Ability of C-LPN to Bind to Cancer Cells

Finally, it was confirmed by the naked eye whether C-LPN binds to each cancer cell by culturing T74D or Hs578T cells with C-LPN. Specifically, each cell was treated with IG-LPN or C-LPN for 1 hour and then centrifuged to observe the color of a cell pellet.

Figure 37:
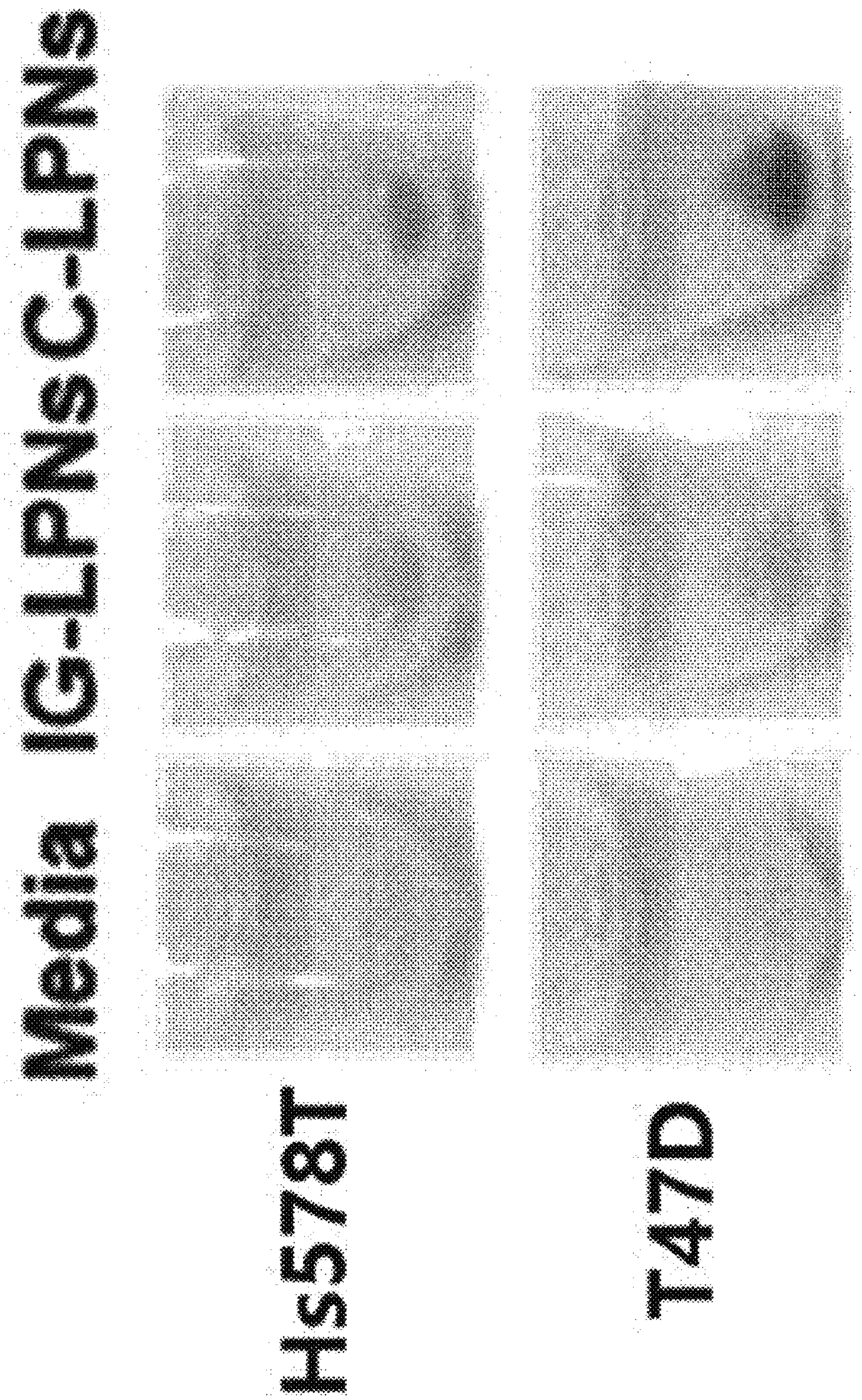
FIG. 37 illustrates the comparison of the cell pellet colors by the naked eye after treating an Hs578T cell which is a Claudin3-non-expressing cells and T47D which is a Claudin3-expressing cell with IG-LPN or C-LPN, respectively, and is a set of views confirming that the ability of C-LPN to bind to T47D cells is higher than that of IG-LPN.

As a result, it could be confirmed that Hs578T cells did not show any significant difference in cell pellets when treated with IG-LPN or C-LPN, but when T47D cells were treated with C-LPN compared to IG-LPN, dark brown C-LPN bound to the cells, and thus the cell pellet showed a dark color (FIG. 37).

<Experimental Example 14> Evaluation of Photothermal Therapeutic Effect of C-LPN In order to evaluate the photothermal therapeutic effect of C-LPN, the change in temperature and viability of cancer cells over time were evaluated by irradiating cancer cells treated with C-LPN particles with near-infrared rays.

<14-1> Measurement of Change in Temperature of Cancer Cells Over Time of Irradiation with Near-Infrared Rays The photothermal therapeutic effect of C-LPN depends on the Claudin3 expression level of cancer cells. Therefore, in order to confirm whether C-LPN exhibits a photothermal effect in Claudin3-expressing cells, the change in temperature of cancer cells over time was measured by treating T74D and Hs578T cells with IG-LPN or C-LPN, and then irradiating the cells with near-infrared rays according to Experimental Example 6-1.

Figure 38:
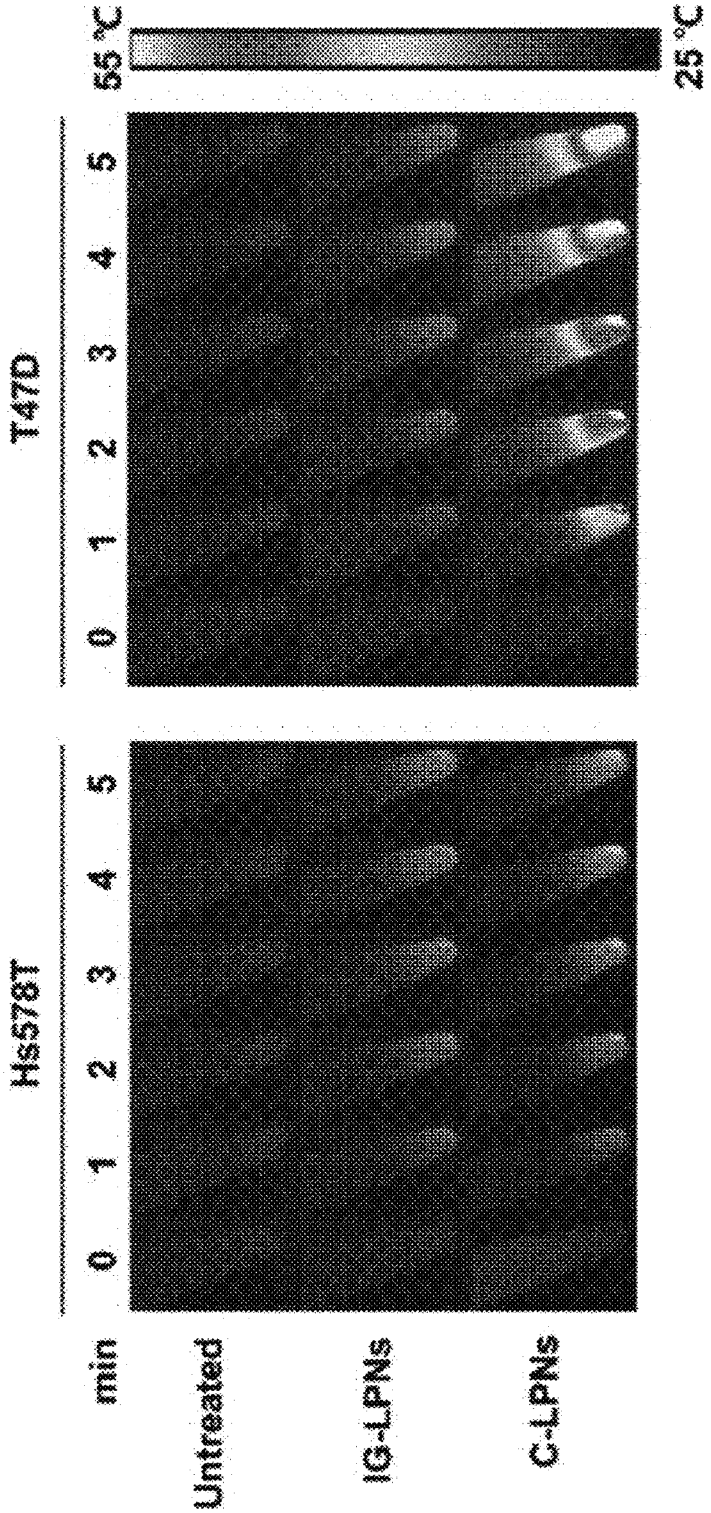
FIG. 38 is a set of views confirming the change in temperature by a thermal imaging camera by treating Hs578T cells or T47D cells with IG-LPN or C-LPN, and then irradiating the cells with near-infrared rays.
Figure 39:
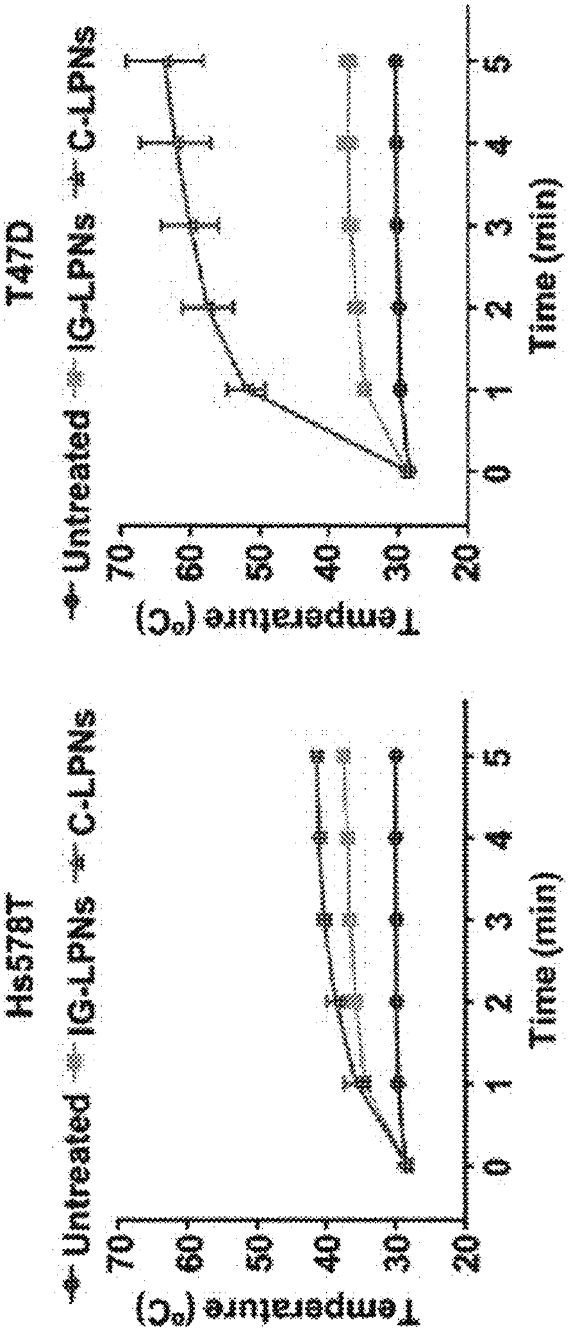
FIG. 39 is a set of views measuring the change in temperature by treating Hs578T cells or T47D cells with IG-LPN or C-LPN, and then irradiating the cells with near-infrared rays.

As a result, it could be confirmed that similarly to the ability of C-LPN to bind to cancer cells (Experimental Example 13), there was no difference in temperature between groups treated with IG-LPN and C-LPN even though Hs578T cells were irradiated with near-infrared rays, but in the case of T47D cells, the group treated with C-LPN responded to the NIR irradiation to increase the cell temperature, whereas the IG-LPN treatment group had no change in temperature even though irradiated with NIR (FIG. 38). As a result of quantifying the change in temperature, it could be confirmed that when Hs578T cells were treated with C-LPN, the maximum temperature did not exceed 40° C. even when irradiated with near-infrared rays, whereas when T47D cells treated with C-LPN were irradiated with near-infrared rays, the temperature was shown to increase to 60° C. or higher, and thus the temperature was 26.5° C. or higher compared to the IG-LPN treatment group (FIG. 39). The aforementioned results show that C-LPN according to the present invention can effectively induce a photothermal effect specifically in Claudin3-expressing cancer cells.

<14-2> Measurement of Viability of Cancer Cells According to Irradiation with Near-Infrared Rays Subsequently, in order to confirm whether the photothermal effect of C-LPN leads to the anticancer effect on T47D cells, T74D and Hs578T cells were treated with IG-LPN or C-LPN and then irradiated with near-infrared rays to confirm the cell viability by WST assay.

Specifically, after T74D or Hs578T cells were inoculated into a 24-well plate at a density of $2\times10^5$ cells/well and cultured for 48 hours, the cells were treated with 300 μg/ml IG-LPN or C-LPN at 37° C. for 1 hour. Thereafter, the cells were harvested from the plate and centrifuged at 3000 rpm for 5 minutes to obtain a pellet. The obtained pellet was irradiated with a near-infrared ray of 808 nm with a diode laser beam (BWT Beijing Ltd.) at an output of 1.5 W for 5 minutes. Cells irradiated with near-infrared rays were inoculated into a 96-well plate, cultured at 37° C. for 24 hours, and then subjected to water soluble tetrazolium salt (WST) assay.

Figure 40:
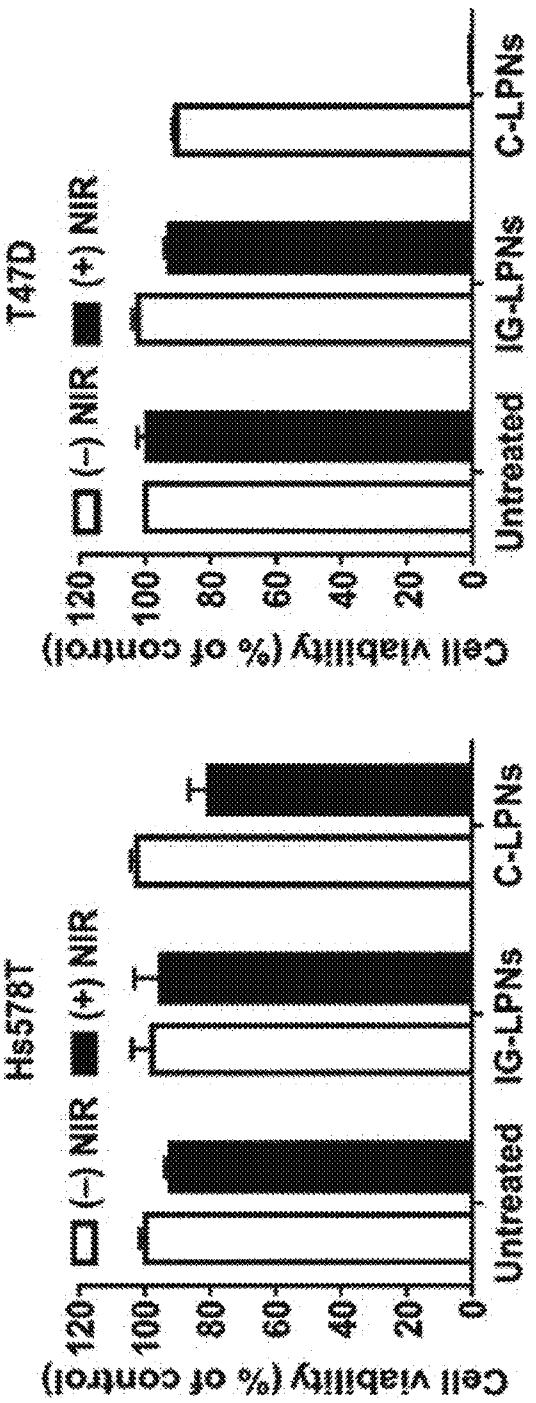
FIG. 40 is a set of views confirming the cell viability by WST assay by treating Hs578T cells or T47D cells with IG-LPN or C-LPN, and then irradiating the cells with near-infrared rays.

As a result, no significant cell death occurred when cells were not irradiated with near-infrared rays, regardless of cell or nanoparticle type. Further, it was found that in the case of Hs578T cells, no significant cell death occurred in both the IG-LPN treatment group and the IG-LPN treatment group, regardless of the irradiation with NIR. In contrast, it could be confirmed that when T47D cells were treated with IG-LPN, almost no cell death occurred in spite of irradiation with near-infrared rays, but when the cells were treated with C-LPN, and then irradiated with near-infrared rays, the cell viability was remarkably reduced to 2% or less (FIG. 40). The above results show that C-LPN according to the present invention is specifically accumulated in Claudin3-expressing cancer cells and effectively kills cancer cells by exhibiting a photothermal effect according to irradiation with near-infrared rays.

<14-3> Observation of Surviving Cancer Cells after Irradiation with Near-Infrared Rays Subsequently, according to Experimental Example 6-3, T74D and Hs578T cells were treated with IG-LPN or C-LPN and irradiated with near-infrared rays to observe dead and surviving cells under a fluorescence microscope.

Figure 41:
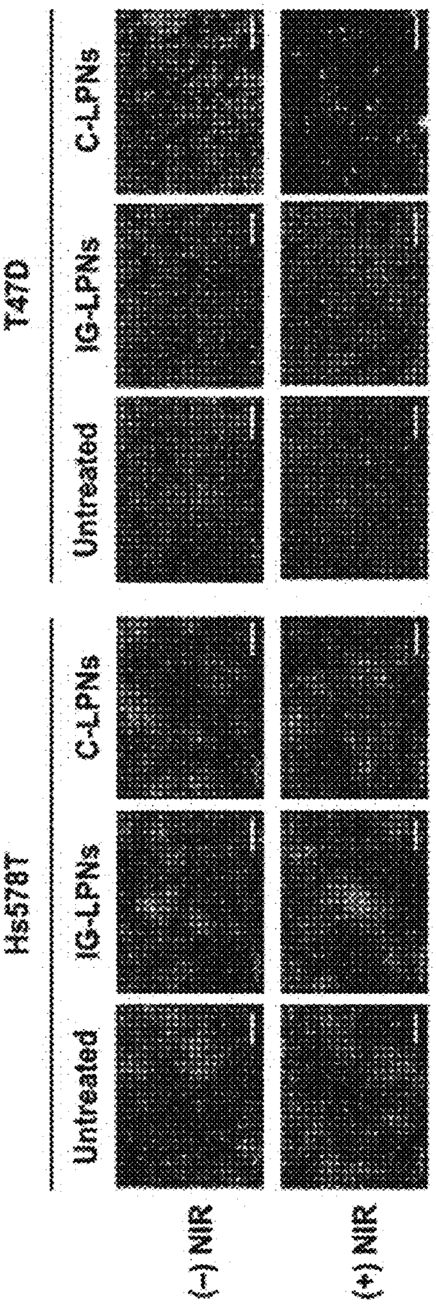
FIG. 41 is a set of views confirming the cell viability by a fluorescence microscope by treating Hs578T cells or T47D cells with IG-LPN or C-LPN, and then irradiating the cells with near-infrared rays.

As a result, similarly to the WST assay results, Hs578T cells, which are Claudin3-non-expressing cells, showed no significant difference in cell survival rate regardless of the type of nanoparticles or the presence or absence of irradiation with near-infrared rays, but it could be confirmed that when T47D cells, which are Claudin3-expressing cells, were treated with C-LPN and treated with near-infrared rays, the proportion of viable cells was definitely reduced (FIG. 41). Similarly to Experimental Example 14-2, the above results demonstrate that C-LPN exhibits an excellent photothermal therapeutic effect on Claudin3-expressing cancer cells.

<Experimental Example 15> Confirmation of C-LPN Distribution in Tumor Animal Model In order to confirm whether C-LPN is specifically accumulated in cancer tissues in an animal tumor model, the distribution of C-LPN or IG-LPN fluorescently-labeled with Cy5-bound lipid in an animal tumor model was confirmed.

Specifically, after 107 T47D cells per 100 μl of PBS were subcutaneously injected into the right flank of Balb/c mice (6 weeks old), Cy5-labeled IG-LPN or Cy5-labeled C-LPN was intravenously administered at a dose of 2 mg per mouse by randomly assigning mice when the volume of tumor reached 300 $mm^3$. The distribution of Cy5-labeled nanoparticles in the whole body of mice was confirmed at each hour by performing in vivo imaging with a near-infrared fluorescence imaging system, AMI-HT (Spectral Imaging Instruments, Tusson). 48 hours after injection, ex vivo imaging was performed by isolating the main organs and tissues.

As a result of confirming the distribution of nanoparticles in the whole body of mice, it could be confirmed that more C-LPN was accumulated in tumor tissue than IG-LPN 24 hours after the nanoparticles were injected (FIG. 42). In addition, it could be confirmed that even when ex-vivo imaging was performed by isolating the main organs and tissues 48 hours after the injection of nanoparticles, C-LPN was densely distributed in the tumor tissue compared to IG-LPN (FIG. 43). In particular, as a result of measuring the fluorescence intensity of tumor tissue and various organs, it could be confirmed that there was no significant difference between the IG-LPN-treatment group and the C-LPN-treatment group in normal tissue, but in the case of tumor tissue, the fluorescence intensity was 3.4-fold higher in the tumor tissue of the group treated with C-LPN than that of the group treated with IG-LPN (FIG. 44). The aforementioned results show that C-LPN according to the present invention can be specifically accumulated in tumor tissue.

<Experimental Example 16> Evaluation of Photothermal Therapeutic Effect of C-LPN in Tumor Animal Model Subsequently, in order to confirm whether the C-LPN according to the present invention exhibits a photothermal therapeutic effect in a tumor animal model, the animal model was treated with C-LPN or IG-LPN and then irradiated with near-infrared rays to confirm whether the growth of tumor was suppressed.

Figure 45:
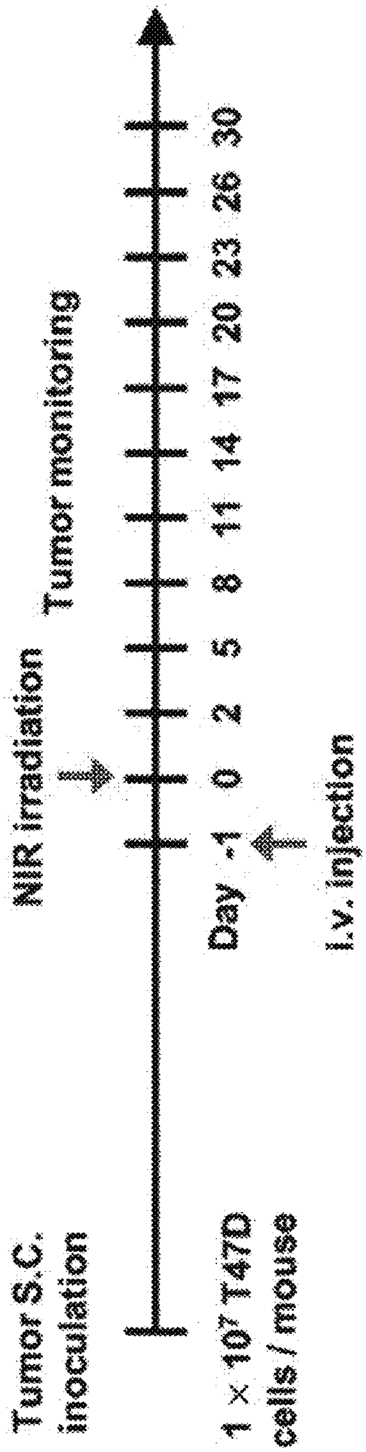
FIG. 45 is a view illustrating the process of injecting T47D cells into mice to prepare a tumor animal model, and then administering nanoparticles to the tumor animal model, and irradiating the tumor animal model with near-infrared rays.
Figure 46:
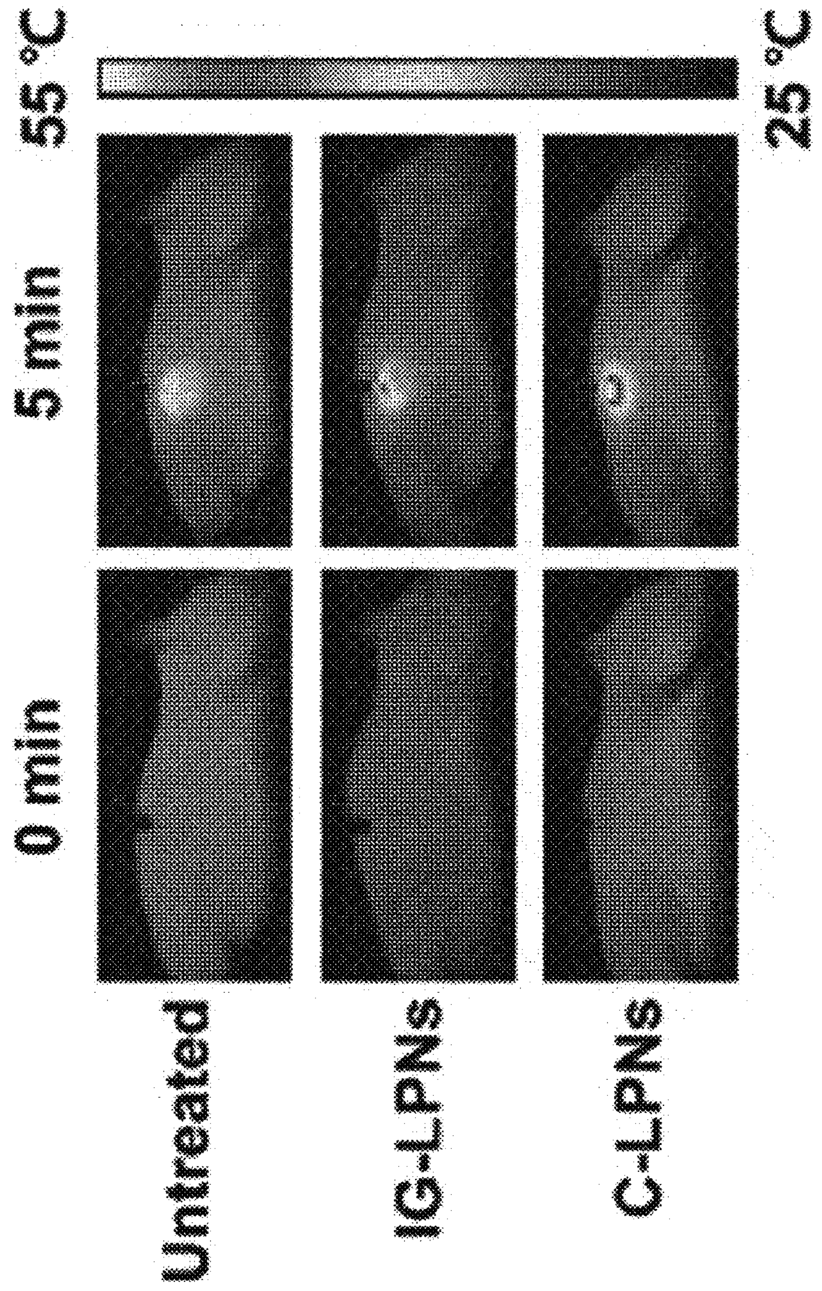
FIG. 46 confirms the change in temperature by a thermal imaging camera by treating a tumor animal model with IG-LPN or C-LPN and irradiating the tumor animal model with near-infrared rays, or after irradiating the tumor animal model with near-infrared rays, and is a set of views confirming that when mice treated with C-LPN were irradiated with near-infrared rays, heat spread over the entire tumor site.

FIG. 45 illustrates the process of preparing a tumor animal model, and then administering nanoparticles to the tumor animal model, and irradiating the tumor animal model with near-infrared rays. Specifically, after 107 T47D cells per 100 μl of PBS were subcutaneously injected into the right flank of Balb/c mice (6 weeks old), Cy5-labeled IG-LPN or Cy5-labeled C-LPN was intravenously administered at a dose of 2 mg per mouse by randomly assigning mice when the volume of tumor reached 300 $mm^3$. 24 hours later, three tumor sites in the mice were irradiated with an 808 nm near-infrared laser at a power of 1.5 W for 10 minutes.

Figure 47:
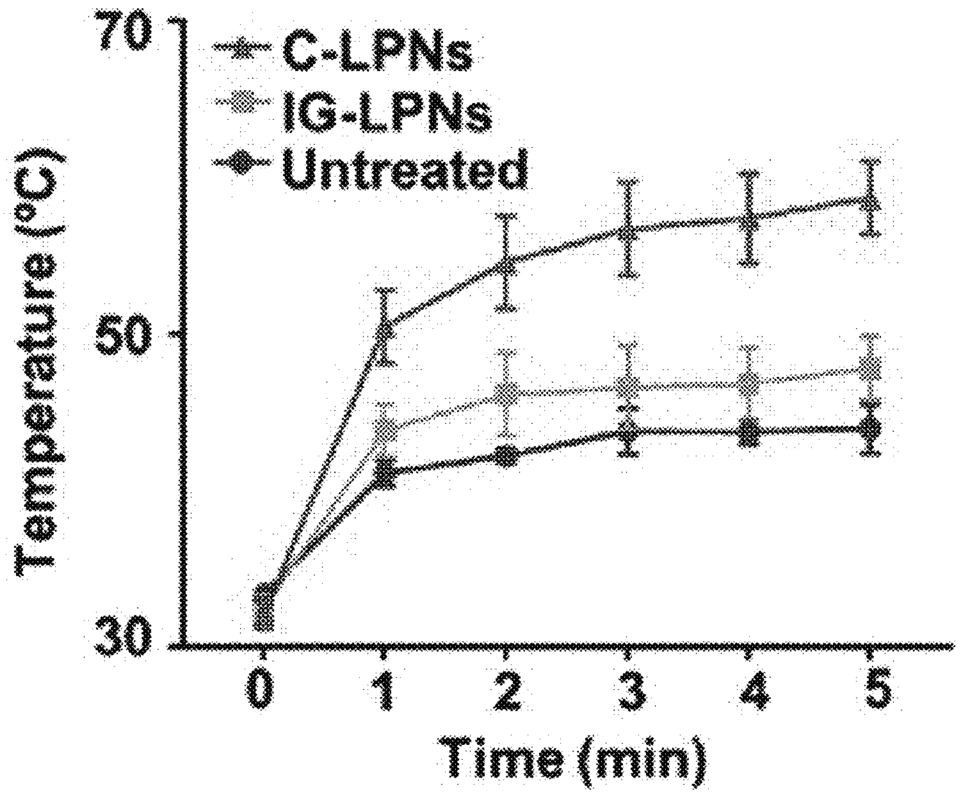
FIG. 47 illustrates the measurement of the change in temperature over time after treating a tumor animal model with IG-LPN or C-LPN and irradiating the tumor animal model with near-infrared rays, and is a view confirming that when the tumor animal model was treated with C-LPN, the temperature increased most.

<16-1> Evaluation of Photothermal Therapeutic Effect of C-LPN in Tumor Animal Model As a result of irradiating the tumor animal model treated with C-LPN or IG-LPN with near-infrared rays, and then confirming the change in temperature by a thermal imaging camera, it could be confirmed that in the case of C-LPN-treated mice, heat spread throughout the tumor site, whereas in IG-LPN-treated mice or control mice (untreated), heat was generated locally only at the point of laser irradiation (FIG. 45). As a result of accurately measuring the temperature, it was found that in the mice treated with C-LPN, the temperature of a tumor site was increased up to 60° C., and thus the temperature was increased by 10.9° C. or 14.8° C. or higher than that of IG-LPN-treated mice or control mice (FIG. 47). The aforementioned results show that C-LPN is distributed in tumor sites to effectively exhibit a photothermal effect.

Figure 48:
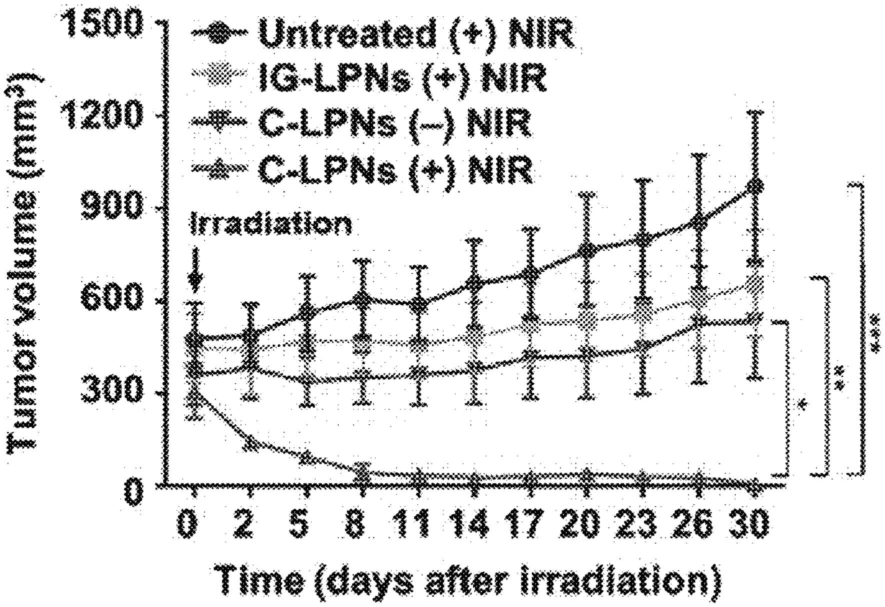
FIG. 48 illustrates the measurement of tumor volumes after treating a tumor animal model with IG-LPN or C-LPN and irradiating the tumor animal model with near-infrared rays, and is a view confirming that when the tumor animal model was treated with C-LPN and irradiated with near-infrared rays, the tumor volume was remarkably reduced.
Figure 49:
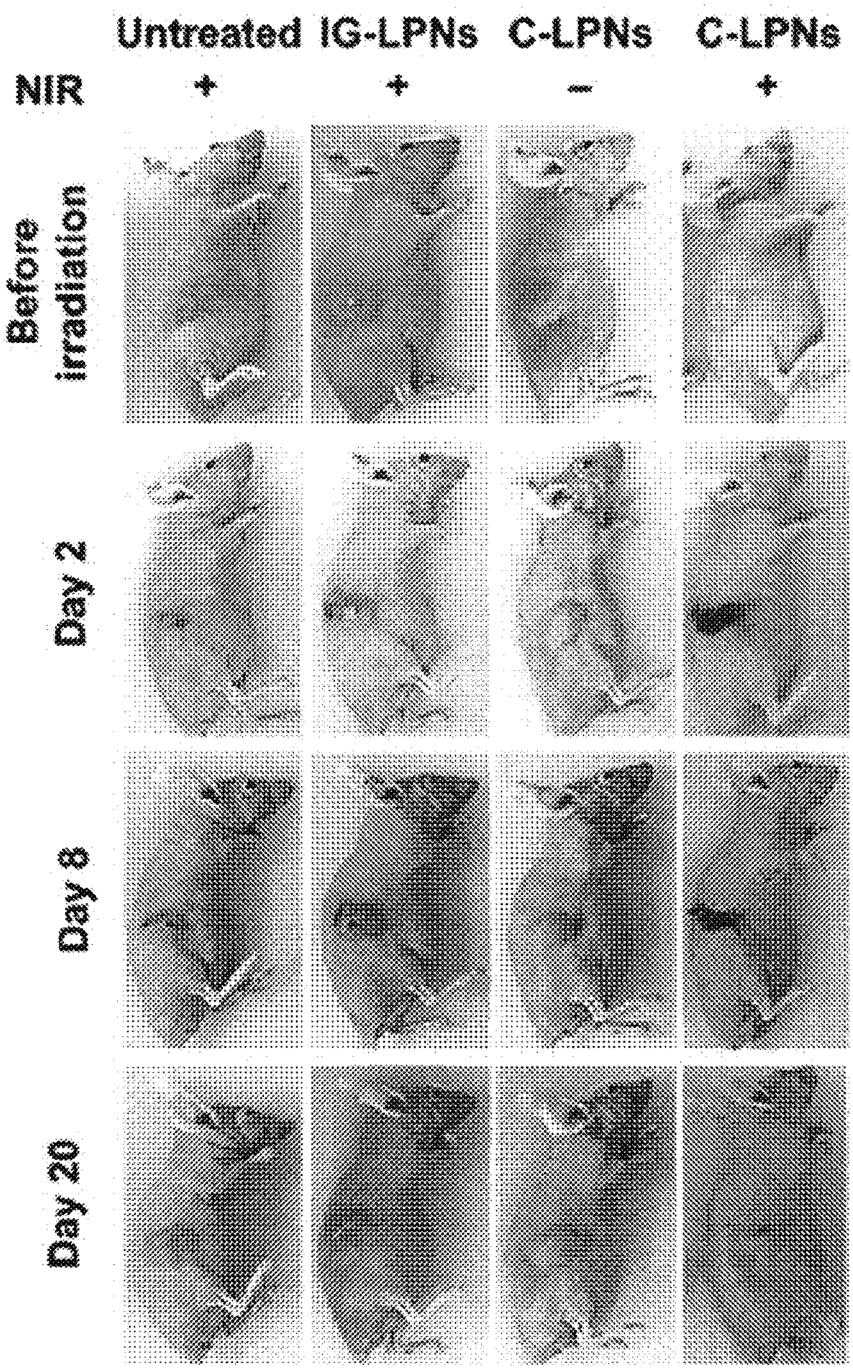
FIG. 49 illustrates the observation of the change in tumor site by the naked eye after treating a tumor animal model with IG-LPN or C-LPN and irradiating the tumor animal model with near-infrared rays, and is a set of views confirming that when the tumor animal model was treated with C-LPN and irradiated with near-infrared rays, tumor sites were tanned black, and the tumors disappeared completely on day 20.
Figure 50:
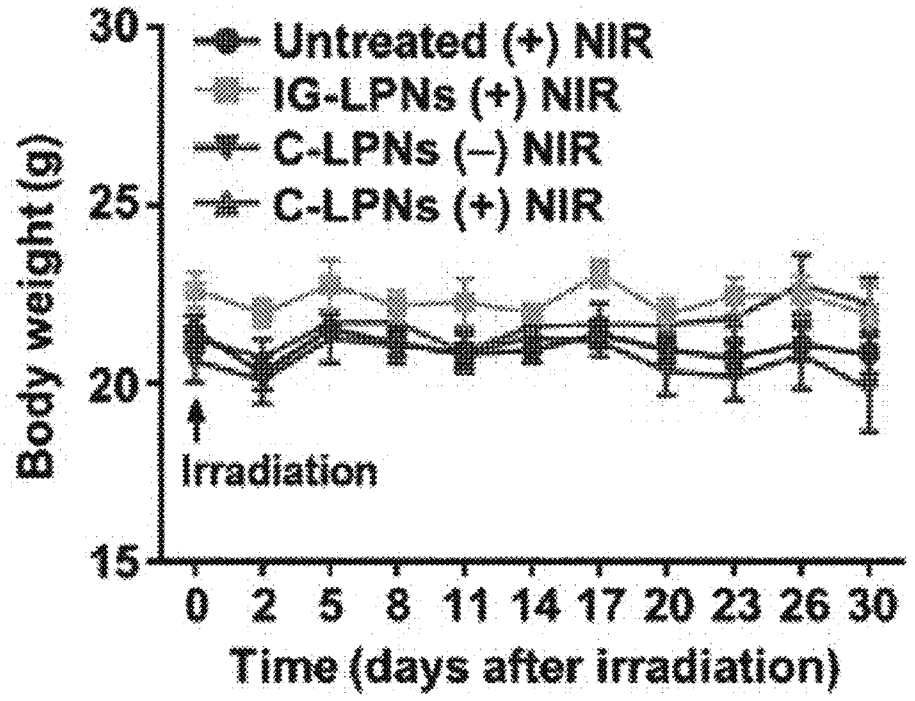
FIG. 50 illustrates the measurement of the body weights of animals after treating a tumor animal model with IG-LPN or C-LPN and irradiating the tumor animal model with near-infrared rays, and is a view confirming that there was no change in body weight.

<16-2> Evaluation of Tumor Suppression by Photothermal Effect of C-LPN in Tumor Animal Model In order to confirm whether the growth of tumor is suppressed by C-LPN in a tumor animal model, tumor volumes were measured after irradiating an animal tumor model treated with C-LPN or IG-LPN with near-infrared rays. Specifically, tumor volumes were measured twice weekly and calculated as follows: Tumor volume=length× $width^2/2$ As a result, it could be confirmed that in the group treated with IG-LPN, T47D tumors continued to grow even after irradiation with near-infrared rays, and in the group treated with C-LPN, T47D tumors also continued to grow/when the group was not irradiated with near-infrared rays, but tumors did not grow any more when mice treated with C-LPN were irradiated with near-infrared rays, and the tumors had disappeared 30 days after irradiation with near-infrared rays (FIG. 48). Furthermore, it could be confirmed that when the tumor animal model treated with nanoparticles and then irradiated with near-infrared rays was observed by the naked eye, the tumor sites of the mice treated with C-LPN and irradiated with near-infrared rays turned black, scab was produced on day 8 and peeled off on day 20, and the tumors had completely disappeared (FIG. 49). The aforementioned results demonstrate that the C-LPN according to the present invention can effectively suppress tumor growth by a photothermal effect even in an in vivo tumor model.

In particular, as a result of measuring the body weight of the tumor animal model treated with nanoparticles and then irradiated with near-infrared rays, the body weights of the animal models was confirmed to be constant regardless of the type of nanoparticle or the presence or absence of irradiation with near-infrared rays (FIG. 50), confirming that the nanoparticle treatment has no toxicity.

<16-3> Evaluation of Photothermal Therapeutic Effect of C-LPN in Tumor Animal Model Using H&E Staining Method and TUNEL Assay Subsequently, H&E staining method and cell death analysis (TUNEL assay) were performed on tissue cross sections of the tumor animal model to further validate the photothermal therapeutic effect of C-LPN.

Specifically, after tumor tissue was removed from the tumor animal model treated with nanoparticles and then irradiated with near-infrared rays, the tumor tissue was cut and stained with hematoxylin and eosin (H&E). In order to confirm apoptosis, terminal deoxy nucleotidyl transferase-mediated dUTP Nick end labeling (TUNEL) was performed using an ApopTag Peroxidase In Situ Apoptosis Detection Kit (Merck Millipore) according to the manufacturer's instructions.

Figure 51:
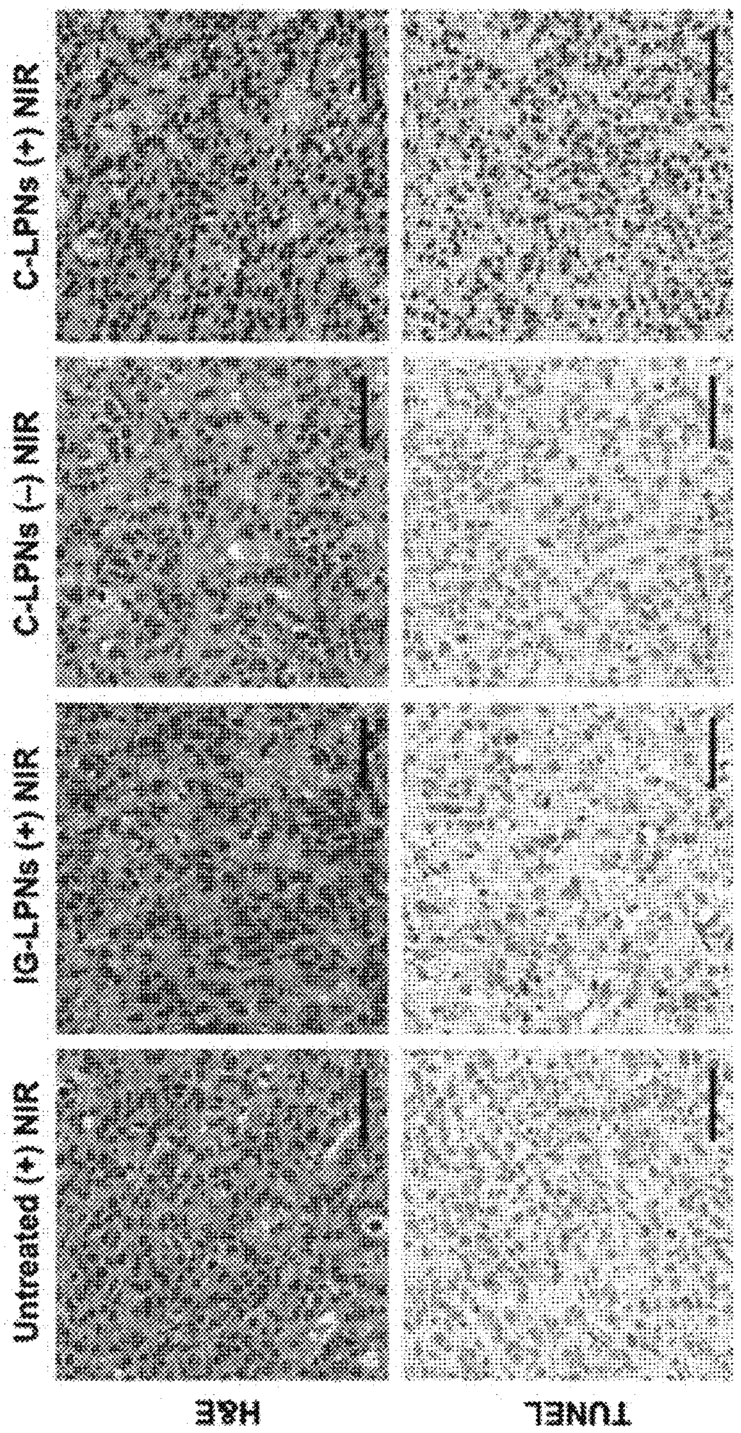
FIG. 51 illustrates that after treating a tumor animal model with IG-LPN or C-LPN and irradiating the tumor animal model with near-infrared rays, H&E staining (top) and TUNEL assay (bottom) were performed on tissue fragments, and is a set of views confirming that when the tumor animal model was treated with C-LPN and irradiated with near-infrared rays, cell apoptosis occurred actively.

As a result of H&E staining, it could be confirmed that cell nuclei were stained in a darker and fragmented state in the tumor tissue of mice treated with C-LPN and then treated with near-infrared rays compared to a comparative group (top of FIG. 51). Furthermore, as a result of TUNEL assay, it could be confirmed that cell apoptosis occurred most frequently in mice treated with C-LPN and then irradiated with near-infrared rays, and in the case of other mouse groups, cell apoptosis rarely occurred (bottom of FIG. 51). The aforementioned results demonstrate that the C-LPN according to the present invention effectively induces cancer cell death in an in vivo tumor model.

Figure 52:
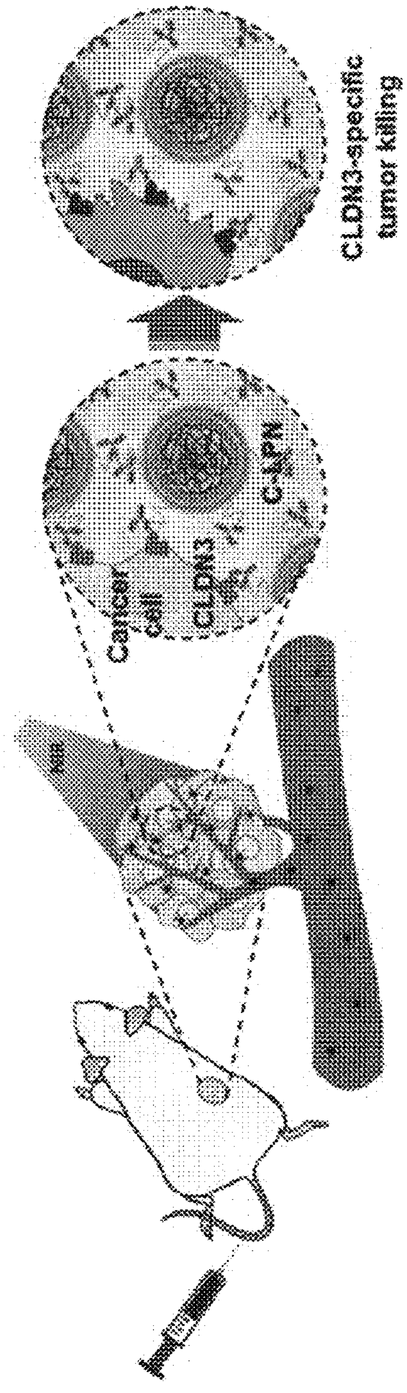
FIG. 52 is a view illustrating the process by which C-LPN acts on Claudin3-expressing cancer cells to induce cancer cell-specific death in a tumor animal model.

As a result of confirming the photothermal therapeutic effect of C-LPN using a tumor animal model as described above, it could be confirmed that the C-LPN according to the present invention specifically binds to cancer cells by an anti-Claudin3 antibody site-specifically conjugated to the surface of nanoparticles and effectively treats cancer by exhibiting a photothermal effect upon irradiation with near-infrared rays. The photothermal cancer therapeutic effect of C-LPN is schematically illustrated in FIG. 52.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

A phospholipid-photothermal nanoparticle according to the present invention has a cancer cell surface protein-specific antibody bound to the surface thereof, and thus can specifically bind to cancer cells, has a small particle size and excellent stability, and can effectively induce cancer cell apoptosis by exerting a photothermal effect when irradiated with near-infrared rays. Further, the present inventors confirmed that when the antibody or a fragment thereof is site-specifically conjugated to the phospholipid-photothermal nanoparticle, the cancer cell binding ability and the photothermal cancer therapeutic effect of the phospholipid-photothermal nanoparticle are further improved. Therefore, it is expected that the phospholipid-photothermal nanoparticle having an antibody bound to the surface thereof will be advantageously utilized for cancer therapy.

The invention claimed is:

1. A phospholipid-photothermal nanoparticle having an antibody bound to the surface thereof, comprising: a phospholipid membrane with entrapped photothermal nanoparticles; and an antibody specific for a surface protein of cancer cell selected from the group consisting of Claudin3, HER2, and prostate-specific membrane antigen (PSMA), or a fragment thereof, bound to the surface of the phospholipid membrane, wherein the phospholipid membrane comprises a phospholipid composition selected from the group consisting of (i) to (v): (i) 1,2-dipalmitoyl-sn-glycero-3-phosphocholine (DPPC) and 1,2-dipalmitoyl-sn-glycero-3-phosphorylglycerol (DPPG), (ii) 1,2-dipalmitoyl-sn-glycero-3-phosphocholine (DPPC) and phosphorylglycerol (PG), (iii) phosphocholine (PC) and 1,2-dipalmitoyl-sn-glycero-3-phosphorylglycerol (DPPG), (iv) phosphocholine (PC) and phosphorylglycerol (PG), and (v) phosphocholine (PC).

2. The phospholipid-photothermal nanoparticle having an antibody bound to the surface thereof of claim 1, wherein the photothermal nanoparticle generates heat by absorbing light in the near-infrared region.

3. The phospholipid-photothermal nanoparticle having an antibody bound to the surface thereof of claim 1, wherein the photothermal nanoparticle is a polydopamine nanoparticle, a gold nanoparticle, a graphene nanosheet, or a melanin nanoparticle.

4. The phospholipid-photothermal nanoparticle having an antibody bound to the surface thereof of claim 1, wherein the phospholipid membrane further comprises 1,2-distearoyl-sn-glycero-3-phosphoethanolamine-N-[maleimide (polyethyleneglycol)-2000] (DSPE-PEG2000-maleimide).

5. The phospholipid-photothermal nanoparticle having an antibody bound to the surface thereof of claim 1, wherein the phospholipid membrane comprises the phospholipid composition of DPPC and DPPG, and the DPPC and DPPG are present at a molar ratio of 5 to 9:1 to 5.

6. The phospholipid-photothermal nanoparticle having an antibody bound to the surface thereof of claim 1, wherein the antibody or a fragment thereof is bound to the surface end of a PEGylated phospholipid membrane.

7. The phospholipid-photothermal nanoparticle having an antibody bound to the surface thereof of claim 1, wherein the antibody or a fragment thereof is any one or more selected from the group consisting of IgG, Fab', $F(ab')_2$, Fab, Fv, a recombinant IgG (rIgG), a single chain Fv (scFv), and a diabody.

8. The phospholipid-photothermal nanoparticle having an antibody bound to the surface thereof of claim 1, wherein the antibody or a fragment thereof is any one or more selected from the group consisting of an anti-Claudin3 antibody or a fragment thereof; trastuzumab or a fragment thereof; and an anti-PSMA antibody or a fragment thereof.

9. The phospholipid-photothermal nanoparticle having an antibody bound to the surface thereof of claim 1, wherein the phospholipid-photothermal nanoparticles have a particle size of 100 to 250 nm.

10. The phospholipid-photothermal nanoparticle having an antibody bound to the surface thereof of claim 1, wherein the antibody or a fragment thereof is modified so as to have a free thiol group, and the phospholipid membrane comprises a phospholipid to which maleimide is bound.

11. The phospholipid-photothermal nanoparticle having an antibody bound to the surface thereof of claim 10, wherein the free thiol group is present in the constant site of the light chain of the antibody or a fragment thereof.

12. The phospholipid-photothermal nanoparticle having an antibody bound to the surface thereof of claim 10, wherein the free thiol group of the antibody or a fragment thereof binds to the maleimide of the phospholipid membrane.

13. The phospholipid-photothermal nanoparticle having an antibody bound to the surface thereof of claim 10, wherein the phospholipid to which maleimide is bound is DSPE-PEG2000-maleimide.

14. The phospholipid-photothermal nanoparticle having an antibody bound to the surface thereof of claim 10, wherein the antibody or a fragment thereof is an anti-Claudin3 antibody modified so as to have a free thiol group, or a fragment thereof, and satisfies one or more of the following characteristics: (a) the modified anti-Claudin3 antibody or a fragment thereof is an anti-Claudin3 antibody comprising the amino acid sequence of SEQ ID NO: 9, in which the 17 glutamine residue in the amino acid sequence of SEQ ID NO: 8 is substituted with a cysteine residue, or a fragment thereof; or (b) the modified anti-Claudin3 antibody or a fragment thereof is an anti-Claudin3 antibody comprising the amino acid sequence of SEQ ID NO: 11, in which the 125 glutamine residue in the amino acid sequence of SEQ ID NO: 10 is substituted with a cysteine residue, or a fragment thereof.

15. The phospholipid-photothermal nanoparticle having an antibody bound to the surface thereof of claim 14, wherein the anti-Claudin3 antibody modified so as to have a free thiol group, or a fragment thereof comprises:

a light chain variable region comprising of the amino acid sequences of SEQ ID NO: 7; and a heavy chain variable region comprising the amino acid sequences of SEQ ID NO: 15.

16. A pharmaceutical composition for treating cancer, comprising the phospholipid-photothermal nanoparticle having an antibody bound to the surface thereof of claim 1 as an active ingredient.

17. The pharmaceutical composition of claim 16, wherein the antibody or a fragment thereof is an anti-Claudin3 antibody or a fragment thereof, and the cancer is a cancer expressing Claudin3.

18. The pharmaceutical composition of claim 17, wherein the cancer is one or more selected from the group consisting of ovarian cancer, gastric cancer, colorectal cancer, prostate cancer, pancreatic cancer, and breast cancer.

19. The pharmaceutical composition of claim 16, wherein the phospholipid-photothermal nanoparticle induces the death of cancer cells upon irradiation with therapeutically effective light.

* * * * *

SEQUENCE LISTING

```
<160> NUMBER OF SEQ ID NOS: 41

<210> SEQ ID NO 1
<211> LENGTH: 220
<212> TYPE: PRT
<213> ORGANISM: Homo sapiens

<400> SEQUENCE: 1

Met Ser Met Gly Leu Glu Ile Thr Gly Thr Ala Leu Ala Val Leu Gly
1               5                   10                  15

Trp Leu Gly Thr Ile Val Cys Cys Ala Leu Pro Met Trp Arg Val Ser
            20                  25                  30

Ala Phe Ile Gly Ser Asn Ile Ile Thr Ser Gln Asn Ile Trp Glu Gly
        35                  40                  45

Leu Trp Met Asn Cys Val Val Gln Ser Thr Gly Gln Met Gln Cys Lys
    50                  55                  60

Val Tyr Asp Ser Leu Leu Ala Leu Pro Gln Asp Leu Gln Ala Ala Arg
65                  70                  75                  80

Ala Leu Ile Val Val Ala Ile Leu Leu Ala Ala Phe Gly Leu Leu Val
                85                  90                  95

Ala Leu Val Gly Ala Gln Cys Thr Asn Cys Val Gln Asp Asp Thr Ala
            100                 105                 110

Lys Ala Lys Ile Thr Ile Val Ala Gly Val Leu Phe Leu Leu Ala Ala
        115                 120                 125

Leu Leu Thr Leu Val Pro Val Ser Trp Ser Ala Asn Thr Ile Ile Arg
    130                 135                 140

Asp Phe Tyr Asn Pro Val Val Pro Glu Ala Gln Lys Arg Glu Met Gly
145                 150                 155                 160

Ala Gly Leu Tyr Val Gly Trp Ala Ala Ala Ala Leu Gln Leu Leu Gly
                165                 170                 175

Gly Ala Leu Leu Cys Cys Ser Cys Pro Pro Arg Glu Lys Lys Tyr Thr
            180                 185                 190

Ala Thr Lys Val Val Tyr Ser Ala Pro Arg Ser Thr Gly Pro Gly Ala
        195                 200                 205

Ser Leu Gly Thr Gly Tyr Asp Arg Lys Asp Tyr Val
    210                 215                 220


<210> SEQ ID NO 2
<211> LENGTH: 1255
<212> TYPE: PRT
<213> ORGANISM: Homo sapiens

<400> SEQUENCE: 2

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
```

-continued

```
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525
```

-continued

```
Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940
```

-continued

```
Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
        1075                1080                1085

Asp Leu Gly Met Gly Ala Ala Lys Gly Leu Gln Ser Leu Pro Thr His
    1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
        1155                1160                1165

Arg Pro Lys Thr Leu Ser Pro Gly Lys Asn Gly Val Val Lys Asp Val
    1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
                1205                1210                1215

Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
        1235                1240                1245

Leu Gly Leu Asp Val Pro Val
    1250                1255


<210> SEQ ID NO 3
<211> LENGTH: 750
<212> TYPE: PRT
<213> ORGANISM: Homo sapiens

<400> SEQUENCE: 3

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60
```

-continued

```
Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480
```

-continued

```
Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750
```

<210> SEQ ID NO 4
<211> LENGTH: 13
<212> TYPE: PRT
<213> ORGANISM: Artificial Sequence
<220> FEATURE:
<223> OTHER INFORMATION: Claudin3 antibody_light chain_variable region_CDR1

<400> SEQUENCE: 4

```
Ser Gly Ser Thr Ser Asn Ile Gly Arg Asn Tyr Val Ser
1               5                   10
```

<210> SEQ ID NO 5
<211> LENGTH: 7
<212> TYPE: PRT
<213> ORGANISM: Artificial Sequence
<220> FEATURE:
<223> OTHER INFORMATION: Claudin3 antibody_light chain_variable region_CDR2

<400> SEQUENCE: 5

```
Asp Thr Ser Asn Lys His Phe
1               5
```

<210> SEQ ID NO 6
<211> LENGTH: 9
<212> TYPE: PRT
<213> ORGANISM: Artificial Sequence
<220> FEATURE:
<223> OTHER INFORMATION: Claudin3 antibody_light chain_variable region_CDR3

<400> SEQUENCE: 6

```
Gln Ser Tyr Asp Ser Ser Lys Val Val
1               5
```

<210> SEQ ID NO 7
<211> LENGTH: 108
<212> TYPE: PRT
<213> ORGANISM: Artificial Sequence
<220> FEATURE:
<223> OTHER INFORMATION: Claudin3 antibody_light chain_variable region

<400> SEQUENCE: 7

```
Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Arg Asn
            20                  25                  30

Tyr Val Ser Trp Tyr Gln Gln Leu Pro Gly Thr Ala Pro Lys Leu Leu
        35                  40                  45

Ile Tyr Asp Thr Ser Asn Lys His Phe Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Lys
                85                  90                  95

Val Val Phe Gly Gly Gly Thr Lys Leu Thr Val Leu
            100                 105
```

<210> SEQ ID NO 8
<211> LENGTH: 107
<212> TYPE: PRT
<213> ORGANISM: Artificial Sequence
<220> FEATURE:
<223> OTHER INFORMATION: Claudin3 antibody_light chain_constant region

<400> SEQUENCE: 8

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 9
<211> LENGTH: 107

<212> TYPE: PRT
<213> ORGANISM: Artificial Sequence
<220> FEATURE:
<223> OTHER INFORMATION: Claudin3 antibody(modified)_light chain_constant region

<400> SEQUENCE: 9

```
Arg Thr Val Ala Ala Pro Ser Val Phe Ile Phe Pro Pro Ser Asp Glu
1               5                   10                  15

Cys Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 10
<211> LENGTH: 215
<212> TYPE: PRT
<213> ORGANISM: Artificial Sequence
<220> FEATURE:
<223> OTHER INFORMATION: Claudin3 antibody_light chain

<400> SEQUENCE: 10

```
Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Arg Asn
            20                  25                  30

Tyr Val Ser Trp Tyr Gln Gln Leu Pro Gly Thr Ala Pro Lys Leu Leu
        35                  40                  45

Ile Tyr Asp Thr Ser Asn Lys His Phe Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Lys
                85                  90                  95

Val Val Phe Gly Gly Gly Thr Lys Leu Thr Val Leu Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
```

```
    210                 215


<210> SEQ ID NO 11
<211> LENGTH: 215
<212> TYPE: PRT
<213> ORGANISM: Artificial Sequence
<220> FEATURE:
<223> OTHER INFORMATION: Claudin3 antibody(modified)_light chain

<400> SEQUENCE: 11

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Arg Asn
            20                  25                  30

Tyr Val Ser Trp Tyr Gln Gln Leu Pro Gly Thr Ala Pro Lys Leu Leu
        35                  40                  45

Ile Tyr Asp Thr Ser Asn Lys His Phe Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Lys
                85                  90                  95

Val Val Phe Gly Gly Gly Thr Lys Leu Thr Val Leu Arg Thr Val Ala
            100                 105                 110

Ala Pro Ser Val Phe Ile Phe Pro Pro Ser Asp Glu Cys Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 12
<211> LENGTH: 5
<212> TYPE: PRT
<213> ORGANISM: Artificial Sequence
<220> FEATURE:
<223> OTHER INFORMATION: Claudin3 antibody_heavy chain_variable
      region_CDR1

<400> SEQUENCE: 12

Ser Tyr Ala Met Ser
1               5


<210> SEQ ID NO 13
<211> LENGTH: 18
<212> TYPE: PRT
<213> ORGANISM: Artificial Sequence
<220> FEATURE:
<223> OTHER INFORMATION: Claudin3 antibody_heavy chain_variable
      region_CDR2

<400> SEQUENCE: 13
```

-continued

```
Ser Ile Ile Asn Pro Ser Gly Ala Ser Thr Ser His Ala Gln Arg Phe
1               5                   10                  15

Gln Gly


<210> SEQ ID NO 14
<211> LENGTH: 9
<212> TYPE: PRT
<213> ORGANISM: Artificial Sequence
<220> FEATURE:
<223> OTHER INFORMATION: Claudin3 antibody_heavy chain_variable
      region_CDR3

<400> SEQUENCE: 14

Tyr Gly Arg Tyr Gly Ser Phe Asp Ile
1               5


<210> SEQ ID NO 15
<211> LENGTH: 118
<212> TYPE: PRT
<213> ORGANISM: Artificial Sequence
<220> FEATURE:
<223> OTHER INFORMATION: Claudin3 antibody_heavy chain_variable region

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ile Ile Asn Pro Ser Gly Ala Ser Thr Ser His Ala Gln Arg Phe
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Tyr Gly Ser Phe Asp Ile Trp Gly Gln Gly Thr
            100                 105                 110

Leu Val Thr Val Ser Ser
        115


<210> SEQ ID NO 16
<211> LENGTH: 330
<212> TYPE: PRT
<213> ORGANISM: Artificial Sequence
<220> FEATURE:
<223> OTHER INFORMATION: Claudin3 antibody_heavy chain_constant region

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

-continued

```
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 17
<211> LENGTH: 448
<212> TYPE: PRT
<213> ORGANISM: Artificial Sequence
<220> FEATURE:
<223> OTHER INFORMATION: Claudin3 antibody_heavy chain

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ile Ile Asn Pro Ser Gly Ala Ser Thr Ser His Ala Gln Arg Phe
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Tyr Gly Ser Phe Asp Ile Trp Gly Gln Gly Thr
            100                 105                 110

Leu Val Thr Val Ser Ser Ala Ser Thr Lys Gly Pro Ser Val Phe Pro
```

-continued

```
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 18
<211> LENGTH: 11
<212> TYPE: PRT
<213> ORGANISM: Artificial Sequence
<220> FEATURE:
<223> OTHER INFORMATION: HER2 antibody_light chain_variable region_CDR1

<400> SEQUENCE: 18

Arg Ala Ser Gln Asp Val Asn Thr Ala Val Ala
1               5                   10


<210> SEQ ID NO 19
<211> LENGTH: 6
<212> TYPE: PRT
```

<213> ORGANISM: Artificial Sequence
<220> FEATURE:
<223> OTHER INFORMATION: HER2 antibody_light chain_variable region_CDR2

<400> SEQUENCE: 19

Ser Ala Ser Phe Leu Tyr
1               5

<210> SEQ ID NO 20
<211> LENGTH: 8
<212> TYPE: PRT
<213> ORGANISM: Artificial Sequence
<220> FEATURE:
<223> OTHER INFORMATION: HER2 antibody_light chain_variable region_CDR3

<400> SEQUENCE: 20

Gln Gln His Tyr Thr Thr Pro Pro
1               5

<210> SEQ ID NO 21
<211> LENGTH: 107
<212> TYPE: PRT
<213> ORGANISM: Artificial Sequence
<220> FEATURE:
<223> OTHER INFORMATION: HER2 antibody_light chain_variable region

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: HER2 antibody_light chain_constant region

<400> SEQUENCE: 22

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser

```
                85                  90                  95

Pro Val Thr Lys Ser Phe Asn Arg Gly Glu Cys
            100                 105


<210> SEQ ID NO 23
<211> LENGTH: 214
<212> TYPE: PRT
<213> ORGANISM: Artificial Sequence
<220> FEATURE:
<223> OTHER INFORMATION: HER2 antibody_light chain

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 24
<211> LENGTH: 10
<212> TYPE: PRT
<213> ORGANISM: Artificial Sequence
<220> FEATURE:
<223> OTHER INFORMATION: HER2 antibody_heavy chain_variable region_CDR1

<400> SEQUENCE: 24

Gly Phe Asn Ile Lys Asp Thr Tyr Ile His
1               5                   10


<210> SEQ ID NO 25
<211> LENGTH: 18
<212> TYPE: PRT
<213> ORGANISM: Artificial Sequence
<220> FEATURE:
<223> OTHER INFORMATION: HER2 antibody_heavy chain_variable region_CDR2

<400> SEQUENCE: 25
```

Ala Arg Ile Tyr Pro Thr Asn Gly Tyr Thr Arg Tyr Ala Asp Ser Val
1 5 10 15

Lys Gly

<210> SEQ ID NO 26
<211> LENGTH: 13
<212> TYPE: PRT
<213> ORGANISM: Artificial Sequence
<220> FEATURE:
<223> OTHER INFORMATION: HER2 antibody_heavy chain_variable region_CDR3

<400> SEQUENCE: 26

Ser Arg Trp Gly Gly Asp Gly Phe Tyr Ala Met Asp Tyr
1 5 10

<210> SEQ ID NO 27
<211> LENGTH: 120
<212> TYPE: PRT
<213> ORGANISM: Artificial Sequence
<220> FEATURE:
<223> OTHER INFORMATION: HER2 antibody_heavy chain_variable region

<400> SEQUENCE: 27

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser
115 120

<210> SEQ ID NO 28
<211> LENGTH: 330
<212> TYPE: PRT
<213> ORGANISM: Artificial Sequence
<220> FEATURE:
<223> OTHER INFORMATION: HER2 antibody_heavy chain_constant region

<400> SEQUENCE: 28

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys

-continued

```
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 29
<211> LENGTH: 450
<212> TYPE: PRT
<213> ORGANISM: Artificial Sequence
<220> FEATURE:
<223> OTHER INFORMATION: HER2 antibody_heavy chain

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
```

-continued

```
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 30
<211> LENGTH: 11
<212> TYPE: PRT
<213> ORGANISM: Artificial Sequence
<220> FEATURE:
<223> OTHER INFORMATION: PSMA antibody_light chain_variable region_CDR1

<400> SEQUENCE: 30

Lys Ala Ser Gln Asp Val Gly Thr Ala Val Asp
1               5                   10
```

<210> SEQ ID NO 31
<211> LENGTH: 7
<212> TYPE: PRT
<213> ORGANISM: Artificial Sequence
<220> FEATURE:
<223> OTHER INFORMATION: PSMA antibody_light chain_variable region_CDR2

<400> SEQUENCE: 31

```
Trp Ala Ser Thr Arg His Thr
1               5
```

<210> SEQ ID NO 32
<211> LENGTH: 9
<212> TYPE: PRT
<213> ORGANISM: Artificial Sequence
<220> FEATURE:
<223> OTHER INFORMATION: PSMA antibody_light chain_variable region_CDR3

<400> SEQUENCE: 32

```
Gln Gln Tyr Asn Ser Tyr Pro Leu Thr
1               5
```

<210> SEQ ID NO 33
<211> LENGTH: 107
<212> TYPE: PRT
<213> ORGANISM: Artificial Sequence
<220> FEATURE:
<223> OTHER INFORMATION: PSMA antibody_light chain_variable region

<400> SEQUENCE: 33

```
Asp Ile Gln Met Thr Gln Ser Pro Ser Ser Leu Ser Thr Ser Val Gly
1               5                   10                  15

Asp Arg Val Thr Leu Thr Cys Lys Ala Ser Gln Asp Val Gly Thr Ala
            20                  25                  30

Val Asp Trp Tyr Gln Gln Lys Pro Gly Pro Ser Pro Lys Leu Leu Ile
        35                  40                  45

Tyr Trp Ala Ser Thr Arg His Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Tyr Asn Ser Tyr Pro Leu
                85                  90                  95

Thr Phe Gly Pro Gly Thr Lys Val Asp Ile Lys
            100                 105
```

<210> SEQ ID NO 34
<211> LENGTH: 107
<212> TYPE: PRT
<213> ORGANISM: Artificial Sequence
<220> FEATURE:
<223> OTHER INFORMATION: PSMA antibody_light chain_constant region

<400> SEQUENCE: 34

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
```

-continued

```
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 35
<211> LENGTH: 214
<212> TYPE: PRT
<213> ORGANISM: Artificial Sequence
<220> FEATURE:
<223> OTHER INFORMATION: PSMA antibody_light chain

<400> SEQUENCE: 35

Asp Ile Gln Met Thr Gln Ser Pro Ser Ser Leu Ser Thr Ser Val Gly
1               5                   10                  15

Asp Arg Val Thr Leu Thr Cys Lys Ala Ser Gln Asp Val Gly Thr Ala
            20                  25                  30

Val Asp Trp Tyr Gln Gln Lys Pro Gly Pro Ser Pro Lys Leu Leu Ile
        35                  40                  45

Tyr Trp Ala Ser Thr Arg His Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Tyr Asn Ser Tyr Pro Leu
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 36
<211> LENGTH: 10
<212> TYPE: PRT
<213> ORGANISM: Artificial Sequence
<220> FEATURE:
<223> OTHER INFORMATION: PSMA antibody_heavy chain_variable region_CDR1

<400> SEQUENCE: 36

Gly Tyr Thr Phe Thr Glu Tyr Thr Ile His
1               5                   10


<210> SEQ ID NO 37
<211> LENGTH: 17
<212> TYPE: PRT
<213> ORGANISM: Artificial Sequence
<220> FEATURE:
```

<223> OTHER INFORMATION: PSMA antibody_heavy chain_variable region_CDR2

<400> SEQUENCE: 37

Asn Ile Asn Pro Asn Asn Gly Gly Thr Thr Tyr Asn Gln Lys Phe Glu
1               5                   10                  15

Asp

<210> SEQ ID NO 38
<211> LENGTH: 6
<212> TYPE: PRT
<213> ORGANISM: Artificial Sequence
<220> FEATURE:
<223> OTHER INFORMATION: PSMA antibody_heavy chain_variable region_CDR3

<400> SEQUENCE: 38

Gly Trp Asn Phe Asp Tyr
1               5

<210> SEQ ID NO 39
<211> LENGTH: 115
<212> TYPE: PRT
<213> ORGANISM: Artificial Sequence
<220> FEATURE:
<223> OTHER INFORMATION: PSMA antibody_heavy chain_variable region

<400> SEQUENCE: 39

Glu Val Gln Leu Val Gln Ser Gly Pro Glu Val Lys Lys Pro Gly Ala
1               5                   10                  15

Thr Val Lys Ile Ser Cys Lys Thr Ser Gly Tyr Thr Phe Thr Glu Tyr
            20                  25                  30

Thr Ile His Trp Val Lys Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Leu Thr
            100                 105                 110

Val Ser Ser
        115

<210> SEQ ID NO 40
<211> LENGTH: 330
<212> TYPE: PRT
<213> ORGANISM: Artificial Sequence
<220> FEATURE:
<223> OTHER INFORMATION: PSMA antibody_heavy chain_constant region

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr

-continued

```
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 41
<211> LENGTH: 445
<212> TYPE: PRT
<213> ORGANISM: Artificial Sequence
<220> FEATURE:
<223> OTHER INFORMATION: PSMA antibody_heavy chain

<400> SEQUENCE: 41

Glu Val Gln Leu Val Gln Ser Gly Pro Glu Val Lys Lys Pro Gly Ala
1               5                   10                  15

Thr Val Lys Ile Ser Cys Lys Thr Ser Gly Tyr Thr Phe Thr Glu Tyr
            20                  25                  30

Thr Ile His Trp Val Lys Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Leu Thr
```

-continued

```
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```